US010980745B2

(12) United States Patent
Solfato et al.

(10) Patent No.: US 10,980,745 B2
(45) Date of Patent: Apr. 20, 2021

(54) MICROEMULSION COMPOSITIONS

(71) Applicants: SIFI S.p.A., Aci Sant' Antonio (IT); Consiglio Nazionale delle Ricerche, Rome (IT)

(72) Inventors: Elena Solfato, Catania (IT); Ilenia Abbate, Acireale (IT); Cristina Maria Concetta Zappulla, Catania (IT); Manuela Santonocito, Mascalucia (IT); Santa Viola, Paterno (IT); Sandro De Falco, Naples (IT); Francesco Giuliano, Mascalucia (IT)

(73) Assignees: SIFI S.p.A., Catania (IT); Consiglio Nazionale delle Ricerche, Rome (IT)

( * ) Notice: Subject to any disclaimer, the term of this patent is extended or adjusted under 35 U.S.C. 154(b) by 0 days.

(21) Appl. No.: 16/590,246

(22) Filed: Oct. 1, 2019

(65) Prior Publication Data
US 2020/0390699 A1    Dec. 17, 2020

Related U.S. Application Data

(63) Continuation of application No. PCT/IT2019/000048, filed on Jun. 11, 2019.

(51) Int. Cl.
*A61K 9/00* (2006.01)
*A61K 9/107* (2006.01)
*A61P 27/02* (2006.01)
*A61K 31/5575* (2006.01)
*A61K 31/05* (2006.01)
*A61K 31/44* (2006.01)
*A61K 47/44* (2017.01)
*A61P 27/04* (2006.01)
*A61K 47/14* (2017.01)
*A61K 47/10* (2017.01)
*A61K 47/12* (2006.01)
*A61K 47/26* (2006.01)

(52) U.S. Cl.
CPC .......... *A61K 9/1075* (2013.01); *A61K 9/0048* (2013.01); *A61K 31/05* (2013.01); *A61K 31/44* (2013.01); *A61K 31/5575* (2013.01); *A61K 47/10* (2013.01); *A61K 47/12* (2013.01); *A61K 47/14* (2013.01); *A61K 47/26* (2013.01); *A61K 47/44* (2013.01); *A61P 27/02* (2018.01); *A61P 27/04* (2018.01)

(58) Field of Classification Search
CPC ...... A61K 9/0048; A61K 9/1075; A61P 27/02
See application file for complete search history.

(56) References Cited

U.S. PATENT DOCUMENTS

| | | | |
|---|---|---|---|
| 8,158,687 B2 | 4/2012 | Yaghmur et al. | 516/56 |
| 8,288,348 B2 | 10/2012 | Chang et al. | 514/19.9 |
| 8,414,904 B2 | 4/2013 | Carli et al. | 424/400 |
| 8,629,111 B2 | 1/2014 | Acheampong et al. | 514/20.5 |
| 8,633,162 B2 | 1/2014 | Acheampong et al. | 514/20.5 |
| 8,642,556 B2 | 2/2014 | Acheampong et al. | 514/20.5 |
| 8,648,048 B2 | 2/2014 | Acheampong et al. | 514/20.5 |
| 8,685,930 B2 | 4/2014 | Acheampong et al. | 514/20.5 |
| 8,834,903 B2 | 9/2014 | Simonnet et al. | 424/401 |
| 8,912,164 B2 | 12/2014 | Mazzone et al. | 514/54 |
| 8,968,775 B2 | 3/2015 | Wassel et al. | 424/455 |
| 9,149,453 B2 | 10/2015 | Wassel et al. | 424/455 |
| 9,161,906 B2 | 10/2015 | Mazzone et al. | 424/451 |
| 9,248,191 B2 | 2/2016 | Acheampong et al. | 514/20.5 |
| 9,539,208 B2 | 1/2017 | Tamarkin et al. | 424/47 |
| 9,907,826 B2 | 3/2018 | Simmons et al. | 514/547 |
| 2003/0109422 A1 | 6/2003 | Mazzone et al. | 514/6 |
| 2006/0251685 A1 | 11/2006 | Yu et al. | 424/400 |
| 2007/0036829 A1 | 2/2007 | Yu et al. | 424/400 |
| 2009/0221545 A1 | 9/2009 | Giammona et al. | 514/183 |
| 2010/0305045 A1 | 12/2010 | Yu | 514/20.5 |
| 2010/0305046 A1 | 12/2010 | Yu | 514/20.5 |
| 2013/0059796 A1 | 3/2013 | Chang et al. | 514/20.5 |
| 2014/0302146 A1 | 10/2014 | Kurose et al. | 424/489 |
| 2016/0101050 A1* | 4/2016 | Lee | A61K 9/1075 424/400 |
| 2017/0143627 A1* | 5/2017 | Misra | A61K 47/22 |
| 2018/0333357 A1* | 11/2018 | Arumugham | A61P 27/02 |

FOREIGN PATENT DOCUMENTS

| | | |
|---|---|---|
| EP | 1284143 | 2/2003 |
| EP | 2136782 | 6/2013 |
| EP | 2659903 | 9/2016 |
| EP | 2968139 | 5/2018 |
| WO | WO 1995/031211 | 11/1995 |

(Continued)

OTHER PUBLICATIONS

Letter/Written Disclosure of the Information Disclosure Statement for the above-referenced application, filed herewith on Dec. 23, 2019, 2 pages.
Costagliola et al., "Some Physicochemical Remarks on Spontaneous Emulsification of Vitreal Tamponades," Biomed Res Int. 2014:243056 (2014), 6 pages.
Gursoy, R. N. and S. Benita, "Self-emulsifying drug delivery systems (SEDDS) for improved oral delivery of lipophilic drugs," Biomed and Pharacol 58:173-182 (2004).
Kolliphor PS grades—Polysorbates. Technical Information. Issued Mar. 2016, 12 pages.
Kuwano et al., "Cyclosporine a Formulation Affects Its Ocular Distribution in Rabbits," Pharmaceutical Research 19(1):108-111 (2002).

(Continued)

*Primary Examiner* — Theodore R. Howell
(74) *Attorney, Agent, or Firm* — Dentons US LLP; Stephanie Seidman

(57) ABSTRACT

Provided are oil-in-water microemulsions for formulating pharmaceutically active compounds. The microemulsions contain oils, surfactants, water, and the pharmaceutical compounds, and are produced by mixing an aqueous phase and a lipid phase in which each phase contains at least one surfactant in a defined ratio whereby the resulting microemulsion has very small dispersed particles, and, is thermodynamically very stable.

36 Claims, 40 Drawing Sheets

(56) References Cited

FOREIGN PATENT DOCUMENTS

| WO | WO 2003/092706 | 11/2003 |
|---|---|---|
| WO | WO 2007/108031 | 9/2007 |
| WO | WO 2008/119401 | 10/2008 |
| WO | WO 2008/136034 | 11/2008 |
| WO | WO 2009/084021 | 7/2009 |
| WO | WO 2010/093523 | 8/2010 |
| WO | WO 2010/141591 | 12/2010 |

OTHER PUBLICATIONS

Lallemand et al., "Cyclosporine A delivery to the eye: A pharmaceutical challenge," Eur J. Pharm Biopharm 56:307-318 (2003).

Radomska-Soukharev, A. and J. Wojciechowska, "Microemulsions as Potential Ocular Drug Delivery Systems: Phase Diagrams and Physical Properties Depending on Ingredients," Acta Poloniae Pharmaceutica-Drug Research 62(6): 465-471 (2005).

Sakai et al., "Stability of latanoprost in an ophthalmic lipid emulsion using polyvinyl alcohol," Int. J. Pharm 305:176-179 (2005).

Sigward et al., "Formulation and cytotoxicity evaluation of new self-emulsifying multiple W/O/W nanoemulsions," Int. J. Nanomedicine 8:611-625 (2013).

Bhatt et al., "Formulation Development of Egg Albumin & Pluronic F68 based multiple emulsion containing water soluble drug," presented at 64th Indian Pharmaceutical Congress held at Chennai on Dec. 7-9, 2012 [poster], 1 page.

Papa et al., ARVO annual Meeting Abstract entitled "Delivery of Dexamethasone to the Posterior Segment of the Eye Using an Eye Gel Formulation," IOVS 53(14): 471 (2012), 2 pages.

News Release, SIFI S.p.A. entitled "Knight Therapeutics and SIFI S.p.A. Announce Approval of NETILDEX® in Canada," published on Oct. 23, 2019, [online]. Retrieved from <URL:sifigroup.com/dettnews-Knight_Therapeutics_and_SIFI_S.p.A._Announce_Approval_of_NETILDEX%C2%AE in_Canada/442_27/eng/ [retrieved on Dec. 6, 2019], 2 pages.

Letter/Written Disclosure of the Supplemental Information Disclosure Statement for the above-referenced application, filed herewith on Mar. 9, 2020, 2 pages.

Ammar et al., "Nanoemulsion as a Potential Ophthalmic Delivery System for Dorzolamide Hydrochloride," AAPS PharmaSciTech 10(3): 808-819 (2009).

Morsi et al., "Nanoemulsion-based electrolyte triggered in situ gel for ocular delivery of acetazolamide," Eur J Pharm Sci 104(19):302-314 (2017).

International Search Report and Written Opinion, dated Feb. 13, 2020, in connection with International Patent Application No. PCT/IT2019/000048, 15 pages.

* cited by examiner

Western blot analysis in STZ rat retina

MICROEMULSION COMPOSITIONS

RELATED APPLICATIONS

This application is a continuation of International PCT application No. PCT/IT2019/000048, entitled "Microemulsion Compositions," filed Jun. 11, 2019, to inventors Elena Solfato, Ilenia Abbate, Cristina Maria Concetta Zappulla, Manuela Santonocito, Santa Viola, Sandro De Falco, and Francesco Giuliano, and Applicants SIFI S.p.A. and Consiglio Nazionale delle Ricerche. The subject matter of this application is incorporated by reference in its entirety.

FIELD

Provided are oil-in-water microemulsions for formulating pharmaceutical compositions. The microemulsions contain dispersed particles of a size <30 nm. The microemulsions are advantageous for ophthalmic indications.

BACKGROUND

Pharmaceutically active substances useful for therapeutic applications generally are poorly soluble as well as unstable in aqueous solutions. Often these substances have been formulated in emulsions. One of the first examples of exploiting microemulsions for producing supply systems for poorly soluble active ingredients in the field of ophthalmology is represented by the work of Siebenbrodt and Keipert (Siebenbrodt I, Keipert S, Poloxamer-Systems as Potential Ophthalmics—II. Microemulsions, *Eur. J. Pharm. Biopharm,* 1993, 39:25-30). The authors studied microemulsions based on a nonionic polymeric surfactant (poloxamer) and propylene glycol as a co-surfactant in a triacetin solution, with poorly water-soluble ingredients, such as active ingredients (indomethacin, diclofenac sodium and chloramphenicol) and water, obtaining spontaneous stable microemulsions, for surfactant concentrations of 15% and concentrations of propylene glycol of 40%.

Many emulsions, however, are not stable and/or have low bioavailability of the active substances. Formulations of active substances that are characterized by chemical stability, biological safety, and advantageous bioavailability profiles are needed.

SUMMARY

Provided are oil-in-water microemulsions for formulating pharmaceutically active compounds, particularly those with low aqueous solubility. The emulsions, which can be formulated for administration via a variety of routes and for a variety of uses, are particularly advantageous for ophthalmic applications. Also provided are the emulsions containing pharmacologically active ingredients. The microemulsions provided herein have elevated stability, which allows long-term preservation, including at room temperature. Where the incorporated active ingredient is relatively unstable, the formulation in the microemulsion allows its structural integrity to be prolonged in time. The emulsions herein not only have enhanced stability, but also confer enhanced bioavailability of poorly water-soluble drugs in a liquid dosage form.

Hence, provided are microemulsions for administration of any pharmaceutically active compound, particularly those not soluble in aqueous compositions. The microemulsions can be prepared to be administered by any route, including oral and parenteral, and are particularly suited for administration of active compounds to the eye, and include ophthalmic compounds, for treatment of disorders, such as dry eye and age-related macular degeneration (AMD). The microemulsions are prepared by combining particular ratios of surfactants in the aqueous and lipid (lipophilic) phases, generally, but not limited to, two surfactants (a surfactant and co-surfactants) in each phase. When the aqueous and lipophilic phases are combined, the resulting microemulsion forms. The resulting microemulsion has very small particles, less than 30 nm on average, generally less than or equal to 15 nm, and a very narrow distribution of particle sizes, generally about 15±10 nm. Among the resulting properties of the emulsions are increased thermal stability and high bioavailability of any agent formulated in the emulsions compared to similar emulsions in the prior art.

Microemulsions provided herein are produced from: a lipid phase containing an oily (oil) component and surfactant(s) and co-surfactants(s); and an aqueous phase, also containing surfactant(s) and co-surfactants(s). To achieve the advantageous properties, including the small particle size, the following criteria are required:

1) when forming the microemulsions, the weight/volume ratio between the surfactants/co-surfactants in the lipid phase and the surfactants/co-surfactants in the aqueous phase, is from 2 to 10, such as 2.2 to 9.8 or 2.4 to 8.6; and 2) the weight/volume ratio between the oily (oil) component of the lipid phase and the surfactants/co-surfactants in the aqueous phase is from 0.2 to 1.0, such as 0.22 to 0.98 or 0.24 to 0.96; and 3) in the lipid phase, the weight/volume ratio between the oily (oil) component and the mixture of the surfactants/co-surfactants in the lipid phase is from 0.05 to 1.4, such as 0.07 to 1.2 or 0.1 to 1.

When at least 1) and 2) of these criteria are met, the resulting microemulsion exhibits the advantageous properties, including the small particle size and the resulting high thermodynamic stability.

The microemulsions are used for formulating active substances, such as active small molecule drugs, for ophthalmic indications. The microemulsions also can be used to formulate active substances for oral administration or other routes of administration.

The surfactants/co-surfactants all can be the same, so that the resulting microemulsion contains a single surfactant. Generally, however, in preparing the microemulsions, each phase will contain at least one surfactant, and one co-surfactant that is different from the surfactant. Both phases can contain the same surfactant and co-surfactant so that the resulting microemulsion has one surfactant and one co-surfactant. In other embodiments, two or three of the surfactants/co-surfactants can be the same in the lipid phase and aqueous phase, so that the resulting microemulsion contains two or three different surfactants, or all can be different, so the resulting microemulsion contains four different surfactants. The microemulsions can contain more than one surfactants and one co-surfactants in either phase when producing the microemulsions. Thus, two or three of the surfactants/co-surfactants can be the same in the lipid phase and aqueous phase, so that the resulting microemulsion contains two or three different surfactants, or all can be different, so the resulting microemulsion contains four different surfactants. The microemulsions can contain more than two surfactants/co-surfactants in either phase when producing the microemulsions.

The surfactant(s)/co-surfactant(s) can be different for the two phases so that, in a first instance, the resulting microemulsion can contain a minimum of one co-surfactant, the same for both phases, and a different surfactant for each of the two phases. In a second instance the lipid phase can contain two different surfactants, one of which can be the same as the one contained in the aqueous phase. Thus, for example the component surfactants and co-surfactants can be:

| Instance | Surfactant | Co-surfactant | Phase |
|---|---|---|---|
| 1 | S1 | | COS | Lipidic |
| | — | S2 | COS | Aqueous |
| 2 | S1 | S2 | COS | Lipidic |
| | — | S2 | COS | Aqueous |

See also Table 1 below.

To produce the microemulsions with the properties described herein, the amounts of surfactant and co-surfactant must adhere to the ratios as described herein. It is the recited ratios, particularly 1) and 2), as set forth above, that result in a microemulsion with the advantageous properties, including small particle size and narrow particle size distribution. The surfactants/co-surfactants generally are nonionic surfactants that are biocompatible and amenable to introduction into the eye.

In an exemplary embodiment, the microemulsion is composed of 0.4-4.0% (w/v) of an oily component, such as a natural vegetable oil, from the lipid phase, surfactants/co-surfactants from the lipid phase of 4.0%-36.0% (w/v) of the resulting microemulsion, and surfactants/co-surfactants from the aqueous phase of 1.66%-4.15% (w/v) of the resulting microemulsion. The remaining components of the composition are polar or aqueous ingredients, such as water, an active compound(s), and other components included in pharmaceutical compositions, such as thickeners, such as gums, tonicity adjusters, and a biocompatible acid to adjust the pH to about or between 5.0 and 8, inclusive, such as pH 5.4 or 7.5, or 6 to 7. The active ingredient can be included up to about 5% w/v (from 0.001 mg/ml to 50 mg/ml) of the resulting microemulsion.

Provided are pharmaceutical compositions that are microemulsions and contain active ingredients, such as a pharmaceutical agent that is poorly soluble in aqueous medium. The pharmaceutically active compounds include those for ophthalmic use. The amount of active compound depends upon the compound, and indication for which it is used. Exemplary of the range is 0.001 mg/ml to 50 mg/ml, or 0.01 mg/ml to 50 mg/ml, such as 0.01 mg/ml to 30 mg/ml.

The pharmaceutical composition contains: a) a lipid phase comprising an oily component and one or more surfactant(s) and, one or more co-surfactant(s), and b) an aqueous phase comprising one or more surfactant(s), and one or more co-surfactants, where: the weight/volume ratio between the amount of surfactant and co-surfactant in the lipid phase to the amount of surfactant and co-surfactant in the aqueous phase is from 2 to 10; the weight/volume ratio between the amount of oil component in the lipid phase to the amount of surfactant(s) and co-surfactant(s) in the aqueous phase is from 0.2 to 1.0; and in the resulting oil-in-water microemulsion, the average particle size is less than 30 nm. The composition optionally contains active ingredient, such as an active ingredient for ophthalmic use. By virtue of the ratios and the surfactant(s)/co-surfactant(s) in each phase, the resulting microemulsion composition has a narrow size distribution; generally the size distribution of particles in the resulting microemulsion is 15 nm±10 nm. The polydispersity index (PDI) is within the range 0.02-0.380, inclusive, or 0.02 to 0.2, inclusive, or 0.02 to 0.15, inclusive, or is less than 0.2 or less than 0.12 or less than 0.1. In some embodiments, the weight/volume ratio between the amount of surfactant and co-surfactant in the lipid phase to the amount of surfactant and co-surfactant in the aqueous phase is 2.2 to 9.8, inclusive, or 2.4 to 8.6, inclusive. In some embodiments, the weight/volume ratio between the amount of oil component in the lipid phase to the amount of surfactant(s) and co-surfactant(s) in the aqueous phase is from 0.22 to 0.98, inclusive or from 0.24 to 0.96, inclusive. In some embodiments, the weight/volume ratio between the oily component and the surfactant(s) and co-surfactant(s) is from 0.05 to 1.4, inclusive, such as, for example, from 0.07 to 1.2, inclusive, or from 0.1 to 1, inclusive.

Exemplary of these microemulsion compositions is one that contains: an oil component in an amount that is between 0.4%-4.0% (w/v), inclusive, of the composition; surfactant(s) and co-surfactant(s) of the lipid phase in an amount that is between 4.0%-36.0% (w/v), inclusive, of the composition; and surfactant(s) and co-surfactant(s) of the aqueous phase in an amount that is between 1.66%-4.15% (w/v), inclusive, of the composition.

Provided are oil-in-water microemulsion compositions, comprising: an oil component in an amount of 0.4-4.0% weight/volume (w/v) of the composition; a surfactant or a mixture of a surfactant(s) and co-surfactants(s) in an amount of 5.71-40.15% (w/v), inclusive, of the composition; an aqueous component that is in an amount between 55.85%-93.89% (w/v), inclusive, of the composition; and optionally a pharmaceutically active compound, where: all components of the composition are biocompatible; and the average particle size in the microemulsion composition is less than 30 nm. As above, the distribution of particle size is narrow, generally 15 nm±10 nm. The polydispersity index (PDI) is within the range 0.02-0.380, inclusive, or 0.02 to 0.2, inclusive, or 0.02 to 0.15, inclusive, or is less than 0.2 or less than 0.12 or less than 0.1. The oil-in-water microemulsions can contain a pharmaceutically active compound. The amount of pharmaceutically active compound can depend upon the compound and indication for which it is intended. Generally, the concentration is 0.001 mg/ml to 50 mg/ml, or 0.01 mg/ml to 50 mg/ml, or 0.01 mg to 50 mg/ml, such as 0.01 mg/ml to 30 mg/ml.

The oil-in-water microemulsion compositions are formed from: a lipid phase comprising the oily component, and one or more surfactant(s), and optionally one or more co-surfactants(s); and an aqueous phase comprising one or more surfactant(s), and one or more co-surfactants(s), where: the weight/volume ratio between surfactant(s) and co-surfactants(s) in the lipid phase to surfactant(s) and co-surfactants(s) in the aqueous phase is from 2 to 10, inclusive; and the weight/volume ratio between the oily component of the lipid phase and the surfactant(s) and co-surfactants in the aqueous phase is from 0.2 to 1.0, inclusive. In some embodiments, the weight/volume ratio between surfactant(s) and co-surfactants(s) in the lipid phase to the surfactant(s) and co-surfactants(s) in the aqueous phase is 2.2 to 9.8, inclusive, or 2.4 to 8.6, inclusive; and the weight/volume ratio between the oily component in the lipid phase and the surfactant(s) and co-surfactants in the aqueous phase is from 0.22 to 0.98, inclusive, or from 0.24 to 0.96, inclusive. In other embodiments, in the lipid phase, the weight/volume ratio between the oily component and the surfactant(s) and co-surfactants(s) is from 0.05 to 1.4, inclusive, such as, for example, from 0.07 to 1.2, inclusive, or from 0.1 to 1, inclusive. Generally each phase contains one surfactant and one co-surfactant. Upon mixing in the ratios described herein, they form a microemulsion in which the average particle size is less than 30 nm. Generally the particles have a narrow size distribution of 15 nm±10 nm. The resulting microemulsions have a polydispersity index (PDI) generally within the range 0.02-0.380, inclusive, or 0.02 to 0.2, inclusive, or 0.02 to 0.15, inclusive, or is less than 0.2 or less than 0.12 or less than 0.1. Compositions provided herein include those where the micellar dimension of the dispersed phase particles is approximately or is 15±10 nm; and the polydispersity index (PDI) is within the range 0.02-0.380, inclusive, or 0.02 to 0.2, inclusive, or 0.02 to 0.15, inclusive, or is less than 0.380, or is less than 0.2 or less than 0.12 or less than 0.1.

All of the compositions provided herein can be used for formulation of pharmaceutical agents for treatment of diseases and disorders, such as ophthalmic conditions or disorders. For ophthalmic use, the ingredients should be selected to be compatible with or suitable for administration to the eye. In the compositions, each of the surfactant(s) and/or co-surfactant(s) can be nonionic. In all of the compositions the HLB of each of the surfactants and co-surfactants can be between 8-16, inclusive, such as where the HLB of each of the surfactants and co-surfactants is at least 10, such as 10-16, or 12-14. In some embodiments, the compositions contain one surfactant and a co-surfactant, or two surfactants and one co-surfactant, or two surfactants and two co-surfactants. In some embodiments, the compositions are formed from a lipid and aqueous phase in which the surfactant is the same so that the resulting microemulsion contains one surfactant, and generally one or two co-surfactants. In other embodiments, the surfactant in each phase is different. In some embodiments, the compositions are formed from a lipid and aqueous phase in which the aqueous phase contains a surfactant and a co-surfactant, and the lipid phase contains a surfactant and a co-surfactant. The co-surfactant in each phase can be the same or different.

In general, each phase from which the microemulsion is formed contains one surfactant and one co-surfactant. The surfactants and co-surfactants can be the same or different. For example, in one embodiment the lipid phase contains Tween 80/propylene glycol as the surfactant/co-surfactant, and the aqueous phase contains Kolliphor RH40/propylene glycol.

Surfactants can be selected from among, for example, poloxamers, PEGylated fatty acids, polyoxyethylene sorbitan fatty acid derivatives, polyoxyethylenes, hydrogenated castor oil ethoxylates, glycerol esters of fatty acids, polyoxyl castor oil surfactants, amine oxides, and alcohol ethoxylates (nonionic). Exemplary of these are polyethylene glycol sorbitan monolaurate (polysorbate 20; TWEEN 20), polyethylene glycol sorbitan monooleate (polysorbate 80; TWEEN 80), and polyethylene glycol sorbitan monopalmitate (polysorbate 40; MONTANOX 40. In other embodiments the surfactants are selected from among polyoxyl 35 castor oil (CREMOPHOR EL, KOLLIPHOR EL), polyoxyl 40 hydrogenated castor oil (CREMOPHOR RH40; KOLLIPHOR RH 40), PEG 40 castor oil (ETOCAS 40), PEG-60 hydrogenated castor oil (CRODURET 60), and polyethylene glycol 15-hydroxystearate (KOLLIPHOR HS 15).

The surfactants can be nonionic. For example, nonionic surfactants can be selected from among Pluronic®, Cremophor®, Kolliphor®, Polysorbates (Tween™), lauryl dimethyl ammine oxide, polyethoxylated alcohol, polyoxyl lauryl ether, Brij®, polyoxyethylated castor oil, lecithin, poloxamers, polyethylene glycol, glycerol esters of fatty acids. In some embodiments the surfactants are selected from among castor oil or hydrogenated castor oil ethoxylates. Co-surfactants include glycerol and/or propylene glycol. For example, each phase can include the same or different co-surfactant.

The lipid phase contains an oil, which can be selected from among one or more of vegetable or animal oils or synthetic mineral oils. In some embodiments the oils are vegetable or animal oils selected from among soya oil, corn oil, linseed oil, sunflower seed oil, krill oil, cod-liver oil, fish oil, avocado oil, almond oil, babassu oil, borage oil, carob oil, cashew nut oil, grapeseed oil, coconut oil, *Oryza sativa* bran oil, castor oil, hemp seed oil, jojoba oil, peanut oil, poppy seed oil, sesame oil, walnut oil, olive oil, wheat-germ oil, argan oil, cottonseed oil, blackcurrant seed oil, and oils rich in PUFAs by a fraction greater than 10%. In other embodiments the oil can be a mineral oil of synthetic origin selected from esters of medium and long-chain fatty acids, and medium and long-chain triglycerides.

Other ingredients in the compositions include one or more of an isotonizing (tonicity) agent, stabilizing agent, anti-oxidant, anti-microbial, thickening agent, and branched and linear polymers.

The compositions can contain one or more pharmaceutically active ingredients. The one or more active ingredients are present at a suitable concentration for use or storage. Concentration ranges include, but are not limited to, from 0.01 to 50 mg/ml, inclusive, or 0.01 to 30 mg/ml.

The compositions can be formulated with the pharmaceutically active ingredient, in the lipid phase, if the ingredient is non-polar, or in the aqueous phase, if it is polar. Exemplary of the pharmaceutically active ingredients are one or more gastrointestinal agents, antispasmodics, blood sugar regulators, nutraceuticals/minerals/electrolytes, platelet modifying agents, coagulants, cardiovascular agents, alpha-adrenergic agonists/alpha-adrenergic antagonists/vasodilators/arterial vasodilators, carbonic anhydrase inhibitor diuretics/loop diuretics/potassium-sparing diuretics/thiazide diuretics, other cardiovascular agents, beta-adrenergic antagonists, calcium channel blockers, angiotensin converting enzyme inhibitors (ACE), dyslipidemics/HMG CoA Reductase inhibitors (Statins), anti-fungals, dermatological agents, anti-histamines, anesthetics, anti-bacterials, hormone-stimulating agents/substituents/modifiers (adrenals, pituitary and sex hormones), glycemic agents, hormone-suppressing agents (parathyroids), anti-mycobacterials, anti-virals, anti-neoplastics, immunomodulators, anti-inflammatory agents, analgesics, anti-convulsants, anti-Parkinson agents, anti-psychotics, anti-depressants/anti-dementia agents/anti-anxiety medication, anti-myasthenic agents/agents for treating substances of abuse/central nervous system agents, bronchodilators/sympathomimetics/anti-cholinergics/inhaled corticosteroids/phosphodiesterase inhibitors/airborne disorders, other agents of the respiratory tract, anti-parasites, anti-glaucoma ophthalmic agents, other ophthalmic agents/anti-allergic ophthalmic agents, ophthalmic anti-inflammatories, prostaglandin analogues and ophthalmic prostamides, drugs for acidity-related disorders (A02), drugs for gastrointestinal function disorders (A03), drugs used for diabetes (A10), vitamins (A11), mineral supplements (A12), antithrombotic agents (B01), anti-hemorrhagics (B02), cardiac therapy drugs (C01), anti-hypertensives (C02), diuretics (C03), peripheral vasodilators (C04), vasoprotectives (C05), beta-blocking agents (C07), calcium-antagonists (C08), drugs acting on the renin-angiotensin system (C09), lipid-lowering drugs (C10), anti-fungals for dermatological use (D01), emollients and protectives (D02), drugs for injuries and ulcers (D03), antipruritics, including anti-histamines, anaesthetics (D04), anti-psoriasis drugs (DOS), antibiotics and chemotherapeutic agents for dermatological use (D06), antiseptics and disinfectants (D08), hyphophyseal, hypothalamic hormones and similar (H01), systemic corticosteroids (H02), thyroid therapy (H03), pancreatic hormones (H04), homeostatic calcium (HOS), antibacterials for systemic use (J01), anti-mycotics for systemic use (J02), anti-mycobacterials (J04), anti-viral drugs for systemic use (J05), immune serums and immunoglobulins (J06), anti-neoplastic agents (L01), endocrine therapy (L02), immunostimulants (L03), immunosuppressants (L04), anti-inflammatories and anti-rheumatics (M01), topical products for joint and muscle pain (M02), anesthetics (N01), analgesics (N02), anti-epileptics (N03), anti-parkinsonians (N04), psycholeptics (N05), psychoanaleptics (N06), other nervous system drugs (N07), rhinologic preparations (R01), preparations for the pharyngeal cavity (R02), drugs for obstructive disorders of the respiratory tract (R03), preparations for coughs and colds (R05), anti-histamines for systemic use (R06), other preparations for the respiratory system (R07), anti-infectives (S01A), anti-inflammatory agents (S01B), anti-inflammatory agents and anti-infectives combined (S01C), anti-glaucoma agents and miotics (S01E), mydriatics and cyclopegics (S01F), decongestants and anti-allergens (S01G), local anaesthetics (S01H), diagnostic agents (S01J), surgical aids (S01K), ocular vascular agents (S01L), anti-infectives (S03A), corticosteroids (S03B), and corticosteroids combined with anti-infectives (S03C).

In particular embodiments the compositions are formulated for ophthalmic administration, and contain one or more active ingredients for treating ophthalmic conditions or disorders. Such conditions and disorders, include, but are not limited to, dry eye, macular degeneration, glaucoma, infection, inflammation, allergy and diabetic retinopathy. Exemplary of the pharmaceutically active agents is a prostaglandin inhibitor, an anti-angiogenic, and/or an anti-oxidant. Such agents include, a prostaglandin inhibitor selected from among latanoprost, travoprost, bimatoprost, unoprostone, and pharmaceutically acceptable derivatives, hydrates, solvates, metabolites and salts thereof, or a polymorphic crystalline form thereof, and/or an anti-angiogenic agent selected from among sorafenib, sorafenib tosylate, regorafenib, regorafenib tosylate, regorafenib isethionate, regorafenib, ethylsulfonate apremilast, radotinib, spironolactone, and pharmaceutically acceptable derivatives, hydrates, solvates, metabolites and salts thereof, or a polymorphic crystalline form thereof; and/or an anti-oxidant selected from among nordihydroguaiaretic acid, meso-nordihydroguaiaretic (masoprocol) and pharmaceutically acceptable derivatives, hydrates, solvates, metabolites and salts thereof, or a polymorphic crystalline form thereof.

The compositions can be used for methods of treatment of diseases and disorders by administering the composition by a suitable route. The compositions provided herein can be used for treating ophthalmic disorders. Provided are methods of treatment of an ophthalmic disorder by administering a composition to the eye. Ophthalmic disorders or conditions, include, but are not limited to, dry eye, macular degeneration, glaucoma, infection, inflammation, allergy and diabetic retinopathy. Pharmaceutical agents for such uses include, for example, masoprocol, sorafenib tosylate, and latanoprost.

Methods for preparing the microemulsion compositions are provided. One method includes the steps of: a) preparing the lipid phase, where a mixture of surfactants/co-surfactants is solubilized in oil, mixing from 1 to 10 parts of the mixture for each oil part; b) preparing the aqueous phase, where one or more of a surfactant and/or co-surfactants is solubilized in water; c) titrating the lipid phase with the aqueous phase to obtain microemulsion, where: 0.4%-4.0% (w/v) of the microemulsion is composed of the oil component of the lipid phase; 4.0%-36.0% (w/v) of the microemulsion is composed of the surfactants/co-surfactants of the lipid phase; and 1.66%-4.15% (w/v) of the total surfactants/co-surfactants are the surfactants/co-surfactants of the aqueous phase. In another method the steps include: a) preparing the lipid phase, which can include a pharmaceutically active agent, and in which a mixture of surfactants/co-surfactants is solubilized in oil, mixing from 1 to 10 parts of the mixture for each oil part; b) preparing the aqueous phase, where one or more of a surfactant and/or co-surfactants is solubilized in water; c) titrating the lipid phase with the aqueous phase to obtain a microemulsion, where: 0.4-4.0% (w/v) of the microemulsion is composed of the oily component of the lipid phase; 4.0%-36.0% (w/v) of the microemulsion is composed of the surfactants/co-surfactants of the lipid phase, and 1.66%-4.15% (w/v) of the microemulsion is composed of surfactants/co-surfactants of the aqueous phase. The pharmaceutically active agent is included in an amount of at or about 0.001 mg/ml to 50 mg/ml, or 0.01 mg/ml to 50 mg/ml, such as 0.01 mg/ml to 30 mg/ml of the final composition.

Pharmaceutically active agents included or added to the compositions include any suitable for treatment of a particular disorder, including any listed herein above and below. In accord with the methods, titration rate is described by the following equation: $V_{tit}=k \times (v_{tot}/1000 \, ml)$, where $V_{tit}$=titration speed in ml×min−1, k=2 ml×min−1, and $V_{tot}$=total volume of the formulation in ml. The resulting microemulsion compositions are those in which the dispersed particles in the resulting microemulsion have an average size s 30 nm, generally a size distribution of the particles is 15 nm±10 nm, and/or a polydispersity index (PDI) is less than 0.380, or is within the range of 0.01-0.380, inclusive, or 0.01-0.20, inclusive, or 0.01 to 0.15, inclusive, or less than 0.2 or 0.1. Provided are microemulsion compositions prepared by any of the methods described above or below.

In other methods, the microemulsion compositions are prepared by a method that includes: a) preparing a lipid phase comprising an oil component and one or more surfactant(s) and, one or more co-surfactant(s), and b) an aqueous phase comprising one or more surfactant(s), and one or more co-surfactants, where: the weight/volume ratio between the amount of surfactant and co-surfactant in the lipid phase to the amount of surfactant and co-surfactant in the aqueous phase is from 2 to 10; the weight/volume ratio between the amount of oil component in the lipid phase to the amount of surfactant(s) and co-surfactant(s) in the aqueous phase is from 0.2 to 1.0; and, then c) combining the lipid phase with the aqueous phase to form an oil-in-water microemulsion in which the average particle size is less than 30 nm. Step c) can be effected by titrating the lipid phase with the aqueous phase, where the titration rate is described by the following equation: $V_{tit}=k \times (v_{tot}/1000 \, ml)$, where $V_{tit}$=titration speed in ml×min−1, k=2 ml×min−1, and $V_{tot}$=total volume of the formulation in ml.

In these methods, the weight/volume ratio between the amount of surfactant and co-surfactant in the lipid phase to the amount of surfactant and co-surfactant in the aqueous phase is 2.2 to 9.8, inclusive, or 2.4 to 8.6, inclusive.

The aqueous phase can contain one surfactant and one co-surfactant. In some embodiments the weight/volume ratio between the amount of oil component in the lipid phase to the amount of surfactant(s) and co-surfactant(s) in the aqueous phase is from 0.22 to 0.98, inclusive or from 0.24 to 0.96, inclusive. In other embodiments, in the lipid phase, the weight/volume ratio between the oily component and the surfactant(s) and co-surfactant(s) is from 0.05 to 1.4, inclusive. In other embodiments in the lipid phase, the weight/volume ratio between the oily component and the surfactant(s) and co-surfactant(s) is from 0.07 to 1.2, inclusive, or from 0.1 to 1, inclusive. The size distribution of particles in the resulting microemulsion generally is 15 nm±10 nm, and the polydispersity index (PDI) is within the range 0.02-0.380, inclusive, or 0.02 to 0.2, inclusive, or 0.02 to 0.15, inclusive, or is less than 0.2 or less than 0.12 or less than 0.1. Microemulsion compositions prepared by any of the methods described herein are provided.

BRIEF DESCRIPTION OF THE DRAWINGS

FIG. 3A shows the pH data. FIG. 3B depicts the osmolality. FIG. 3C depicts the average particle distribution (size). FIG. 3D depicts the Zeta potential (pZ).

FIG. 4A depicts the average particle distribution diagram for formulation 1-(A). FIG. 4B depicts the average particle distribution diagram for formulation 5-(B).

FIG. 5A shows the osmolality data. FIG. 5B depicts the pH data. FIG. 5C depicts the average particle distribution (size). FIG. 5D depicts the Zeta potential (pZ).

FIG. 6A depicts the stability data at 25° C. FIG. 6B depicts the stability data at 40° C. FIG. 6C depicts the stability data at 60° C.

FIG. 7A shows the pH data. FIG. 7B depicts the average particle distribution (size). FIG. 7C depicts the polydispersity index (PDI). FIG. 7D depicts the Zeta potential (pZ).

FIG. 8A shows the pH data. FIG. 8B depicts the average particle size (size). FIG. 8C depicts the polydispersity index (PDI). FIG. 8D depicts the osmolality. FIG. 8E depicts the Zeta potential (pZ).

FIG. 9A shows the pH data. FIG. 9B depicts the osmolality. FIG. 9C depicts the average particle distribution (size). FIG. 9D depicts the Zeta potential (pZ). FIG. 9E depicts the recovery.

FIG. 10A shows the pH data. FIG. 10B depicts the osmolality. FIG. 10C depicts the average particle distribution (size). FIG. 10D depicts the Zeta potential (pZ). FIG. 10E depicts the recovery.

FIG. 11A depicts the stability data at 25° C. FIG. 11B depicts the stability data at 40° C. FIG. 11C depicts the stability data at 60° C. FIG. 11D depicts the stability data at 4° C.

FIG. 12A shows the pH data. FIG. 12B depicts the osmolality. FIG. 12C depicts the average particle distribution (size). FIG. 12D depicts the Zeta potential (pZ). FIG. 12E depicts the recovery.

FIG. 13A shows the pH data. FIG. 13B depicts the average particle distribution (size). FIG. 13C depicts the polydispersity index (PDI). FIG. 13D depicts the Zeta potential (pZ). FIG. 13E depicts the recovery.

FIG. 15A depicts the gene expression data after pretreatment with formulation 1 or formulation 04. FIG. 15B depicts the gene expression data after pretreatment with formulation 6 or formulation 06. The data represents the average±SEM of the Fold Change in relation to the calibrator (CTRL NAÏVE). #$p \leq 0.05$, ##$p \leq 0.01$ vs. formulation 1 (FIG. 15A) and formulation 6 (FIG. 15B). *$p \leq 0.05$, ****$p \leq 0.0001$ vs. CTRL NAÏVE (FIG. 15A and FIG. 15B). One-way ANOVA followed by Dunnett's post-hoc test.

FIG. 16A depicts the gene expression data after pretreatment with formulation 2 or formulation 05. FIG. 16B depicts the gene expression data after pretreatment with formulation 7 or formulation 07. The data represents the average±SEM of the Fold Change in relation to the calibrator (CTRL NAÏVE). #$p \leq 0.05$, ##$p \leq 0.01$, ###$p \leq 0.001$ vs. formulation 2 (FIG. 16A) and formulation 7 (FIG. 16B). *$p \leq 0.05$, *$p \leq 0.001$, **$p \leq 0.0001$ vs. CTRL NAIVE (FIG. 16A and FIG. 16B). One-way ANOVA followed by Dunnett's post-hoc test.

FIG. 18A depicts the data after pretreatment with formulation 2 or formulation 05. FIG. 18B depicts the data after pretreatment with formulation 7 or formulation 07. The data is represented as the average±SEM in relation to formulation 2 (FIG. 18A) or 7 (FIG. 18B), respectively. *p=0.0135 vs. formulation 2 (FIG. 18A); *p=0.0001 vs. formulation 7 (FIG. 18B). Images representative of CNV in animals treated with formulation 2, formulation 05, formulation 7 or formulation 07 are shown at a side. The scale bar represents 100 μm.

FIG. 19A depicts the gene expression of TNFa. FIG. 19B depicts the gene expression of NFκB. FIG. 19C depicts the gene expression of IGF1. FIG. 19D depicts the gene expression of IGFR1. FIG. 19E depicts the gene expression of VEGFR1. FIG. 19F depicts the gene expression VEGFR2. The data represents the average±SEM of the Fold Change in relation to the calibrator (Ctrl). $*p \leq 0.05$, $p \leq 0.01$, $*p \leq 0.001$ vs. Ctrl−. $\#\#\#p \leq 0.001$ vs. STZ. ANOVA followed by Tukey-Kramer's post-hoc test.

FIG. 20A depicts the protein expression of VEGF1R after treatment with microemulsion containing masoprocol 0.302% (formulation 04). FIG. 20B depicts the protein expression of TNFa after treatment with microemulsion containing masoprocol 0.302% (formulation 04). FIG. 20C depicts the protein expression of VEGFR2 after treatment with microemulsion containing masoprocol 0.302% (formulation 04). FIG. 20D depicts a Western blot analysis of TNFa, VEGFR1 and VEGFR2 in Ctrl− rat retinas, diabetic (STZ) and diabetic treated b.i.d. topically for 21 days with microemulsion containing masoprocol 0.302% (formulation 04). FIG. 20E depicts the protein expression of TNFa after treatment with microemulsion containing sorafenib tosylate 0.300% (formulation 05). FIG. 20F depicts the protein expression of VEGFR1 after treatment with microemulsion containing sorafenib tosylate 0.300% (formulation 05). FIG. 20G depicts the protein expression of VEGFR2 after treatment with microemulsion containing sorafenib tosylate 0.300% (formulation 05). FIG. 20H depicts a Western blot analysis of TNFa, VEGFR1 and VEGFR2 in Ctrl− rat retinas, diabetic (STZ) and diabetic treated b.i.d. topically for 21 days with microemulsion containing sorafenib tosylate 0.300% (formulation 05). The data represents the average±SEM. $***p \leq 0.001$ vs Ctrl−. $\#\#p \leq 0.01$, $\#\#\#p \leq 0.001$ vs. STZ. ANOVA followed by Tukey-Kramer's post-hoc test.

DETAILED DESCRIPTION

A. Definitions

Figure 1:
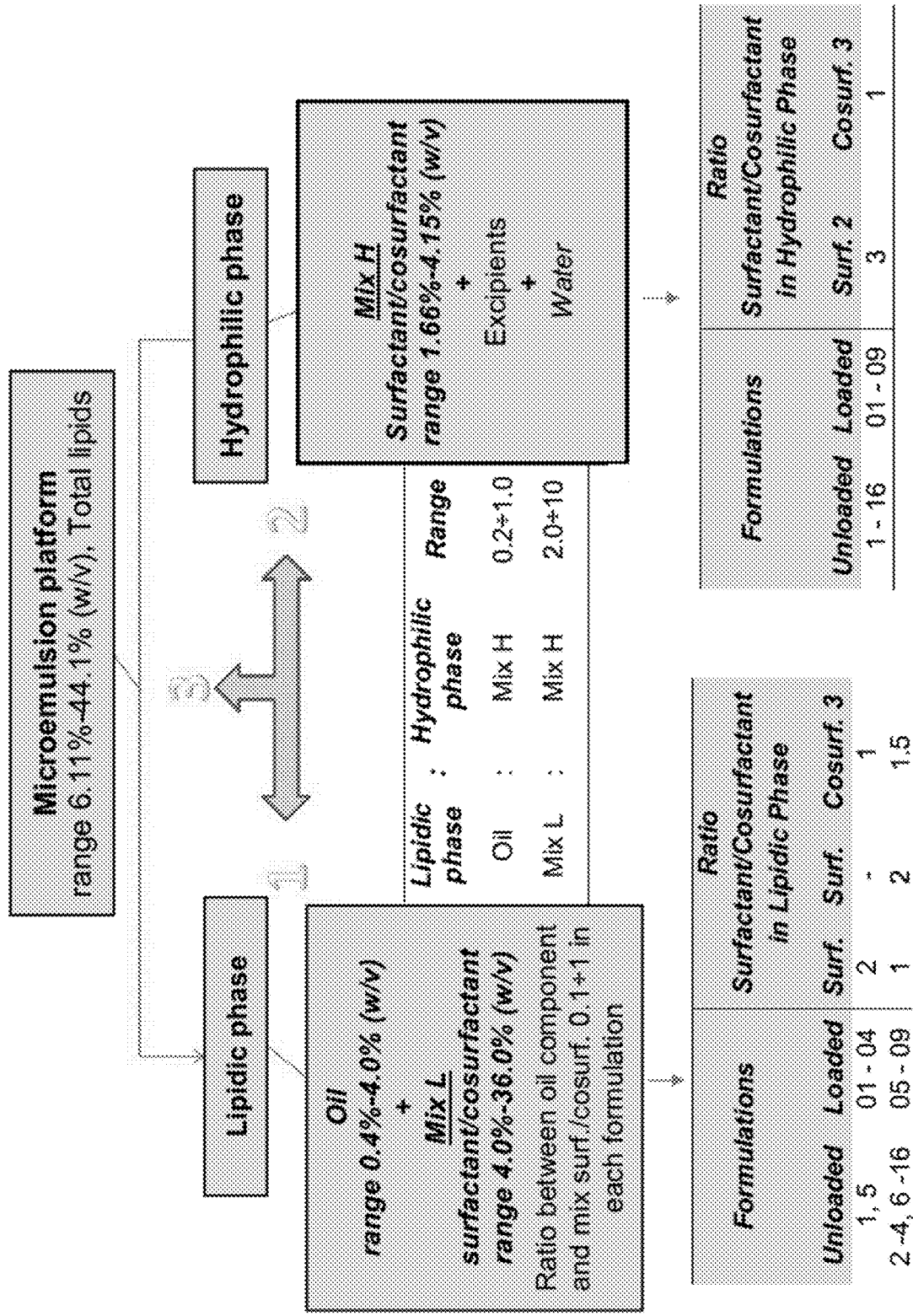
FIG. 1 is a schematic representation of the microemulsion platform provided herein.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference there to evidences the availability and public dissemination of such information.

As used herein, an emulsion is a system composed of two immiscible liquid phases, intimately mixed and dispersed, the one into the other. An emulsion refers to a colloidal dispersion of two immiscible liquids, for example, an oil and water (or other aqueous liquid, e.g., a polar solvent), one of which is part of a continuous phase and the other of which is part of a dispersed phase. The emulsions herein are oil-in-water, which include any oil soluble phase dispersed in any aqueous phase, also called the water phase, in which the oil phase is the dispersed phase and the water phase is the continuous phase. Emulsions typically are stabilized by one or more surfactants and/or co-surfactants and/or emulsion stabilizers. Surfactants form an interfacial film between the oil and water phase of the emulsion, providing stability.

As used herein, a microemulsion is a two-phase systems composed of a lipid phase and an aqueous phase, finely interspersed. Microemulsions are liquid mixtures, transparent, isotropic and stable, of a lipid phase and an aqueous phase, held together by a surfactant, generally in conjunction with a co-surfactant. Microemulsions are clear, thermodynamically stable, isotropic liquid mixtures of oil, water and surfactant, and optionally a co-surfactant. Microemulsions form spontaneously upon mixing of the aqueous phase and lipid phase. A microemulsion is, therefore, a thermodynamically stable system, with particles dispersed in the continuous phase. The droplet size of the dispersed phase in a microemulsion is less than 100 nm, generally in the range between 5 nm and 50 nm, inclusive.

As used herein, "surfactant" refer to synthetic and naturally occurring amphiphilic molecules that have hydrophobic portion(s) and hydrophilic portion(s). Surfactants contain a hydrophilic domain and hydrophobic domain, i.e. amphiphilic molecules. Given their nature, surfactants facilitate the formation of oil-in-water emulsions where the micelles, in order to exist, need to interact with both the water and the oil phases. Due to their amphiphilic (amphipathic) nature, surfactants and co-surfactants can reduce the surface tension between two immiscible liquids, for example, the oil and water phases in an emulsion, such as a microemulsion, stabilizing the emulsion.

Surfactants can be characterized based on their relative hydrophobicity and/or hydrophilicity. For example, relatively lipophilic surfactants are more soluble in fats, oils and waxes, typically having Hydrophobic-Lipophilic Balance (HLB) values less than 10 or about 10, while relatively hydrophilic surfactants are more soluble in aqueous compositions, for example, water, and typically have HLB values greater than 10 or about 10. Relatively amphiphilic surfactants are soluble in oil and water based liquids and typically have HLB values close to 10 or about 10. Surfactants for use in the compositions herein are biocompatible, and have an HLB value between 8 or about 8 and 16 or about 16, generally 10-16, or 12-14.

As used herein, a co-surfactant is a surfactant that acts in addition to another surfactant to further reduce the surface tension of a liquid. Recitation that microemulsions contain surfactants refers to the surfactants and the co-surfactants that are included. Co-surfactants are hydrophilic in nature, and reduce the surface tension of water. They generally are used as wetting agents, for example, to increase the spreading abilities of water-based fluid by reducing the surface tension of water. Cosurfactants also are used, and often needed, to increase the solubility of the primary surfactant.

As used herein, "particle size" and "average particle size" refer synonymously to the average diameter of particles in a provided liquid, for example, the droplet diameter or micelle diameter in an emulsion As used herein, "oil phase" or "lipid phase" is used to refer to the portion (or phase) of a composition such as those provided herein that contains one or more lipophilic ingredients and/or amphiphilic ingredients, such as an oil, and is, in general, the lipid-soluble phase. In an oil-in-water (o/w) microemulsion, the lipid phase typically is the dispersed phase while water is the dispersion phase.

As used herein, oil phase ingredient(s) refers to the components of the provided compositions that are included in the oil phase in the provided methods for making the compositions. Typical oil phase ingredients include non-polar compounds, e.g., non-polar active ingredients; at least one surfactant; oils, such as non-polar solvents; preservatives; and microemulsion stabilizers. Other lipophilic and/or amphiphilic ingredients can be included in the oil phase.

As used herein, "water phase" or "aqueous phase" refers to the portion (phase) of a composition, such as those provided herein, that contains one or more hydrophilic ingredients and/or amphiphilic ingredients (water phase ingredients) and is, in general, the water-soluble phase. Typically, in the microemulsion compositions provided herein, the water phase is the continuous phase. "Water phase" also is used to refer to the liquid containing the water phase ingredients that is generated while preparing microemulsions.

As used herein, water phase ingredient(s) refers to the components of the compositions that are included in the water phase in the provided methods for making the compositions. Typical water phase ingredients can include, but are not limited to, polar solvents, typically polar protic solvents, such as water and alcohols, typically alcohols having more than one hydroxy group such as dihydroxy and trihydroxy alcohols, such as glycerol and propylene glycol; at least one surfactant; preservatives; and emulsion stabilizers. Other hydrophilic and/or amphiphilic ingredients can be included in the water phase.

As used herein, thermodynamic stability of the microemulsions refers to the stability of the dispersion such that the phases do not separate. The microemulsions provided herein exhibit high thermodynamic stability as shown by their stability at elevated temperatures.

As used herein, a subject includes an animal, typically a mammal, typically a human.

As used herein, room temperature and ambient temperature are used to describe a temperature that is common in one or more enclosed spaces in which human beings typically are or reside. Room temperature can vary, but generally refers to temperatures between 19° C. or about 19° C. and 25° C. or about 25° C. When a composition is stored at room temperature, it should be understood it is generally kept at a temperature within this range or about within this range.

As used herein, refrigerated temperature refers to a temperature that is common in a refrigerator, for example, a household or restaurant refrigerator, for example, a temperature that is cooler than room temperature, but typically a few degrees above the freezing point of water (0° C. or about 0° C., or −19° C. or −20° C.). Typically, refrigerated temperatures are between 10° C. or about 10° C. and 0° C. or about 0° C., for example, 4° C. or about 4° C. When a composition is stored at a refrigerated temperature, it should be understood that it is kept at a temperature common to household or industrial refrigerators.

As used herein, frozen temperature refers to a temperature around or below the freezing point of water, e.g., a temperature commonly used in a household freezer, for example, 0° C. or about 0° C., for example, −19° C. or about −19° C. or −20° C. or about −20° C., or colder.

As used herein, the singular forms "a," "an" and "the" include plural referents unless the context dictates otherwise.

As used herein, ranges and amounts can be expressed as "about" a particular value or range. About also includes the exact amount. Hence "about 5 grams" means "about 5 grams" and also "5 grams". It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range, for example, but not limited to, 5.25, 6.72, 8.5, and 11.95 grams.

As used herein, "optional" or "optionally" means that the subsequently described event or circumstance does or does not occur and that the description includes instances where said event or circumstance occurs and instances where it does not. For example, an optionally variant portion means that the portion is variant or non-variant. In another example, an optional ligation step means that the process includes a ligation step or it does not include a ligation step.

As used herein, ranges and amounts can be expressed as "about" a particular value or range. About also includes the exact amount. Hence "about 10%" means "about 10%" and also "10%."

As used herein, "optional" or "optionally" means that the subsequently described event or circumstance or element does or does not occur, and that the description includes instances where said event or circumstance or element occurs and instances where it does not. For example, an optionally substituted group means that the group is unsubstituted or is substituted.

B. Overview

Provided herein are thermodynamically stable microemulsions that can be used to solubilize pharmaceutically active compounds. The microemulsions provided herein, advantageously, can be used for ophthalmic applications. The microemulsions are prepared from: a lipid phase containing an oily component and one or more surfactants and co-surfactants; and an aqueous phase, containing one or more surfactants and co-surfactants. In some embodiments the aqueous phase contains one surfactant and one co-surfactant. Additional ingredients used in emulsions and compositions for pharmaceutical use also can be included.

As described herein the microemulsions provided herein have small particles of relatively uniform size. As a result, the emulsions are very stable and can be used to formulate pharmaceutically active compounds to produce very stable compositions in which the compounds have high bioavailability.

The microemulsions are formed by including an oil in the lipid phase, and at least one surfactant and one co-surfactant in each of the aqueous and lipid phases in precise ratios. When these ratios are used, the microemulsions that form upon mixing the two phases, such as by titrating the lipid phase with the aqueous phase (adding the aqueous phase into the lipid phase), have a very narrow distribution range of very small particles (<30 nm). As a result, the microemulsions are unusually stable, and, can be used to formulate pharmaceutically active compounds that have limited aqueous solubility. The resulting microemulsion compositions, which are very stable, render the pharmaceutical compounds bioavailable.

In particular embodiments, the microemulsions are formed from aqueous and lipid phases in which:
the weight/volume ratio between the amount of surfactant and co-surfactant in the lipid phase to the amount of surfactant and co-surfactant in the aqueous phase is from 2 to 10; and
the weight/volume ratio between the amount of oil component in the lipid phase to the amount of surfactant and co-surfactant in the aqueous phase is from 0.2 to 1.0.

Additionally, in some embodiments, in the lipid phase, the weight/volume ratio between the oily component and the surfactant and co-surfactants is from 0.05 to 1.4, inclusive.

Further details of the components of the microemulsions, including the surfactants, oils, pharmaceutically active compounds, are described herein.

C. Surfactants

For preparing the microemulsions each phase must include at least one surfactant, and generally include a co-surfactant. The surfactant(s) in the lipid and aqueous phases can be the same or different.

The surfactants and co-surfactants used for the lipid phase and for the aqueous phase have a HLB value from 8-16, in particular from 10-16, or 12-14. Any biocompatible surfactant/co-surfactants suitable for pharmaceutical applications and that has an HLB in these ranges can be used in the microemulsions. There are many such surfactants/co-surfactants known to the those of skill in the art (see Tables and discussion below for exemplary surfactants). The skilled person readily can select surfactants and co-surfactants for use in the microemulsions. Selected surfactants will have an HLB within the requisite range, and will be appropriate for the intended application and the active agent. For example, surfactants for ophthalmic use should be suitable for administration to the eye. Surfactants suitable for use in pharmaceutical compositions, include those for ophthalmic application. Such surfactants are well known (see, e.g., U.S. Pat. No. 6,267,985).

Hydrophilic surfactants suitable for use in the microemulsion compositions provided herein include any hydrophilic surfactants known to those of skill in the art that have an HLB between about 8 and 16, inclusive, and generally having an HLB value greater than or equal to 10. Surfactants include, but are not limited to, polyoxyethylene sorbitan fatty acid derivatives, polyoxyethylenes, hydrogenated castor oil ethoxylates, glycerol esters of fatty acids, PEGylated fatty acids, polyoxyl castor oil surfactants, poloxamers, amine oxides, and alcohol ethoxylates (nonionic surfactants). Co-surfactants include glycerol and propylene glycol. Examples include, but are not limited to, polyoxyethylene sorbitan fatty acid derivatives, such as TWEEN 20 (polyethylene glycol sorbitan monolaurate; polysorbate 20; available, for example, from Sigma-Aldrich), TWEEN 80 (polyethylene glycol sorbitan monooleate; polysorbate 80; available from Sigma-Aldrich), and MONTANOX 40 (polyethylene glycol sorbitan monopalmitate; polysorbate 40).

Hydrophilic surfactants having the HLB values include castor oil or hydrogenated castor oil ethoxylates, e.g., CREMOPHOR EL (polyoxyl 35 castor oil USP, available from BASF), CREMOPHOR RH40 (KOLLIPHOR RH 40; polyoxyl 40 hydrogenated castor oil USP, available from BASF), ETOCAS 40 (PEG 40 castor oil, available from Croda), CRODURET 60 (PEG-60 hydrogenated castor oil, available from Croda), and KOLLIPHOR HS 15 (polyethylene glycol 15-hydroxystearate, available from Sigma-Aldrich).

The following table provides generic names and tradenames/trademarks of surfactants, by type, for pharmaceutical applications, including the microemulsions provided herein.

| Trade Name/Trademark | Generic/Chemical Name | HLB |
|---|---|---|
| Class - polyoxyethylene sorbitan fatty acid derivatives | | |
| TWEEN 20, Polysorbate 20 | polyethylene glycol sorbitan monolaurate | 16.7 |
| TWEEN 80, Polysorbate 80 | polyethylene glycol sorbitan monooleate | 15 |
| MONTANOX 40, Polysorbate 40, Tween ® 40 | polyethylene glycol sorbitan monopalmitate | 15.6 |
| TWEEN 60, Polysorbate 60 | Polyoxyethylene sorbitan monostearate | 14.9 |
| Polysorbate 61 | Polyoxyethylene sorbitan monostearate | 9.6 |
| Polysorbate 85 | Polyoxyethylene sorbitan trioleate | 11 |
| | PEG-40 Sorbitan Peroleate | 9 |

-continued

| Trade Name/Trademark | Generic/Chemical Name | HLB |
|---|---|---|
| Class - polyoxyethylenes (BRIJ) | | |
| BRIJ ® L4 | Polyethylene glycol dodecyl ether Polyoxyethylene (4) lauryl ether | 9 |
| BRIJ ® C10 | Polyethylene glycol hexadecyl ether Polyoxyethylene (10) cetyl ether | 12 |
| BRIJ ® S20 | Polyethylene glycol octadecyl ether Polyoxyethylene (10) stearyl ether | 15 |
| BRIJ ® 20 | Polyoxyethylene (20) oleyl ether | 15 |
| BRIJ ® 58 | Polyethylene glycol hexadecyl ether Polyoxyethylene (20) cetyl ether | 16 |
| BRIJ ® L23 | Polyoxyethylene (23) lauryl ether | 16.9 |
| BRIJ ® O20 | Polyoxyethylene (20) oleyl ether | 15 |
| Brij ® O10 (Brij ® 97) | Polyoxyethylene (10) oleyl ether | 12 |
| Brij ® S10 | Polyoxyethylene (10) stearyl ether | 12 |
| Brij ® C10 | Polyoxyethylene (10) cetyl ether | 12 |
| Brij ® S20 | Polyoxyethylene (20) stearyl ether | 15 |
| Brij ® S721 | Polyoxyethylene (21) stearyl ether | 16 |
| Brij ® S 100 | Polyoxyethylene (100) stearyl ether | 18 |
| Brij ® CS17 | Polyoxyethylene linear alkyl ether | 15 |
| Brij ® 58 | Polyoxyethylene (20) cetyl ether | 16 |
| Class - castor oil ethoxylates (ethylene oxide condensates of castor oil) | | |
| ETOCAS 40 | PEG-40 castor oil | 13 |
| EMANON CO-40 | Polyoxyethylene(40) castor oil | 13.9 |
| | PEG-60 castor oil | 16 |
| | PEG-25 castor oil | 11 |
| Class - hydrogenated castor oil ethoxylates (ethylene oxide condensates of hydrogenated castor oil) | | |
| CREMOPHOR RH40, KOLLIPHOR RH 40 | polyoxyl 40 hydrogenated castor oil | 14-16 (closer to 14) |
| CREMOPHOR EL, KOLLIPHOR EL | polyoxyl 35 castor oil | 12-14 |
| EMANON CH-25 | PEG-25 HYDROGENATED CASTOR OIL | 10.7 |
| Cremophor ® RH 40 (Kolliphor ® RH40) | PEG 40 hydrogenated Castor oil | 15-17 |
| Cremophor ® RH 60 CRODURET 60 | PEG 60 hydrogenated Castor oil | 14-16 |
| Class - poloxamers (nonionic tri-block copolymers containing a central hydrophobic chain of poloxypropylene (poly(propylene oxide)) flanked by two hydrophilic chains of polyoxy-ethylene (poly(ethylene oxide)) | | |

Structure:

$$HO{-}{\left[{-}CH_2CH_2{-}O{-}\right]}_a{\left[{-}CH(CH_3)CH_2{-}O{-}\right]}_b{\left[{-}CH_2CH_2{-}O{-}\right]}_a{-}H$$

General structure with a = 2-130 and b = 15-67

| | | |
|---|---|---|
| Pluronic ® L-64 | PEG-PPG-PEG Mn~2,900 | 12-18 |
| Pluronic ® P-123 | PEG-PPG-PEG Mn~5,800 | 7-9 |
| Pluronic ® 10R5 | PEG-PPG-PEG Mn~2,000 | 12-18 |
| Pluronic ® 105 | PEG-PPG-PEG Mn~6,500 | 15 |
| | PEG-PPG-PEG Mn~920 | 10 |
| Class - amine oxides | | |
| AMMONYX ® LO | lauryl dimethyl amine oxide | 15 |
| AMMONYX ® MO | Myristamine oxide (Myristyl dimethylamine oxide) | 14 |
| AMMONYX ® DO | Decylamine oxide | 15 |
| AMMONYX ® LO-A | Lauramine oxide | 15 |
| AMMONYX ® M | Myristylamine/dimethylamine oxide | 16 |
| AROMOX DMHT | Dimethyl hydrogenated tallowalkylamine oxide | 14.4 |
| AROMOX DM16 | Dimethylhexadecylamine oxide | 14.2 |
| Class - polyethoxylated alcohols (contain an oleophilic, carbon-rich, fatty alcohol and a hydrophilic, polyoxyethylene chain.) | | |
| ALKONAT ® CE 50 | Cetearyl Alcohol Ethoxylate 5 EO | 9.2 |
| ALKONAT ® CE 200 | Cetearyl Alcohol Ethoxylate 20 EO | 15.5 |
| ALKONAT ® L 30 | Lauryl Alcohol Ethoxylate 3 EO | 8.3 |
| ALKONAT ® L 40 | Lauryl Alcohol Ethoxylate 4 EO | 9.7 |
| ALKONAT ® L 50 | Lauryl Alcohol Ethoxylate 5 EO | 10.8 |
| ALKONAT ® L 60 | Lauryl Alcohol Ethoxylate 6 EO | 11.7 |

| Trade Name/Trademark | Generic/Chemical Name | HLB |
|---|---|---|
| ALKONAT ® L 120 | Lauryl Alcohol Ethoxylate 12 EO | 14.8 |
| ALKONAT ® E 200 | Stearyl Alcohol Ethoxylate 20 EO | 15.3 |
| ALKOSYNT ® ID 30 | Isodecyl Alcohol Ethoxylate 3 EO | 9.1 |
| ALKOSYNT ® ID 80 | Isodecyl Alcohol Ethoxylate 8 EO | 13.8 |
| ALKOSYNT ® IT 50 | Isotridecyl Alcohol Ethoxylate 5 EO | 10.7 |
| ALKOSYNT ® IT 100 | Isotridecyl Alcohol Ethoxylate 10 EO | 13.9 |
| Class - alcohol ethoxylates (nonionic) | | |
| BIO-SOFT N1-3 | Linear alcohol (C11) ethoxylate, POE-3 | 8.7 |
| BIO-SOFT N1-5 | Linear alcohol (C11) ethoxylate, POE-5 | 11.2 |
| BIO-SOFT N1-7 | Linear alcohol (C11) ethoxylate, POE-7 | 12.9 |
| BIO-SOFT N1-9 | Linear alcohol (C11) ethoxylate, POE-9 | 13.9 |
| BIO-SOFT N23-3 | Linear alcohol (C12-13) ethoxylate, POE-3 | 8.1 |
| BIO-SOFT N23-6.5 | Linear alcohol (C12-13) ethoxylate, POE-5 | 11.9 |
| Class - glycerol esters of fatty acids | | |
| KOLLIPHOR HS 15 | Polyoxyl 15 hydroxystearate | 16 |
| Class - PEGylated fatty acids | | |
| | PEG-40 Sorbitan Hexaoleate | 10 |
| | PEG-40 Sorbitan Perisostearate | 10 |
| | PEG-10 Olive Glycerides | 10 |
| | PEG-7 Glyceryl Cocoate | 10 |
| | PEG sorbitol hexaoleate | 10.2 |
| | PEG-8 Dioleate | 8 |
| | PEG-7 Glyceryl Cocoate | 11 |
| | Cetearyl Glucoside | 11 |
| | PEG-8 Stearate | 11.1 |
| | PEG sorbitan tetraoleate | 11.4 |
| | PEG-15 Glyceryl Isostearate | 11.4 |
| | PEG-400 monooleate | 11.4 |
| | PEG-400 monostearate | 11.6 |
| | PEG-8 Oleate | 11.6 |
| Class - alcohol ethoxylates (nonionic) | | |
| BIO-SOFT N1-3 | Linear alcohol (C11) ethoxylate, POE-3 | 8.7 |
| BIO-SOFT N1-5 | Linear alcohol (C11) ethoxylate, POE-5 | 11.2 |
| BIO-SOFT N1-7 | Linear alcohol (C11) ethoxylate, POE-7 | 12.9 |
| BIO-SOFT N1-9 | Linear alcohol (C11) ethoxylate, POE-9 | 13.9 |
| BIO-SOFT N23-3 | Linear alcohol (C12-13) ethoxylate, POE-3 | 8.1 |
| BIO-SOFT N23-6.5 | Linear alcohol (C12-13) ethoxylate, POE-5 | 11.9 |

Table Exemplary Surfactants and Co-Surfactants for use in the microemulsions

| Surfactant/co-surfactant | HLB |
|---|---|
| PEG-8 Dioleate | 8 |
| Sorbitan Laurate | 8.6 |
| Polyethylene glycol dodecyl ether Polyoxyethylene (4) lauryl ether (BRIJ ® L4) | 9 |
| PEG-40 Sorbitan Peroleate | 9 |
| Polyoxyethylene sorbitan monostearate (Tween 61) | 9.6 |
| Laureth-4 | 9.7 |
| Polysorbate 80 | 10 |
| Polyethylene-block-poly(ethylene glycol) average Mn ~1,400 | 10 |
| Polyoxyethylene (5) nonylphenylether, branched (IGEPAL ® CO-520) | 10 |
| Poly(ethylene glycol) sorbitol hexaoleate | 10 |
| PEG-40 Sorbitan Hexaoleate | 10 |
| PEG-40 Sorbitan Perisostearate | 10 |
| PEG-10 Olive Glycerides | 10 |
| PEG-7 Glyceryl Cocoate | 10 |
| PEG sorbitol hexaoleate | 10.2 |
| Polyoxyethylene sorbitan tristearate (Tween 65) | 10.5 |
| PEG-25 Hydrogenated Castor Oil | 10.8 |
| Polyoxyethylene sorbitan trioleate (Polysorbate 85) | 11 |
| PEG-7 Glyceryl Cocoate | 11 |
| Cetearyl Glucoside | 11 |
| PEG-8 Stearate | 11.1 |
| PEG sorbitan tetraoleate | 11.4 |
| PEG-15 Glyceryl Isostearate | 11.4 |
| PEG-400 monooleate | 11.4 |
| PEG-400 monostearate | 11.6 |
| PEG-8 Oleate | 11.6 |
| Poly(propylene glycol)-block-poly(ethylene glycol)-block-poly(propylene glycol) average Mn ~2,700 (PPG-PEG-PPG Pluronic ® 17R4) | 7-12 |
| Caprylocaproyl Polyoxyl-8 glycerides (Labrasol ®) | 12 |
| PEG-15 Glyceryl Isostearate | 12 |
| PEG-35 Almond Glycerides | 12 |
| Polyglyceryl-3 Methylglucose distearate | 12 |
| Polyethylene glycol hexadecyl ether Polyoxyethylene (10) cetyl ether (BRIJ ® C10) | 12 |
| Oleth-10 | 12.4 |
| Ceth-10 | 12.9 |
| Polyoxyethylene (9) nonylphenylether, branched (IGEPAL ® CO-630) | 13 |
| PEG-8 Laurate | 13 |
| PEG-400 monolaurate | 13.1 |
| Polyoxyethylene sorbitan monolaurate (Tween 21) | 13.3 |
| Polyoxyethylene (12) isooctylphenyl ether Polyoxyethylene (12) octylphenyl ether, branched (IGEPAL ® CA-720) | 14 |
| Polyoxyethylene (12) tridecyl ether | 14 |
| PEG-8 glyceryl caprylate/caprate | 14 |
| PEG-32 glyceryl laurate | 14 |
| Polyethylene glycol sorbitan monostearate Polyoxyethylene sorbitan monostearate (TWEEN ® 60) | 14.9 |

-continued

Table Exemplary Surfactants and Co-Surfactants for use in the microemulsions

| Surfactant/co-surfactant | HLB |
|---|---|
| Polyethylene glycol octadecyl ether Polyoxyethylene (10) stearyl ether (BRIJ ® S20) | 15 |
| Polyoxyethylene sorbitan monooleate (Polysorbate 80) | 15 |
| Polyoxyethylene (18) tridecyl ether | 15 |
| PEG-60 Almond glycerides | 15 |
| Polyoxyethylene (20) oleyl ether (BRIJ ® 20) | 15 |
| PEG-20 glyceryl stearate | 15 |
| PEG-20 stearyl ether | 15.3 |
| PEG-20 oleyl ether | 15.3 |
| Polyoxyethylenesorbitan monopalmitate (TWEEN ® 40) | 15.6 |
| PEG-20 hexadecyl ether | 15.7 |
| Polyethylene glycol hexadecyl ether Polyoxyethylene (20) cetyl ether (BRIJ ® 58) | 16 |
| Polyoxyl 35 castor oil (Macrogolglycerol ricinoleate) (Cremophor EL) | 12-14 |
| Polyoxyl 40 castor oil (Cremophor RH 40) | 14-16 |
| Polyoxyl hydrogenated castor oil (Cremophor RH 60) | 15-17 |
| PEG-PPG-PEG Pluronic ® L-64 | 12-18 |
| Poly(propylene glycol)-block-poly(ethylene glycol)-block-poly(propylene glycol) average $M_n$ ~2,000 (PPG-PEG-PPG Pluronic ® 10R5) | 12-18 |

The surfactants and HLB values set forth in the Tables above are exemplary. Any known surfactant or co-surfactant, suitable for use in a pharmaceutical composition, can be used in the emulsions provided herein.

1. Exemplary Surfactants/Co-Surfactants in the Lipid Phase

For example, in the lipid phase, exemplary surfactants are of the nonionic type such as, but not limited to, for example: poloxamers, such as those sold under the trademarks Pluronic®, a hydrogenated castor oil ethoxylate, such as Kolliphor® and Cremophor®, polysorbates (such as Tween™), lauryl dimethyl amine oxide, polyethoxylated alcohol, polyoxyl lauryl ether, nonionic polyoxyethylene surfactants, such as that sold under the trademark Brij®, polyoxyl castor oil, lecithin, poloxamers, polyethylene glycol, and glycerol esters of fatty acids. In some embodiments, the co-surfactant in the lipid phase is/are propylene glycol and/or glycerol.

2. Exemplary Surfactants/Co-Surfactants in the Aqueous Phase

In the aqueous phase, exemplary surfactants are of the nonionic type such as, but not limited to, for example: poloxamers, such as those sold under the trademark Pluronic®, hydrogenated castor oil ethoxylates, such as Cremophor®, and Kolliphor®, polysorbates, such as Tween™, Lauryl dimethyl amine oxide, polyethoxylated alcohol, polyoxyl lauryl ether, nonionic polyoxyethylene surfactants, such as those sold under the trademark Brij®, polyoxyl castor oil, lecithin, polyethylene glycol, glycerol esters of fatty acids. In some embodiments, the co-surfactant(s) in the aqueous phase is propylene glycol and/or glycerol.

D. Aqueous Phase Components

The aqueous phase includes polar protic solvents, generally those suitable for ophthalmic applications, such as water. The aqueous phase includes all polar and water-soluble ingredients, and include a surfactant and a co-surfactant. Other ingredients in the aqueous phase can include alcohols and glycerin and other such solvents.

E. Lipid Phase Components

The lipid phase includes at least one oil, and non-polar ingredients, including pharmaceutical agents/drugs that are not soluble in aqueous compositions. The lipid phase includes at least one oil. The oil can be a natural oil or synthetic oil, and must be one that is biocompatible. Suitable natural oils, include, but are not limited to, vegetable and/or animal oils, such as, by way of example soya oil, corn oil, linseed oil, sunflower oil, krill oil, cod-liver oil, fish oil, avocado oil, almond oil, babassu oil, borage oil, carob oil, cashew nut oil, grapeseed oil, coconut oil, *Oryza sativa* bran oil, castor oil, hemp seed oil, jojoba oil, peanut oil, poppy seed oil, sesame oil, walnut oil, olive oil, wheat-germ oil, argan oil, cottonseed oil, blackcurrant seed oil, and oils rich in PUFAs by a fraction greater than 10%. Mineral oils of synthetic origin, such as, by way of example esters of medium and long-chain fatty acids, medium and long-chain triglycerides.

F. Additional Ingredients

The microemulsions can include additional ingredients suitable and useful in pharmaceutical compositions. The following are exemplary of such ingredients. All should be biocompatible so that they can be, for example, topically applied to the eye or injected into the eye or ingested or administered parentally.

1. Buffers

The microemulsions can include buffers to maintain the pH at a desired range, generally between about 5.0 and 8, such as between 5.2 and 8, such as 7.4 or 7.5. Exemplary biocompatible suitable buffers include, but are not limited to: Trometamol (Tris buffer, 2-Amino-2-(hydroxymethyl) propane-1,3-diol), McIlvaine (citrate-phosphate buffer), Sorensen (0.133 M $Na_2HPO_4$ 0.133 M $KH_2PO_4$ pH 7.2), sodium lactate, sodium acetate, sodium borate, boric acid, and imidazole. An exemplary buffer is histidine and citrate adjusted to pH with NaOH or HCl. The suitable buffer concentration is in the range of 10-50 mM.

2. Tonicity Agents

The microemulsions can include isotonizing agents. These compounds are used to achieve the required tonicity in the preparation. Exemplary of these are glycerol, sorbitol, mannitol, sucrose, trehalose, propylene glycol, dextrose, ethylene glycol, sodium chloride, potassium chloride, magnesium chloride, and calcium chloride. In one embodiment, the microemulsion comprises excipients such as: stabilizing agents, antioxidants, antimicrobials, thickening agents, branched and linear polymers. Tonicity agents are used at concentrations that guarantee osmolality of the formulation ranging, for example, between 100-400, inclusive, mOsmol/kg of the composition 3. Stabilizing Agents The stabilizing agents are chosen by way of example from glycine, proline, cyclodextrins, calixarenes, hypromellose, histidine, betaine, albumin, L-carnitine, taurine, glyceryl monostearate, pectins, polyvinyl alcohol, and propylene glycol. It is within the skill in the art to determine an appropriate concentration, which depends upon, for example, the particular stabilizing agent(s) and the other components of the composition. For example, the amount can be between 0.0001% to 20% w/v, inclusive.

4. Thickening Agents

The microemulsions can include thickening agents. The thickening agents include, but are not limited to, those extracted from plants, microbes and animals. Many thickening agents are known to those of skill in the art. Exemplary of thickening agents extracted from plants are gums. Exemplary of thickening agents are gums, such as gums extracted from plants belonging to the genera *Cyamopsis*,

*Sterculia, Ipomoea, Trigonella, Cassia, Physaria, Tamarindus, Ceratonia, Caesalpinia*; exudates of vegetable origin, such as, by way of example those related to species belonging to the genera *Manilkara, Amorphophallus, Acacia, Anogeissus, Sterculia, Astragalus*; gums of microbic origin, such as, by way of example dextran, gellan gum, xanthan gum; extracts of marine origin, such as, by way of example sodium alginate, alginic acid, carrageenan, agar-agar, and derivatives of *Ulva lactuca, Alga nori, Arthrospira platensis*; derivatives of animal origin, such as, by way of example chitin and chitosan, hyaluronic acid; derivatives of cellulose, such as, by way of example carboxymethycellulose (CMC), hydroxyethyl cellulose, hydroxypropyl methyl cellulose (HPMC), methylcellulose (MC), microcrystalline cellulose (MCC).

5. Antioxidants

Antioxidants can be included in the microemulsion compositions. Exemplary of antioxidants are α-tocopherol, flavonoids (e.g. resveratrol, epigallocatechin-3-gallate, quercetin, naringenin, delphinidin) coenzyme Q10, NDGA (nordihydroguaiaretic acid), meso-NDGA, sodium ascorbate, L-ascorbic acid, N-acetylcarnosine, citric acid, erythorbic acid, L-6-ascorbyl palmitate, L-carnosine, L-glutathione, L-cysteine, cysteine ascorbate. The amount can be determined by the skilled person. It can depend upon the particular antioxidant(s) employed and the other components of the composition. An exemplary range is between 0.0001% and 5.0% w/v, inclusive.

G. Microemulsion Compositions Containing Active Ingredients

The microemulsion compositions provided herein are to be used as pharmaceutically acceptable carriers for formulating biologically active molecules, such as small molecule drugs and biologics. The microemulsions provided herein are advantageous for formulating active agents that have low solubility in aqueous solutions. The microemulsions provided are used to formulate such active agents in a form that is stable and can also be preserved at room temperature.

The microemulsions provided herein can be used for oral, parenteral, topical and local application. In particular embodiments, the emulsions are for ophthalmic administration. The microemulsions can be formulated, for example, for topical application, such as eye drops, or for injection, such as intravitreal injection, depending upon the indication.

1. Active ingredients

Active ingredients include pharmaceutically and biologically active compounds, such as small molecule drugs and biologics, particularly agents that have limited solubility in aqueous compositions. The active agents are formulated, generally by adding them to the lipid phase, and then, mixing the lipid phase with the aqueous phase, such as by titration as described herein. The lipid and aqueous phases contain the required amounts and ratios of surfactants/co-surfactants and lipids as described herein. The microemulsions that form are characterized by having small particles (<30 nm, such as 15 nm±10 nm), and a narrow particle size range distribution, such as a PDI<0.2, high thermodynamic stability, and good bioavailability and activity of the formulated active agent.

The microemulsions generally contain less than 5% (w/v) of the active agent, but can contain any amount of interest, such as 0.01 mg/ml to 50 mg/ml, such as 0.01 to 30 mg/ml. The particular amount(s) depends upon the pharmaceutical, the indication for which it is used, the route of administration, and the subject. It is well within the skill in the art to formulate the agent at an appropriate concentration.

Active ingredients include any known pharmaceutical, particularly those with low solubility in aqueous compositions. Included, for example are any pharmaceutical molecules chosen from the groups as defined by the United States Pharmacopeia (USP). These include, but are not limited to, gastrointestinal agents, antispasmodics, blood sugar regulators, nutraceuticals/minerals/electrolytes, platelet modifying agents, coagulants, cardiovascular agents, alpha-adrenergic agonists/alpha-adrenergic antagonists/vasodilators/arterial vasodilators, carbonic anhydrase inhibitor diuretics/loop diuretics/potassium-sparing diuretics/thiazide diuretics, other cardiovascular agents, beta-adrenergic antagonists, calcium channel blockers, angiotensin converting enzyme inhibitors (ACE), dyslipidemics/HMG CoA Reductase inhibitors (Statins), anti-fungals, dermatological agents, anti-histamines, anesthetics, anti-bacterials, hormone-stimulating agents/substituents/modifiers (adrenals, pituitary and sex hormones), glycemic agents, hormone-suppressing agents (parathyroids), anti-mycobacterials, anti-virals, anti-neoplastics, immunomodulators, anti-inflammatory agents, analgesics, anti-convulsants, anti-Parkinson agents, anti-psychotics, anti-depressants/anti-dementia agents/anti-anxiety medication, anti-myasthenic agents/agents for treating substances of abuse/central nervous system agents, bronchodilators/sympathomimetics/anti-cholinergics/inhaled corticosteroids/phosphodiesterase inhibitors/airborne disorders, other agents of the respiratory tract, anti-parasites, anti-glaucoma ophthalmic agents, other ophthalmic agents/anti-allergic ophthalmic agents, ophthalmic anti-inflammatories, prostaglandin analogues and ophthalmic prostamides.

Active ingredients also include, but are not limited to, any from the groups defined by the Anatomical Therapeutic Chemical Classification System (ATC) compiled by the World Health Organization. These include drugs for acidity-related disorders (A02), drugs for gastrointestinal function disorders (A03), drugs used for diabetes (A10), vitamins (A11), mineral supplements (A12), antithrombotic agents (B01), anti-hemorrhagics (B02), cardiac therapy drugs (C01), anti-hypertensives (C02), diuretics (C03), peripheral vasodilators (C04), vasoprotectives (C05), beta-blocking agents (C07), calcium-antagonists (C08), drugs acting on the renin-angiotensin system (C09), lipid-lowering drugs (C10), anti-fungals for dermatological use (D01), emollients and protectives (D02), drugs for injuries and ulcers (D03), antipruritics, including anti-histamines, anaesthetics (D04), anti-psoriasis drugs (DOS), antibiotics and chemotherapeutic agents for dermatological use (D06), antiseptics and disinfectants (D08), hyphophyseal, hypothalamic hormones and similar (H01), systemic corticosteroids (H02), thyroid therapy (H03), pancreatic hormones (H04), homeostatic calcium (HOS), anti-bacterials for systemic use (J01), anti-mycotics for systemic use (J02), anti-mycobacterials (J04), anti-viral drugs for systemic use (J05), immune serums and immunoglobulins (J06), anti-neoplastic agents (L01), endocrine therapy (L02), immunostimulants (L03), immunosuppressants (L04), anti-inflammatories and anti-rheumatics (M01), topical products for joint and muscle pain (M02), anesthetics (N01), analgesics (N02), anti-epileptics (N03), anti-parkinsonians (N04), psycholeptics (N05), psychoanaleptics (N06), other nervous system drugs (N07), rhinologic preparations (R01), preparations for the pharyngeal cavity (R02), drugs for obstructive disorders of the respiratory tract (R03), preparations for coughs and colds (R05), anti-histamines for systemic use (R06), other preparations for the respiratory system (R07), anti-infectives (S01A), anti-inflammatory agents (S01B), anti-inflammatory agents and anti-infectives combined (S01C), anti-glaucoma agents and miotics (S01E), mydriatics and cyclopegics (S01F), decongestants and anti-allergens (S01G), local anaesthetics (S01H), diagnostic agents (S01), surgical aids (S01K), ocular vascular agents (S01L), anti-infectives (S03A), corticosteroids (S03B), and corticosteroids combined with anti-infectives (S03C).

2. Ophthalmic Agents

The microemulsions as described herein are particularly suitable for ophthalmic applications. Thus, any ophthalmic drug can be formulated in the microemulsions. Drugs for ocular use include, but are not limited to, steroidal anti-inflammatory agents, antimicrobial drugs, anti-glaucoma agents, antihypertensives, diagnostic agents, antiviral agents, anti-angiogenic agents, neuroprotectants, and anti-oxidants. These ingredients can be used alone or in combination.

For example, the active ingredient can be for treatment of ocular hypertension or glaucoma such as, for example: prostaglandins (latanoprost, travoprost, bimatoprost), beta-blockers (timolol, carteolol, levobunolol, betaxolol, nebivolol), parasympathomimetics (pilocarpine), alpha2-agonists (apraclonidine, brimonidine), carbonic anhydrase inhibitors CAI—(brinzolamide, dorzolamide), and derivatives thereof. In one exemplary embodiment, the active ingredient in the microemulsion is chosen from one or more prostaglandin analogs, such as, for example latanoprost, travoprost, bimatoprost, and derivatives.

In other embodiments, the active ingredient is an anti-angiogenic, such as, for example sorafenib, sorafenib tosylate, regorafenib, regorafenib tosylate, regorafenib isethionate, regorafenib ethylsulfonate, apremilast, radotinib, spironolactone, or an anti-oxidant, such as nordihydroguaiaretic acid, meso-nordihydroguaiaretic acid (masoprocol), a hydrate, solvate, metabolite or a salt from these, which is acceptable from a pharmaceutical point of view, or a polymorphic crystalline form of the molecules; or the molecule can be a beta-blocker, such as timolol, betaxolol, levobunolol, nebivolol and carteolol; or it is a corticosteroid, such as dexamethasone, or a non-steroidal anti-inflammatory drug (NSAID) or a mixture of two or more of the active ingredients.

The microemulsions contain active ingredients in a concentration range from about 0.01 to 50 mg/ml, such as 0.01 to 30 mg/ml. The results shown and described herein demonstrate that the microemulsion confer enhanced stability to the active ingredients, without interfering with the biological action of the active ingredient. For example, Example 6 shows that microemulsions provided herein effectively carry various active ingredients, alone and in combination. The microemulsions confer stability to the active ingredient included in the formulation. For example, Example 11, shows latanoprost activity in the resulting microemulsion, measured in vivo, is at least comparable to that observed using latanoprost in a commercial ophthalmic solution. The chemical stability of the active ingredient is maintained at room temperature.

For example, microemulsions containing masoprocol or sorafenib tosylate are effective in animal models of retinal ischemia-reperfusion, choroidal neovascularization and diabetic retinopathy. As shown in Example 16, microemulsions containing masoprocol 0.302% (formulation 04) are effective in a murine model of dry eye, a pathology of the surface of the eye.

Thus, microemulsions as provided herein permit formulation of any known pharmaceutically active agent, and provide enhanced stability, while retaining activity at least comparable to other formulations that do not confer the enhanced stability.

H. Diseases and Conditions of the Eye and Methods of Treatment

The microemulsions provided herein can serve as vehicle for administration of any active agent, particularly those of low solubility in aqueous compositions. The microemulsions can be used for treatment of ophthalmic disorders by formulating active agents used for treating disorders, conditions and diseases of the eye. The microemulsions provided herein are particularly suitable for these indications because they contain ingredients that are compatible with the tissues of the eye, and because they can provide these agents in a form that is stable and has good bioavailability. These conditions, diseases and disorders, include ophthalmic conditions and pathologies, such as, but not limited to glaucoma, Age-Related Macular Degeneration AMD, diabetic retinopathy, neuropathies, bacterial infections, viral infections, dry eye, allergic and/or inflammation in the eye. The microemulsions can be formulated for topical administration to the eye or for injection or any suitable route.

Different types of diseases affect the eye. The eye is divided into two segments: (1) the anterior segment that contains the cornea, iris, pupil, conjunctiva, ciliary body, anterior chamber, aqueous humor, trabecular meshwork, and lens; and (2) the posterior segment that contains the vitreous humor, sclera, choroid, retina, macula and optic nerve. There are many diseases and conditions of the eye, and pharmaceutically active agents that are used to treat such diseases and conditions. Administration can be effected by any route, such as topically using eye drops, and by injections, such as intravitreal injection. Treatment is important as some diseases eventually lead to blindness.

The following are exemplary of diseases that can be treated, and drugs that can be formulated in the microemulsions provided herein.

1. Glaucoma

Glaucoma is a multifaceted disorder resulting from damage to the retinal ganglion cells and their axons, causing progressive optic nerve degeneration and leading to irreversible blindness in some patients. There are two main categories of glaucoma that are characterized by an elevated intraocular pressure (IOP) such as Open-angle glaucoma (OAG) and Angle-closure glaucoma (ACG). OAG is a chronic condition where there is a partial blockage within the trabecular meshwork or Schlemm's canal that compromises the ability of the aqueous humor (AqH) to be properly drained from the eye, resulting in an increased IOP. ACG is defined by a closing of the iridocorneal angle within the anterior chamber, and is caused by factors that either pull or push the iris up into the anterior chamber. This change in morphology can physically block the drainage of AqH by restricting flow through the iridocorneal canal and trabecular meshwork. Moreover, there is a Normal-tension glaucoma (NTG) that is a form of OAG characterized by glaucomatous optic neuropathy in patients with IOP measurements consistently lower than 21 mmHg.

Drugs for treatment of glaucoma include prostaglandin analogs, such as, latanoprost, bimatoprost, travoprost and tafluprost; beta-blockers, such as timolol, carteolol, levobunolol and betaxolol, and alpha-adrenergic agonists, such as brimonidine and apraclonidine, and carbonic anhydrase inhibitors, such as dorzolamide and brinzolamide, and pharmaceutically acceptable derivatives, hydrates, solvates, metabolites and salts thereof, or a polymorphic crystalline form of the molecules. Moreover, since 2014, new classes of drugs have been developed with new mechanisms of action, such as nitric oxide (NO)-donating prostaglandin F2-alpha analogue (latanoprostene bunod), rho kinase inhibitors (ripasudil and netarsudil mesylate) and prostaglandin EP2 receptor agonist (DE-117).

2. Macular Degeneration

Age-related macular degeneration (AMD) is a disease that affects the macular region of the retina, causing progressive loss of central vision; it is a multifactorial disorder, with dysregulation in the complement, lipid, angiogenic, inflammatory, and extracellular matrix pathways implicated in its pathogenesis. By 2020, the number of people with AMD globally is expected to be around 200 million, increasing to nearly 300 million by 2040. There are two major forms of MD, with different prognosis and therapy: the atrophic or dry-type MD, representing approximately the 85-90% of the total number of cases, and the neovascular or wet-type MD. The initial alteration of the fundus is often represented by the so-called drusen, or colloids bodies, that are degenerative formations of yellowish color and round shape mostly found at the posterior pole. Considering the mechanisms inducing the chronic retinal damage, an alteration of the metabolic sustainment of the photoreceptors cells (rods and cones) and of the retinal pigment epithelium (RPE) is supposed, depending on inflammation processes and vascular modifications. Among the drugs for Wet AMD are VEGF antagonists, and, also inhibitors of complement activation that target complement C3 or C5. Exemplary of such drugs, which are administered by intravitreal injection, are ranibizumab (trade name: Lucentis), and aflibercept (Eylea), pegaptanib (Macugen®), and bevacizumab (Avastin®) Classes of drugs with other mechanisms of action are being developed. These include, for example, anti-complement agent (C3 Inhibitor) (APL-2), anti-complement agent avacincaptad pegol (C5 Inhibitor; Zimura®), alpha2-adrenergic receptor agonist (Brimo DDS), DARPin based anti-VEGF (abicipar pegol), scFv anti-VEGF antibody fragment (brolucizumab), anti-VEGF-C and VEGF-D (OPT-302). There are also promising drugs in early-stage development such as targets C5/complement factor F (CLG561/LFG316 combination), binds Ang2/VEGF as a single molecule (RG7716), anti-endoglin antibody (DE-122), VEGF inhibitor (LHA510 and PAN-90806), integrin $\alpha v \beta 3$ antagonist (SF0166), PDGF/VEGF inhibitor (X-82), CTGF inhibitor (RXI-109), VEGF, PDGF and bFGF inhibitor (squalamine lactate), PPAR-alpha agonist (BIO-201), antioxidant/NF-kB inhibitor (CPC-551), mPTP opening blocker (ocuvia), 16S rRNA of 30s ribosomal subunit inhibitor (FMX-103), tissue factor inhibitor (ICON-1), MASP-2 antibody (OMS-721), $\beta$-amyloid inhibitor (ALZ-801) and ROBO4 agonist (DS-7080).

3. Dry Eye

Dry eye is a multifactorial disease of the ocular surface characterized by a loss of homeostasis of the tear film, and accompanied by ocular symptoms, in which tear film instability and hyperosmolarity, ocular surface inflammation and damage, and neurosensory abnormalities play etiological roles. The management of this ocular disease is dominated by the widespread use of artificial tears that contain hydrogel polymers such as sodium hyaluronate and methylcellulose; corticosteroids such as fluorometholone, prednisolone and dexamethasone; immunosuppressant and anti-inflammatory such as, cyclosporine. Moreover, new classes of drugs have been developed with new mechanisms of action, such as P2Y2 receptor agonist (diquafosol tetrasodium); mucin secretagogue (rebamipide); integrin inhibitor and anti-inflammatory (lifitegrast); TrkA agonist and neurotrophin peptidomimetic (tavilermide); mitochondrial antioxidant (visomitin) and recombinant human nerve growth factor (RH-NGF). Other drugs in clinical development. These, include, for example, as thymosin beta 4/synthetic peptide (RGN-259), RNAi-based TRPV1 inhibitor (tivanisiran), aldehyde-trap (reproxalap) and recombinant human lubricinprotein (ECF-843) and promising drugs in early-stage development such as a synthetic fragment of lacritin (lacripep), calcineurin inhibitor (voclosporin), epithelial sodium channel blocker (P-321).

4. Meibomian Gland Dysfunction (MGD)

Meibomian gland dysfunction (MGD) is a chronic, diffuse abnormality of the meibomian glands, commonly characterized by terminal duct obstruction and/or qualitative/quantitative changes in the glandular secretion. This may result in alteration of the tear film, symptoms of eye irritation, clinically apparent inflammation, and ocular surface disease. MGD can lead to alterations in the normal lipid composition in meibomian gland secretions. Lipid abnormalities can lead to abnormalities of tear film composition and function resulting in evaporative dry eye. Systemic minocycline and doxycycline are known to produce significant effects in the management of MGD.

5. Cataract

Cataract is the opacification of the eye lens resulting in a change to the refractive index and therefore creating a loss of vision. Depending on the location of the opacification, an age-related cataract can be classified as cortical, nuclear, or posterior subcapsular cataract. In addition to aging, eye injuries, infections, and surgeries can cause cataract formation. Even though surgical therapy is well established and effective, it cannot be performed in many developing countries due to the lack of both the required instrumentation and medical professionals. The development of nonsurgical treatments is crucial for preventing and reversing cataracts. Interestingly, antioxidants, chaperones, chaperone activators, and protein aggregation inhibitors are promising drug candidates. For example, eye drops containing lanosterol have been shown to improve vision.

6. Diabetic Retinopathy and Macular Edema

Diabetic retinopathy (DR) and macular edema, the most-feared complication of diabetes mellitus, is the most frequent cause of new cases of blindness (28.5%) among adults aged 20-74 years. DR is clinically classified into nonproliferative and proliferative disease stages. In nonproliferative DR (NPDR), intraretinal microvascular changes occur including microaneurysms, altered retinal vascular permeability and eventual retinal vessel closure and nonperfusion. PDR involves the formation of new blood vessels on the retina or the optic disk. These new abnormal blood vessels erupt through the surface of the retina and proliferate into the vitreous cavity of the eye, where they can hemorrhage into the vitreous, resulting in visual loss. Treatments include anti-inflammatories, and VEGF-inhibitors 7. Infections and Allergies Infections of the eye are treated with appropriate antibiotics, anti-virals, anti-fungals, anti-inflammatories and combinations thereof and combinations with antibiotics. The particular treatment depends type of infection and locus of the infection.

I. Methods of Making the Microemulsion

Figure 2:
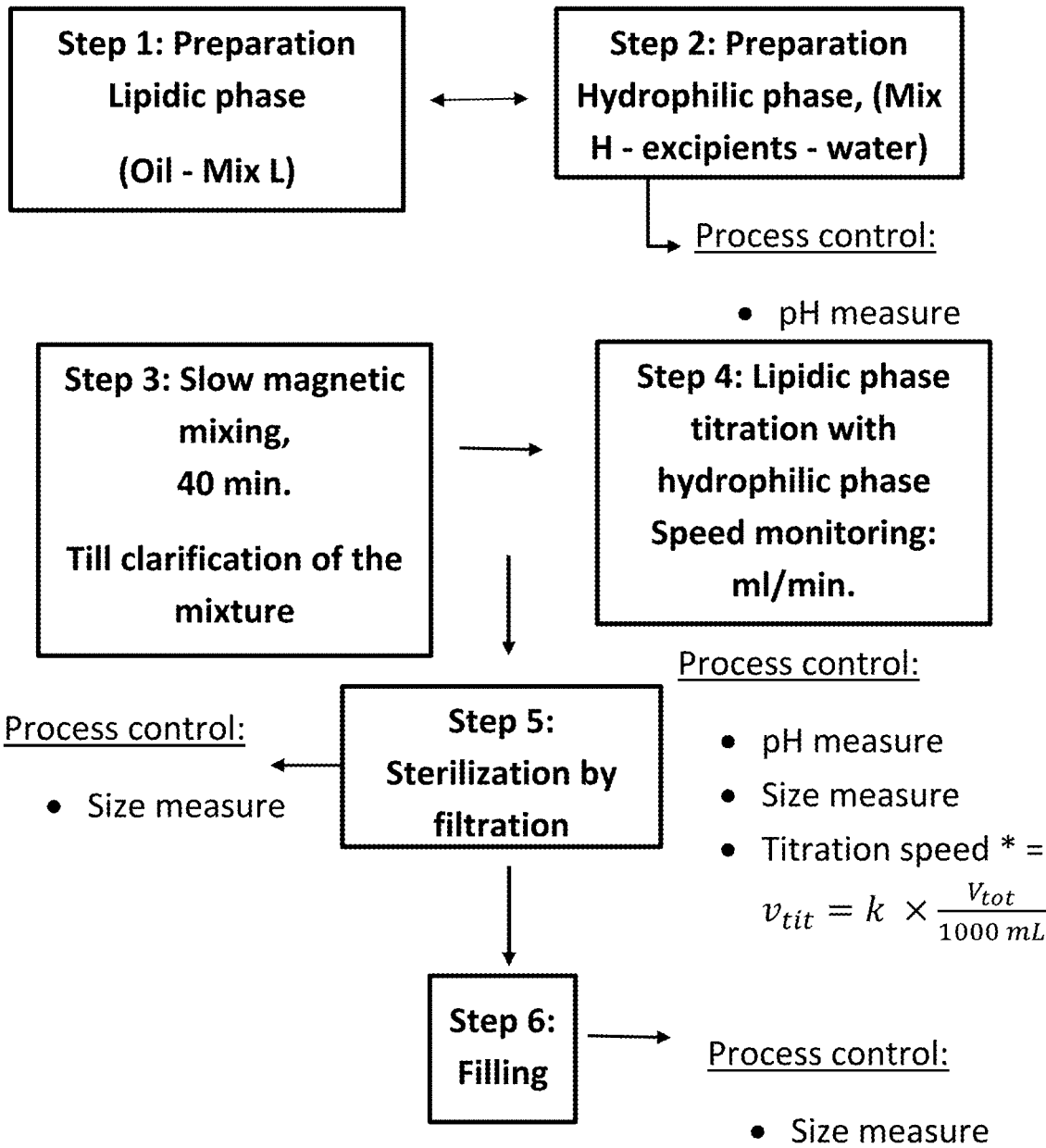
FIG. 2 depicts a diagram of the process for preparing the microemulsions provided herein.

The microemulsions can be prepared by preparing the aqueous phase and lipophilic phase containing surfactants/ co-surfactants in amounts within or at the ratios described herein, and then mixing the phases, which form the microemulsions. Exemplary of the methods for preparing microemulsions herein are those depicted in FIG. 1 and FIG. 2. An exemplary method, includes the steps of:

preparing the lipid phase, where a mixture of one or more surfactants/co-surfactants is solubilized in oil, mixing from 1 to 10 parts of the mixture for every part of oil;

preparing the aqueous phase, where a surfactant/co-surfactant mixture plus any excipients is solubilized in water or other polar protic solvent; titrating of the lipid phase with the aqueous phase to produce a microemulsion where 0.4-4.0% (w/v) of the microemulsion is composed of the oily component of the lipid phase, 4.0%-36.0% (w/v) of the microemulsion is composed of the surfactants/co-surfactants of the lipid phase, and 1.66%-4.15% (w/v) of the total surfactants/co-surfactants are the surfactants/co-surfactants from the aqueous phase.

In one embodiment, the lipid and aqueous phases are combined by slow magnetic-driven mixing. The titration can be performed at a speed, which is described by the following equation:

$$V_{tit} = k \times (v_{tot}/1000 \text{ ml}),$$

where $V_{tit}$=titration speed in ml×min$^{-1}$, k=2 ml×min$^{-1}$, $V_{tot}$=total volume of the formulation in ml.

The micellar dimension in the resulting composition is about 15±10 nm and the polydispersity index (PDI) is within the range 0.02-0.380, or 0.02 to 0.2, or 0.02 to 0.15, inclusive, or is less than 0.2 or less than 0.12 or less than 0.1. The preparation is performed at room temperature.

Advantageously, the microemulsions provided herein, particularly those that are intended for ophthalmic indications, do not contain any co-surfactant of an alcoholic nature. The resulting microemulsions, thus, are biocompatible, i.e. well tolerated, with ocular tissues.

J. EXAMPLES

The following examples are included for illustrative purposes only and are not intended to limit the scope of the invention.

Example 1

Illustrative Microemulsions

A series of microemulsions that contain amounts of surfactants and co-surfactants and lipid phase in accord with the ratios and amounts as provided herein were prepared. One formulation, designated formulation 5, was prepared with amounts outside the ratios, to demonstrate the effect of the ratios.

Formulations with active drugs also were prepared to assess various parameters and activities. The ratios to form microemulsions with the advantageous properties described herein are, for example:

weight/volume ratio between surfactant/co-surfactant in the lipid phase and surfactant/co-surfactant in the aqueous phase is from 2 to 10, such as 2.2 to 9.8 or 2.4 to 8.6, and the weight/volume ratio between the oily component of the lipid phase and the surfactants/co-surfactants in the aqueous phase is from 0.2 to 1.0, such as from 0.22 to 0.98, or 0.24 to 0.96.

In the lipid phase of microemulsions, the weight/volume ratio between the oily component of the lipid phase, and the mixture of the surfactants/co-surfactants is from 0.05 to 1.4, such as from 0.07 to 1.2, or 0.1 to 1.

Five formulations were obtained using isopropyl myristate as an oily phase, water as a dispersant, Tween 80 and Kolliphor RH40 as emulsifying agents (surfactants), propylene glycol (co-surfactants) as a wetting agent, sodium citrate dihydrate as a buffer, and citric acid as a pH adjuster. As detailed below, the emulsifiers and the wetting agent are the surfactant and co-surfactants, respectively, in the lipid phase and/or in the aqueous phase, respectively.

Microemulsion for Ophthalmic Use, Formulation 1:

| Components | % w/v |
| --- | --- |
| Isopropyl myristate | 0.400 |
| Tween 80 | 2.700 |
| Kolliphor RH40 | 1.245 |
| Propylene glycol | 1.765 |
| Sodium citrate dihydrate | 0.500 |
| Citric acid 0.1N | q.s. pH 7.40 |
| Purified water | q.s. 100 ml |

Tween 80 and propylene glycol are the surfactant/co-surfactant in the lipid phase. The Tween 80 and the propylene glycol are in a ratio of 2:1. In the aqueous phase, the surfactant and co-surfactant are Kolliphor RH40 and propylene glycol, respectively. In the aqueous phase, the Kolliphor RH40 and the propylene glycol are in a ratio of 3:1. In formulation 1, the surfactant/co-surfactant in the lipid phase are 4.05% (w/v) of the microemulsion and the surfactant/co-surfactant of the aqueous phase are 1.66% (w/v) of the microemulsion.

Microemulsion for Ophthalmic Use, Formulation 2:

| Components | % w/v |
| --- | --- |
| Isopropyl myristate | 1.410 |
| Tween 80 | 4.150 |
| Kolliphor RH40 | 11.410 |
| Propylene glycol | 7.260 |
| Sodium citrate dihydrate | 0.500 |
| Citric acid 0.1N | q.s. pH 7.40 |
| Purified water | q.s. 100 ml |

Tween 80, Propylene glycol and Kolliphor RH40 are the surfactants/co-surfactants of the lipid phase. In the lipid phase, the Tween 80, the propylene glycol and the Kolliphor RH40 are in a ratio of 1:2:1.5. Kolliphor RH40 and propylene glycol are the surfactants/co-surfactants in the aqueous phase, where, in the aqueous phase, the Kolliphor RH40 and the propylene glycol are in a ratio of 3:1. In formulation 2, the surfactants/co-surfactants of the lipid phase are 18.67% (w/v) of the microemulsion and the surfactants/co-surfactants of the aqueous phase are 4.15% (w/v) of the microemulsion.

Microemulsion for Ophthalmic Use, Formulation 3:

| Components | % w/v |
| --- | --- |
| Isopropyl myristate | 4.000 |
| Tween 80 | 8.000 |
| Kolliphor RH40 | 19.110 |
| Propylene glycol | 13.040 |
| Sodium citrate dihydrate | 0.500 |
| Citric acid 0.1N | q.s. pH 7.40 |
| Purified water | q.s. 100 ml |

Tween 80, Propylene glycol and Kolliphor RH40 are the surfactants/co-surfactants of the lipid phase, where, in the lipid phase, the Tween 80, the propylene glycol and the Kolliphor RH40 are in a ratio of 1:2:1.5; Kolliphor RH40 and propylene glycol are the surfactants/co-surfactants of the aqueous phase, where, in the aqueous phase, the Kolliphor RH40 and the propylene glycol are in a ratio of 3:1. In formulation 3, the surfactants/co-surfactants of the lipid phase are 36% (w/v) of the microemulsion and the surfactants/co-surfactants of the aqueous phase are 4.15% (w/v) of the microemulsion.

Microemulsion for Ophthalmic Use, Formulation 4:

| Components | % w/v |
| --- | --- |
| Isopropyl myristate | 0.400 |
| Tween 80 | 0.900 |
| Kolliphor RH40 | 3.045 |
| Propylene glycol | 1.765 |
| Sodium citrate dihydrate | 0.500 |
| Citric acid 0.1N | q.s. pH 7.40 |
| Purified water | q.s. 100 ml |

Tween 80, Propylene glycol and Kolliphor RH40 are the surfactants/co-surfactants of the lipid phase, where, in the lipid phase, the Tween 80, the propylene glycol and the Kolliphor RH40 are in a ratio of 1:2:1.5; Kolliphor RH40 and propylene glycol are the surfactants/co-surfactants of the aqueous phase, where, in the aqueous phase, the Kolliphor RH40 and the propylene glycol are in a ratio of 3:1. In formulation 4, the surfactants/co-surfactants of the lipid phase are 4.05% (w/v) of the microemulsion and the surfactants/co-surfactants of the aqueous phase are 1.66% (w/v) of the microemulsion.

Formulation 5—Comparison Formulation

| Components | % w/v |
| --- | --- |
| Isopropyl myristate | 0.500 |
| Tween 80 | 3.390 |
| Kolliphor RH40 | 1.965 |
| Propylene glycol | 2.350 |
| Sodium citrate dihydrate | 0.500 |
| Citric acid 0.1N | q.s. pH 7.40 |
| Purified water | q.s. 100 ml |

The ingredients in formulation 5, described below, do not meet the requisite ratios. It is specifically composed so that the ratio between the oily component and surfactants/co-surfactants in the aqueous phase, and the ratio between surfactants/co-surfactants in the lipid phase and surfactants/co-surfactants in the aqueous phase do not fall within the parameters of the emulsions as provided herein. It was prepared for comparison with the microemulsions provided herein to demonstrate that the advantageous properties of the microemulsions provided herein derive from the ratios.

Tween 80 and propylene glycol are the surfactants/co-surfactants in the lipid phase, where, in the lipid phase, the Tween 80 and the propylene glycol are in a ratio of 2:1; Kolliphor RH40 and propylene glycol are the surfactants/co-surfactants of the aqueous phase, where, in the aqueous phase, the Kolliphor RH40 and the propylene glycol are in a ratio of 3:1. In formulation 5, the surfactants/co-surfactants of the lipid phase are 5.08% (w/v) of the microemulsion and the surfactants/co-surfactants of the aqueous phase are 2.62% (w/v) of microemulsion.

Formulations 6-9

Four formulations (6, 7, 8 and 9), were prepared using krill oil or coconut oil or a mixture of 3 parts of krill oil and 1 part of borage oil, as an oily phase, water as a dispersant, Tween 80 and Kolliphor RH40 as emulsifying agents, propylene glycol as a wetting agent, sodium citrate dihydrate as a buffer and citric acid as a pH adjuster.

Tween 80, propylene glycol and Kolliphor RH40 are the surfactants/co-surfactants of the lipid phase, where, in the lipid phase, the Tween 80, the propylene glycol and the Kolliphor RH40 are in a ratio of 1:2:1.5; Kolliphor RH40 and propylene glycol are the surfactants/co-surfactants of the aqueous phase, where, in the aqueous phase, the Kolliphor RH40 and the propylene glycol are in a ratio of 3:1. In formulation 6, the surfactants/co-surfactants of the lipid phase are 4.05% (w/v) of the microemulsion and the surfactants/co-surfactants of the aqueous phase are 1.66% (w/v) of the microemulsion. In formulations 7, 8, and 9, the surfactants/co-surfactants of the lipid phase are 18.67% (w/v) of the microemulsion and the surfactants/co-surfactants of the aqueous phase are 4.15% (w/v) of the microemulsion.

Microemulsion for Ophthalmic Use, Formulation 6:

| Components | % w/v |
| --- | --- |
| Krill oil | 0.400 |
| Tween 80 | 0.900 |
| Kolliphor RH40 | 3.045 |
| Propylene glycol | 1.765 |
| Sodium citrate dihydrate | 0.500 |
| Citric acid 0.1N | q.s. pH 7.40 |
| Purified water | q.s. 100 ml |

Microemulsion for Ophthalmic Use, Formulation 7:

| Components | % w/v |
| --- | --- |
| Coconut oil | 1.410 |
| Tween 80 | 4.150 |
| Kolliphor RH40 | 11.410 |
| Propylene glycol | 7.260 |
| Sodium citrate dihydrate | 0.500 |
| Citric acid 0.1N | q.s. pH 7.40 |
| Purified water | q.s. 100 ml |

Microemulsion for Ophthalmic Use, Formulation 8:

| Components | % w/v |
| --- | --- |
| Krill oil | 1.410 |
| Tween 80 | 4.150 |
| Kolliphor RH40 | 11.410 |
| Propylene glycol | 7.260 |
| Sodium citrate dihydrate | 0.500 |
| Citric acid 0.1N | q.s. pH 7.40 |
| Purified water | q.s. 100ml |

Microemulsion for Ophthalmic Use, Formulation 9:

| Components | % w/v |
| --- | --- |
| Krill oil | 1.060 |
| Borage oil | 0.350 |
| Tween 80 | 4.150 |
| Kolliphor RH40 | 11.410 |
| Propylene glycol | 7.260 |

-continued

| Components | % w/v |
| --- | --- |
| Sodium citrate dihydrate | 0.500 |
| Citric acid 0.1N | q.s. pH 7.40 |
| Purified water | q.s. 100 ml |

Formulations 10-16

Three formulations (10, 11 and 12) were obtained using a mixture containing 3 parts of castor oil and 1 part of oriza sativa bran oil or 1 part of avocado oil or 1 part of grape seed oil, as an oily phase, water as a dispersant, Tween 80 and Kolliphor RH40 as emulsifying agents, propylene glycol as a wetting agent, sodium citrate dihydrate as a buffer and citric acid as a pH adjuster.

Three formulations (13, 14 and 15), were obtained using a mixture of 3 parts of krill oil and 1 part of borage oil or 1 part of linseed oil or 1 part of chia oil, as an oily phase, water as a dispersant, Tween 80 and Kolliphor RH40 as emulsifying agents, propylene glycol as a wetting agent, sodium citrate dihydrate as a buffer and citric acid as a pH adjuster.

Formulation 16 was prepared using coconut oil as an oily phase, water as a dispersant, Tween 80 and Kolliphor RH40 as emulsifying agents, propylene glycol as a wetting agent, sodium citrate dihydrate as a buffer and citric acid as a pH adjuster.

In microemulsion formulations 10, 11, 12, 13, 14, 15 and 16, Tween 80, propylene glycol and Kolliphor RH40 are the surfactants/co-surfactants of the lipid phase, where, in the lipid phase, the Tween 80, the propylene glycol and the Kolliphor RH40 are in a ratio of 1:2:1.5; Kolliphor RH40 and propylene glycol are the surfactants/co-surfactants of the aqueous phase, where, in the aqueous phase, the Kolliphor RH40 and the propylene glycol are in a ratio of 3:1. In the formulations, the surfactants/co-surfactants of the lipid phase are 4.05% (w/v) of the microemulsion, and the surfactants/co-surfactants of the aqueous phase are 1.66% (w/v) of the microemulsion.

Microemulsion for Ophthalmic Use, Formulation 10:

| Components | % w/v |
| --- | --- |
| Castor oil | 0.300 |
| Avocado oil | 0.100 |
| Tween 80 | 0.900 |
| Kolliphor RH40 | 3.045 |
| Propylene glycol | 1.765 |
| Sodium citrate dihydrate | 0.500 |
| Citric acid 0.1N | q.s. pH 7.40 |
| Purified water | q.s. 100 ml |

Microemulsion for Ophthalmic Use, Formulation 11:

| Components | % w/v |
| --- | --- |
| Castor oil | 0.300 |
| *Oryza sativa* oil | 0.100 |
| Tween 80 | 0.900 |
| Kolliphor RH40 | 3.045 |
| Propylene glycol | 1.765 |
| Sodium citrate dihydrate | 0.500 |
| Citric acid 0.1N | q.s. pH 7.40 |
| Purified water | q.s. 100 ml |

Microemulsion for Ophthalmic Use, Formulation 12:

| Components | % w/v |
| --- | --- |
| Castor oil | 0.300 |
| Grape seed oil | 0.100 |
| Tween 80 | 0.900 |
| Kolliphor RH40 | 3.045 |
| Propylene glycol | 1.765 |
| Sodium citrate dihydrate | 0.500 |
| Citric acid 0.1N | q.s. pH 7.40 |
| Purified water | q.s. 100 ml |

Microemulsion for Ophthalmic Use, Formulation 13:

| Components | % w/v |
| --- | --- |
| Krill oil | 0.300 |
| Borage oil | 0.100 |
| Tween 80 | 0.900 |
| Kolliphor RH40 | 3.045 |
| Propylene glycol | 1.765 |
| Sodium citrate dihydrate | 0.500 |
| Citric acid 0.1N | q.s. pH 7.40 |
| Purified water | q.s. 100 ml |

Microemulsion for Ophthalmic Use, Formulation 14:

| Components | % w/v |
| --- | --- |
| Krill oil | 0.300 |
| Linseed oil | 0.100 |
| Tween 80 | 0.900 |
| Kolliphor RH40 | 3.045 |
| Propylene glycol | 1.765 |
| Sodium citrate dihydrate | 0.500 |
| Citric acid 0.1N | q.s. pH 7.40 |
| Purified water | q.s. 100 ml |

Microemulsion for Ophthalmic Use, Formulation 15:

| Components | % w/v |
| --- | --- |
| Krill oil | 0.300 |
| Chia oil | 0.100 |
| Tween 80 | 0.900 |
| Kolliphor RH40 | 3.045 |
| Propylene glycol | 1.765 |
| Sodium citrate dihydrate | 0.500 |
| Citric acid 0.1N | q.s. pH 7.40 |
| Purified water | q.s. 100 ml |

Microemulsion for Ophthalmic Use, Formulation 16:

| Components | % w/v |
| --- | --- |
| Coconut oil | 0.400 |
| Tween 80 | 0.900 |
| Kolliphor RH40 | 3.045 |
| Propylene glycol | 1.765 |
| Sodium citrate dihydrate | 0.500 |
| Citric acid 0.1N | q.s. pH 7.40 |
| Purified water | q.s. 100 ml |

Table 1 summarizes the ratio between surfactants/co-surfactants in the lipid phase, and the ratio between the surfactants/co-surfactants in the aqueous phase for each of formulations described in this example. For example, in formulation 1, there is one surfactant, Tween 80, and one co-surfactant, propylene glycol in the lipid phase; the amount of Tween 80/the amount of propylene glycol is 2:1.

TABLE 1

Ratio surfactants/co-surfactants in the lipid and aqueous phases

| Formulations | Phases | Surfactants/co-surfactants | | |
|---|---|---|---|---|
| | | Tween 80 | Kolliphor RH 40 | Propylene glycol |
| 1, 5 | Lipid | 2 | — | 1 |
| | Aqueous | — | 3 | 1 |
| 2, 3, 4, 6, 7, 8, 9, 10, 11, 12, 13, 14, 15 and 16 | Lipid | 1 | 2 | 1.5 |
| | Aqueous | — | 3 | 1 |

Example 2

Influence of Formulation Composition on Microemulsion Parameters and Relative Chemical and Physical Stability Stress tests were performed on Formulation 1, as described in Example 1, and in its variations subsequently described herein to determine chemical and physical stability.

Formulation 1 was varied using different buffers in amounts and combinations as set forth Table 2.

TABLE 2

| Formulation 1 and relative variations | Total Oily Phase (w/v %) | Sodium citrate (w/v %) | Histidine (w/v %) | Citric Acid 0.1N | Total Aqueous Phase (w/v %) |
|---|---|---|---|---|---|
| 1 | 4.45 | 0.50 | — | q.s. pH 7.4 | q.s. 100% |
| 1.1 | 4.45 | 1.00 | — | q.s. pH 7.4 | q.s. 100% |
| 1.2 | 4.45 | 1.00 | 0.05 | — | q.s. 100% |
| 1.3 | 4.45 | 1.40 | 0.05 | — | q.s. 100% |

Figure 3A:
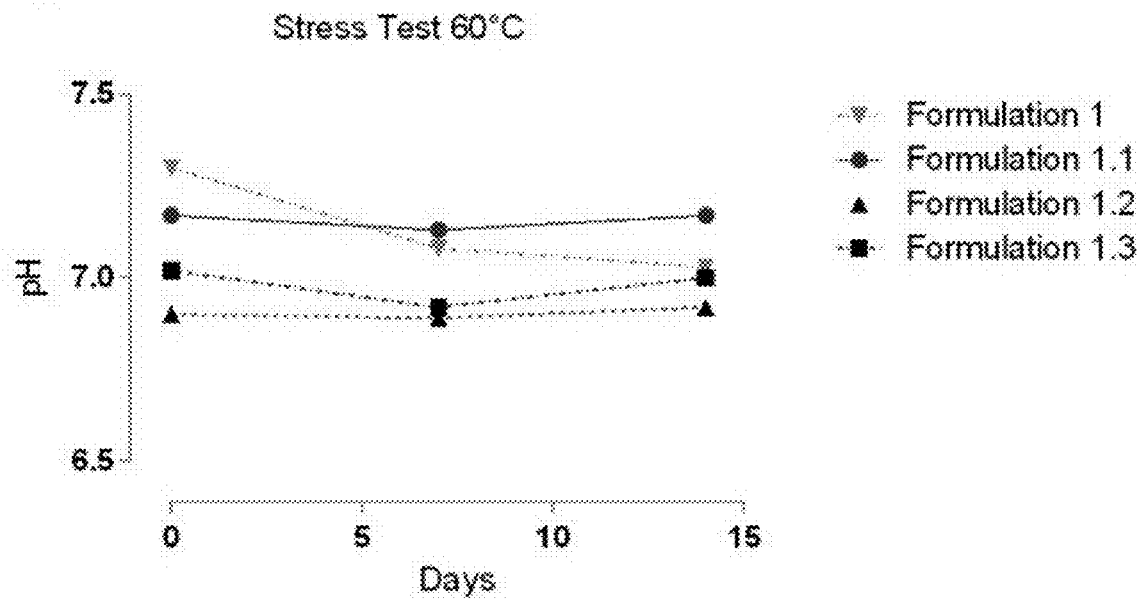
FIGS. 3A-3D depict stability data after stress tests carried out on illustrative formulations of the microemulsions provided herein. For example.
Figure 3B:
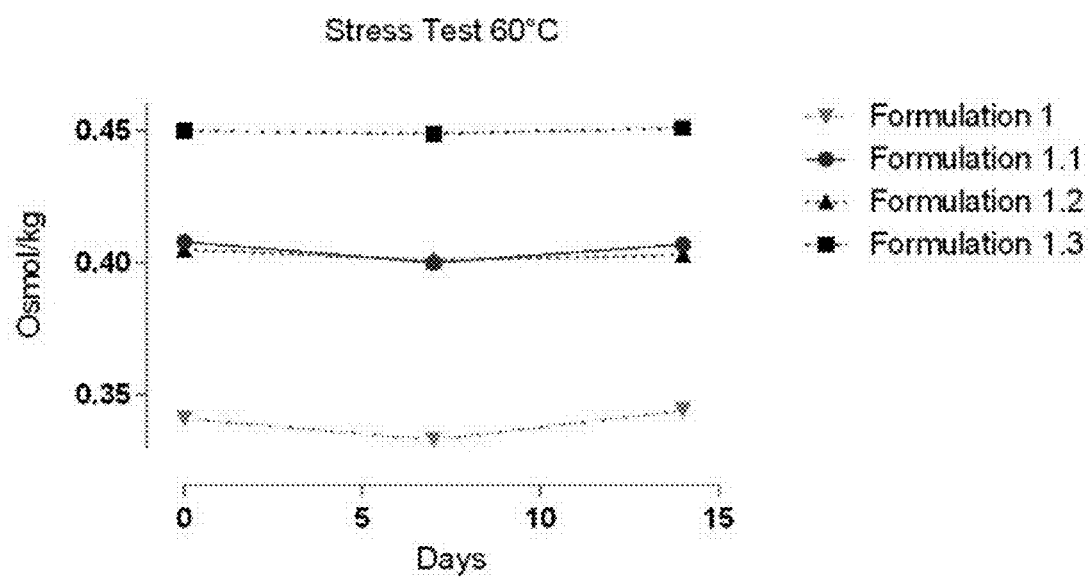
Figure 3C:
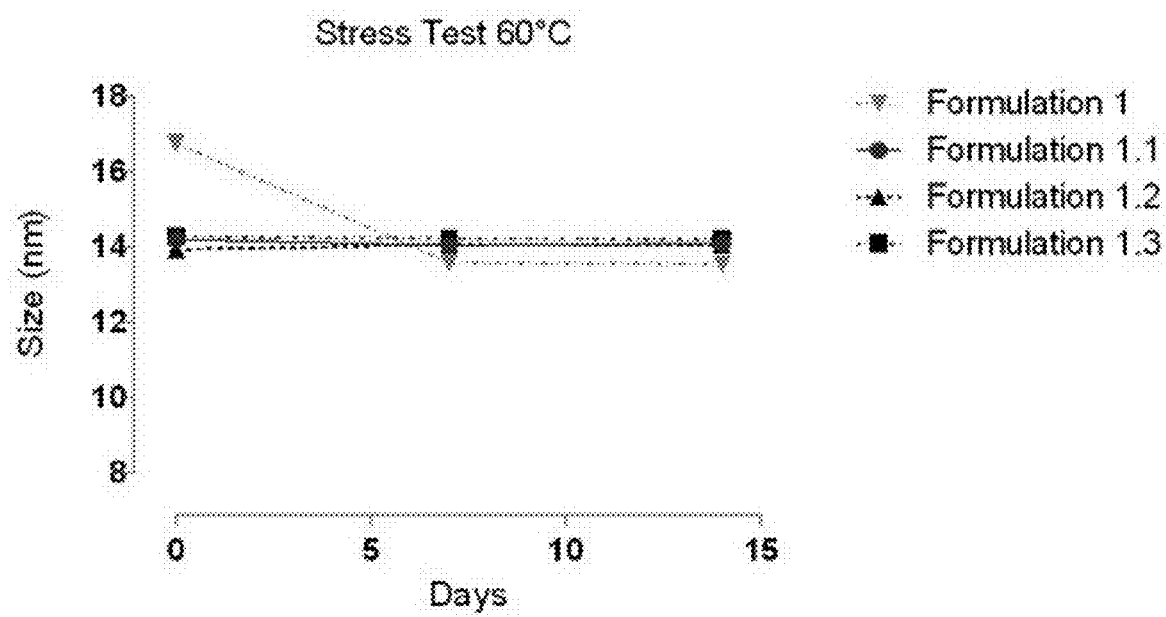
Figure 3D:
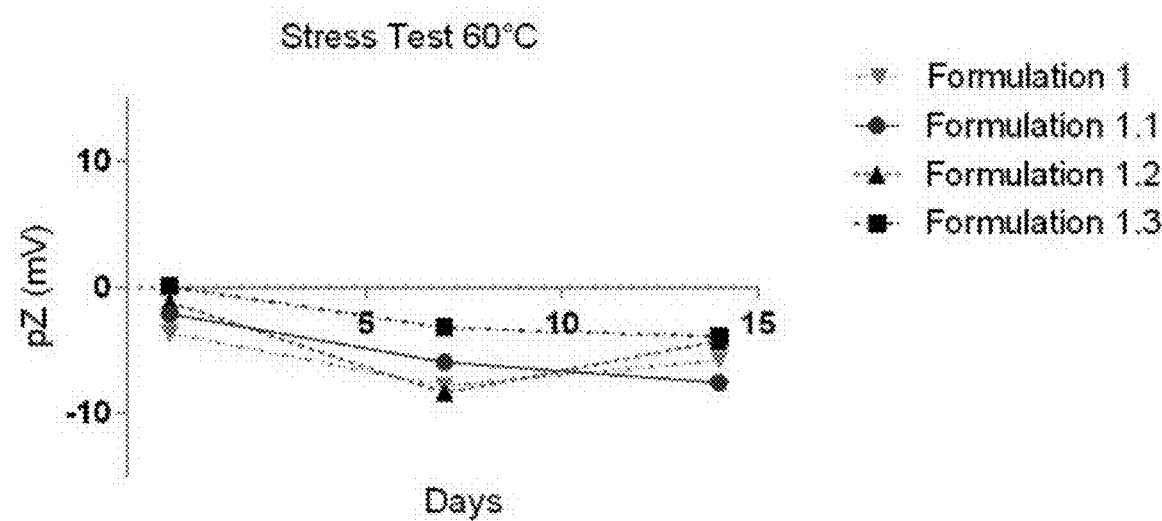

The stability data obtained in conditions of thermal shock at 60° C., for 15 days, are shown in FIGS. 3A-3D and concern: pH (FIG. 3A), osmolality (FIG. 3B), average particle size (size, FIG. 3C) and Zeta potential (pZ, FIG. 3D). From the parameters studied and the results (FIGS. 3A-3D), microemulsion formulation 1, and each of its variations, showed a good stability profile. Of the four microemulsions variants (i.e., 1, 1.1., 1.2 and 1.3), formulation 1, because of its lower citrate buffer concentration, was selected as the most suitable for ophthalmic use and used as a base for further developments and comparisons.

Varying the ratios between the oily phase and the aqueous phase, and the ratio between the surfactants and co-surfactants within the oily and aqueous phase outside the ratios described herein, produces formulations that do not have the requisite properties, such as an average particle size less than 30 nm, or the narrow distribution 15±10 nm. For example, Formulation 5, described above, prepared for comparison with microemulsions provided herein, was not formed from aqueous and lipid phases that contained the requisite ratios of surfactants and does not exhibit the advantageous properties of formulations in which the amount of surfactant(s) in each phase meet the requisite criteria. Table 3 summarizes differences between microemulsion formulation 1 and formulation 5. Formulation 5 is not within the parameters of the microemulsions provided herein; it is described herein for the purpose of comparison.

TABLE 3

| Component | Formulation 1 (%)(w/v) | Formulation 5 Quantity(%)(w/v) |
|---|---|---|
| Oily component | 0.40 | 0.50 |
| Lipid phase surfactants | 4.05 | 5.08 |
| Surfactants in aqueous phase | 1.66 | 2.62 |
| Dispersant phase | q.s. to 100 ml | q.s. to 100 ml |

Specifically, for formulation 1, the ratio between the oily component of the lipid phase surfactants-co-surfactants in the aqueous phase is equal to 0.24, which is within the range 0.2-1. For formulation 1, the surfactant/co-surfactant ratio in the lipid phase to surfactants/co-surfactants in the aqueous phase is equal to 2.44, which is within the range 2.0-10. Formulation 1 is characterized by an average particle size <20 nm, and a polydispersity index (PDI)<0.10.

For formulation 5, however, the ratio between the oily component/sur-factants-co-surfactants in the aqueous phase is equal to 0.19, and the ratio between surfactants/co-surfactants in the lipid phase/surfactants-co-surfactants in the aqueous phase is equal to 1.93. Formulation 5 is characterized by an average particle size >30 nm, and a PDI>0.40.

Figure 4A:
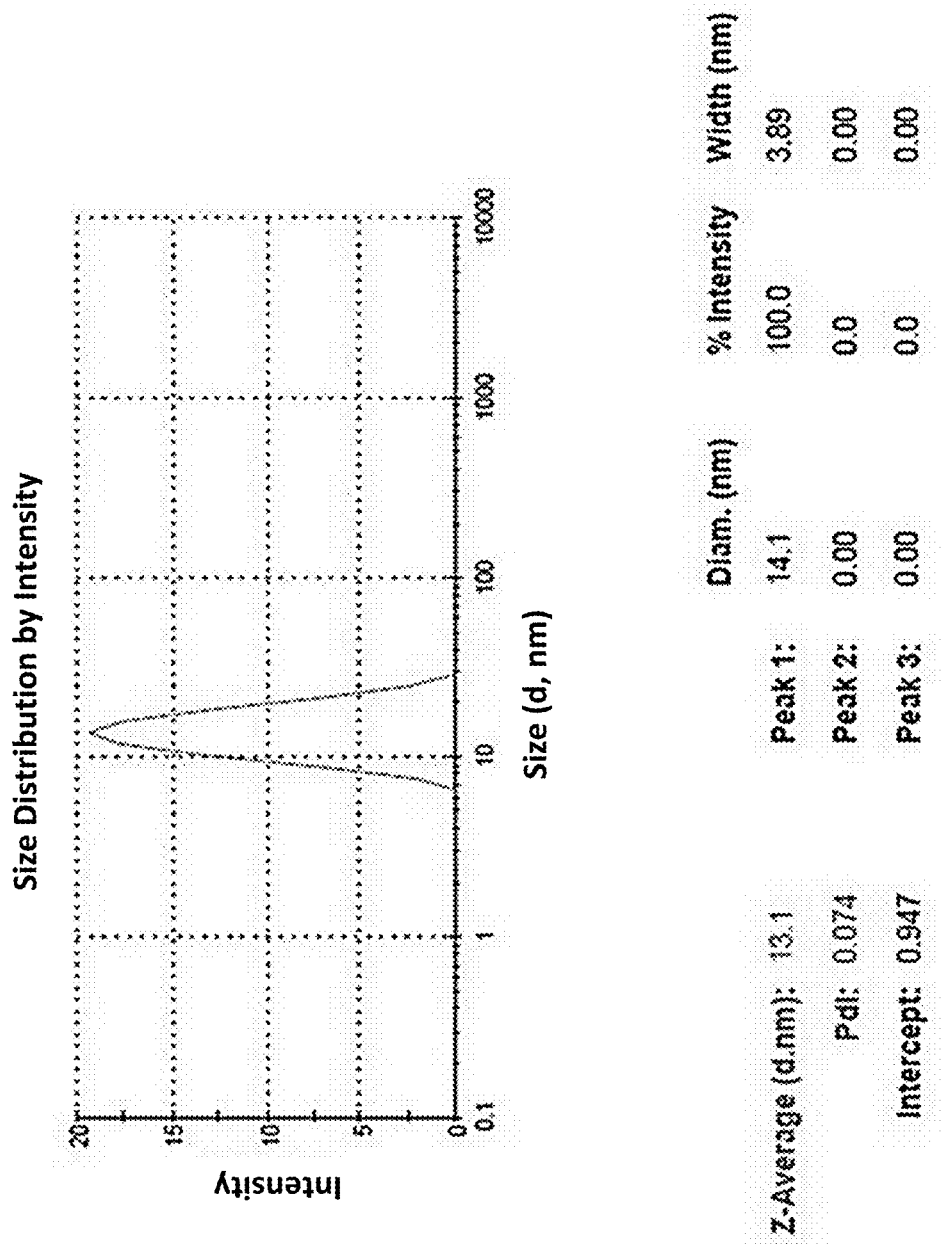
FIGS. 4A and 4B depict the average particle distribution diagrams for formulations 1-(A) and 5-(B).
Figure 4B:
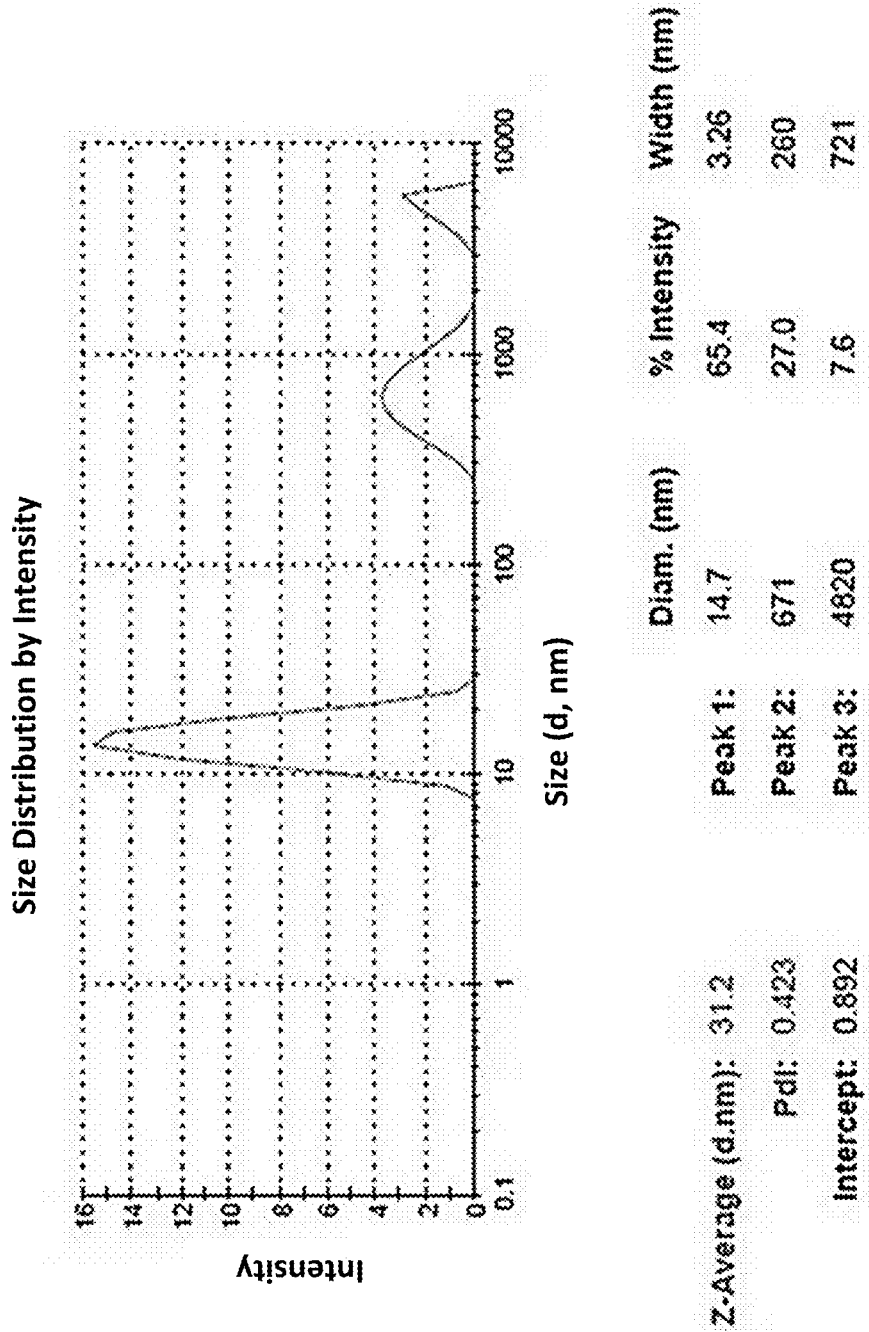
Figure 5A:
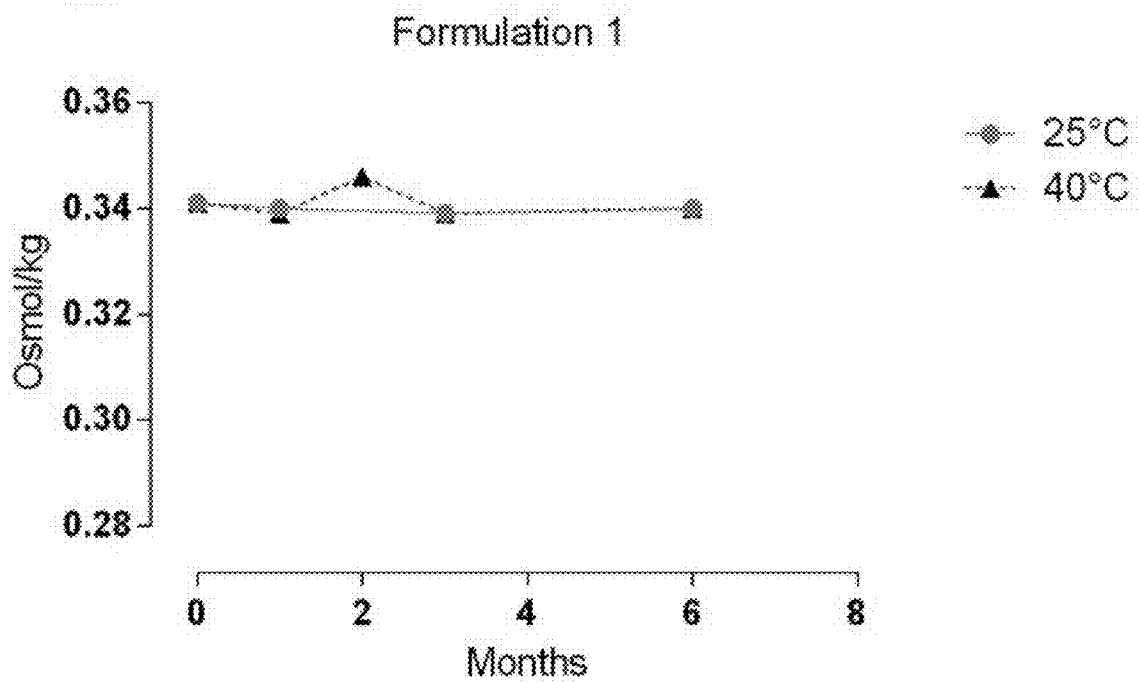
FIGS. 5A-5D depict the stability data at 6 months of an illustrative formulation of the microemulsions provided herein. For example.
Figure 5B:
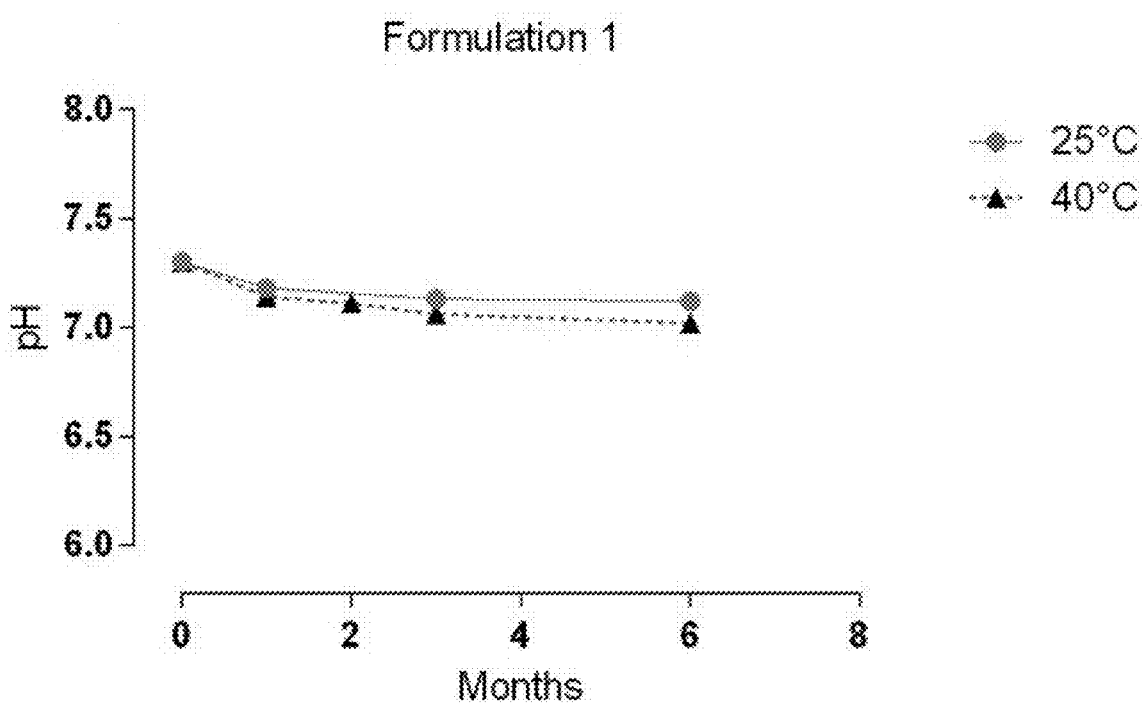
Figure 5C:
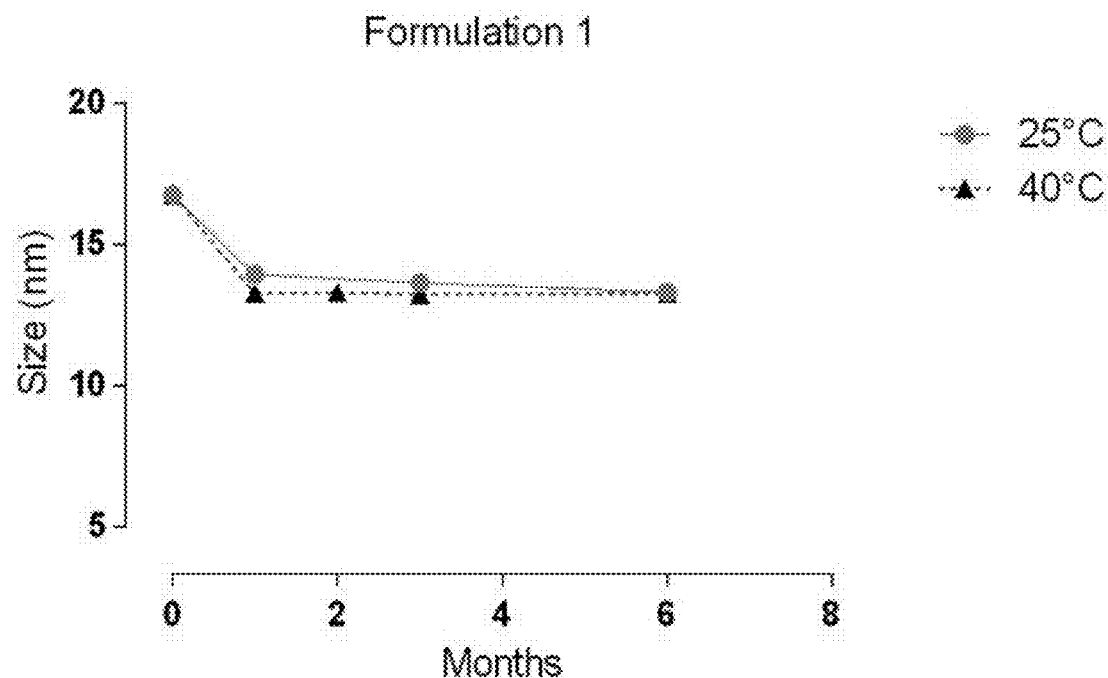
Figure 5D:
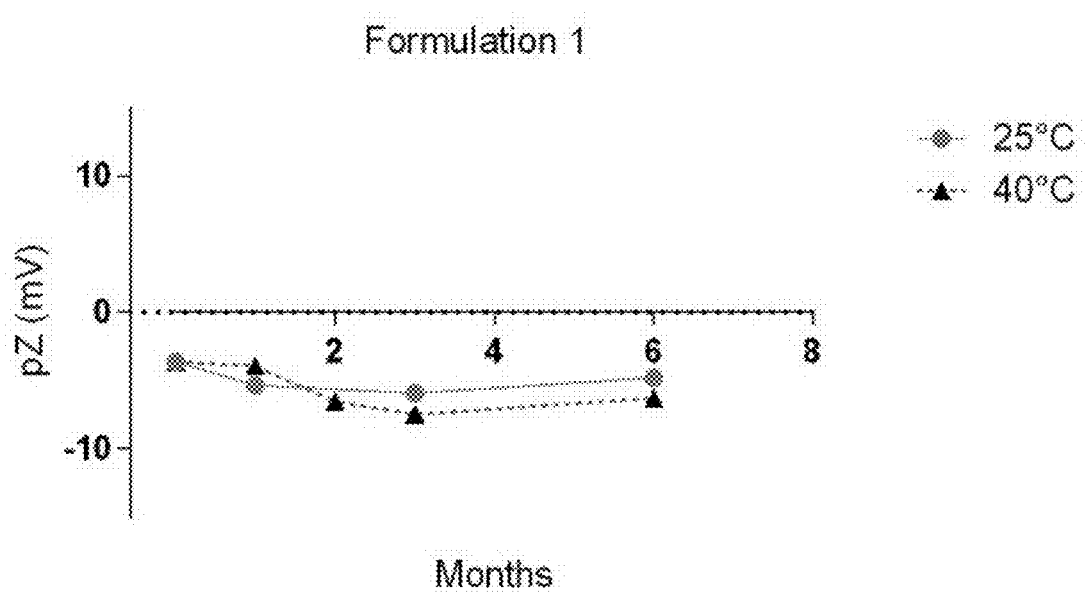

The average particle distribution diagrams (size) for formulation 1 and formulation 5 are shown in FIGS. 4A and 4B, respectively. Formulation 5 appears opalescent and is thermodynamically unstable. In contrast, formulation 1, and its variants described herein, appeared transparent and are thermodynamically stable in the studies carried out for a period of up to 6 months.

FIGS. 5A-5D show the stability data of formulation 1 in time (months) relating to osmolality (FIG. 5A), pH (FIG. 5B), average particle size (nm, FIG. 5C), and Zeta potential (pZ, FIG. 5D) at 25° C. and 40° C. These results show that any deviation from the requisite ratios described herein results in microemulsions that do not have the advantageous properties. Thus, provided are parameters and components for preparing microemulsions that have properties that have not heretofore been observed.

Example 3

Stability of Formulation 4

Figure 6A:
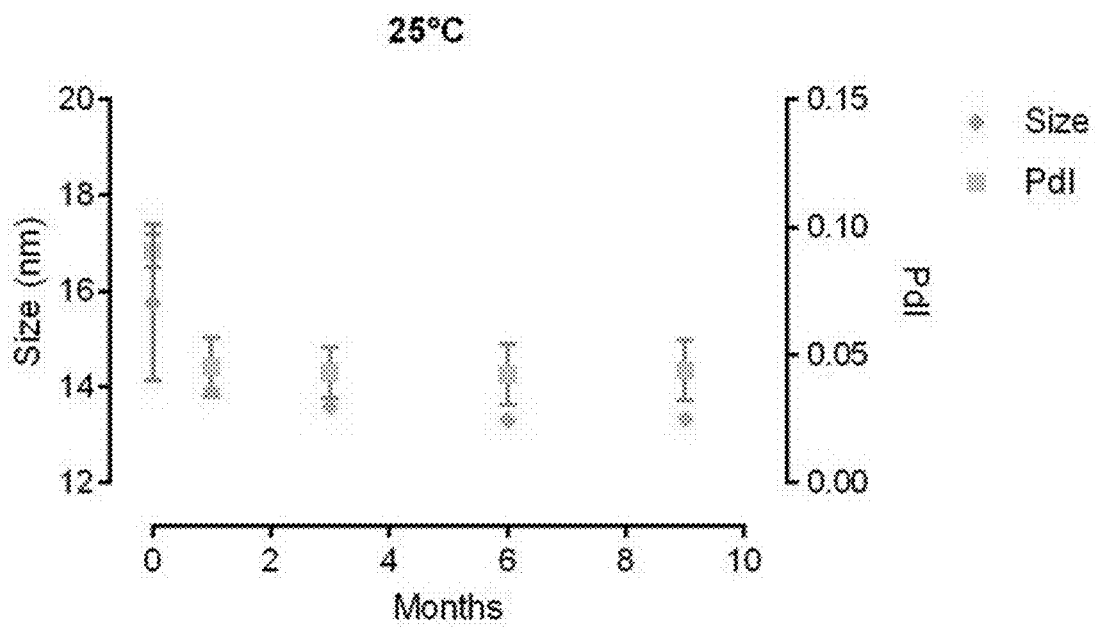
FIGS. 6A-6C depict the stability data of the average particle distribution (size) and the polydispersity index (PDI) at different temperatures, and at different times, of an illustrative formulation of the microemulsions provided herein.
Figure 6B:
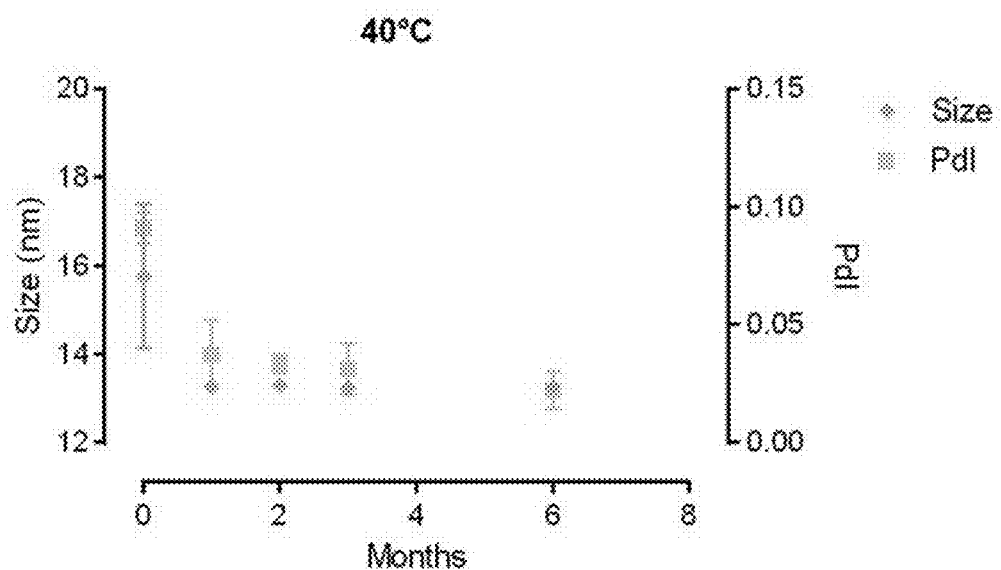
Figure 6C:
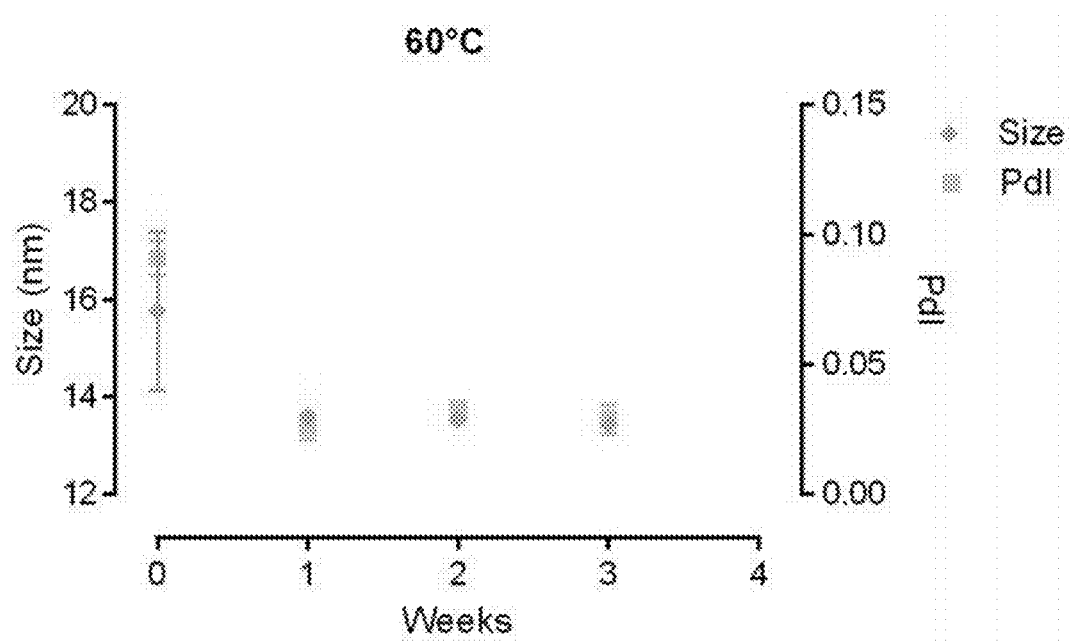
Figure 7A:
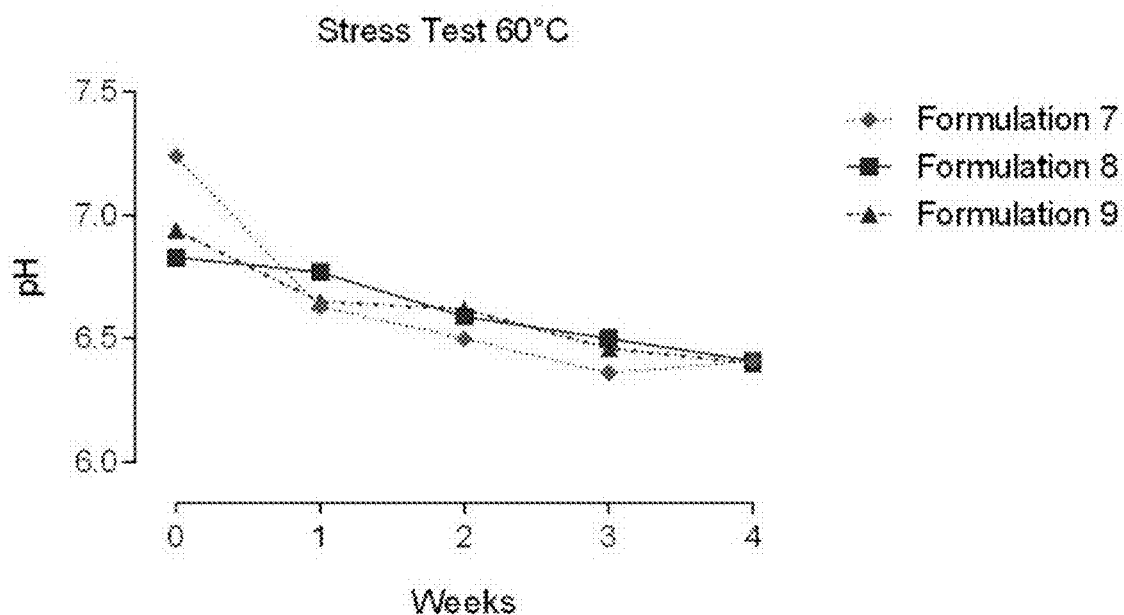
FIGS. 7A-7D depict the stability data after stress tests carried out on illustrative formulations of the microemulsions provided herein. For example.
Figure 7B:
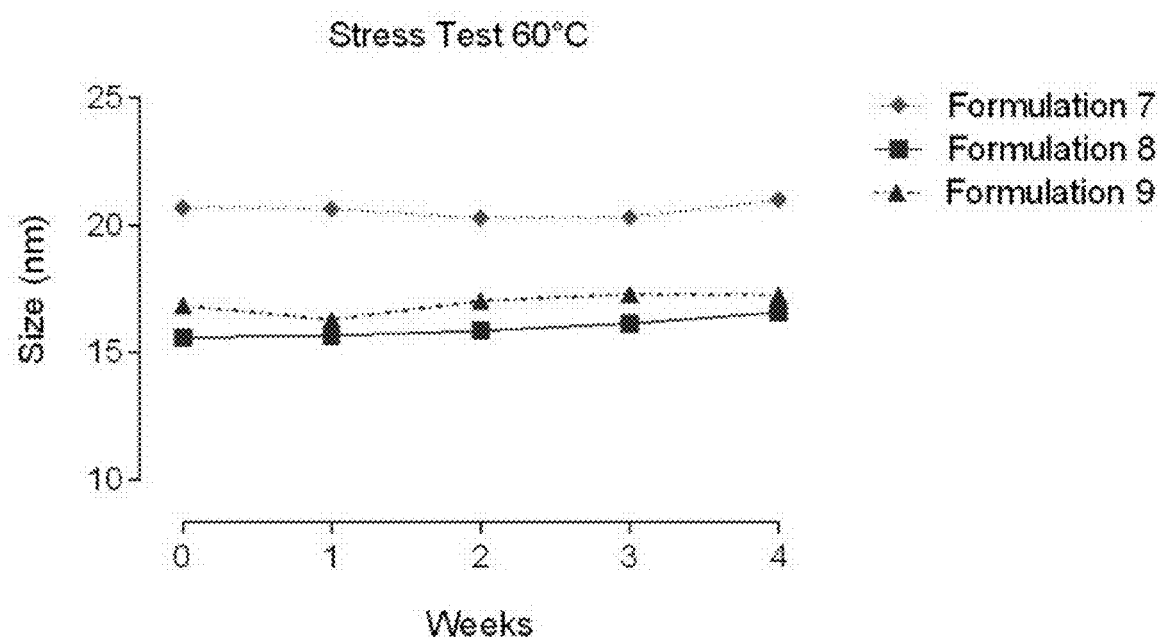
Figure 7C:
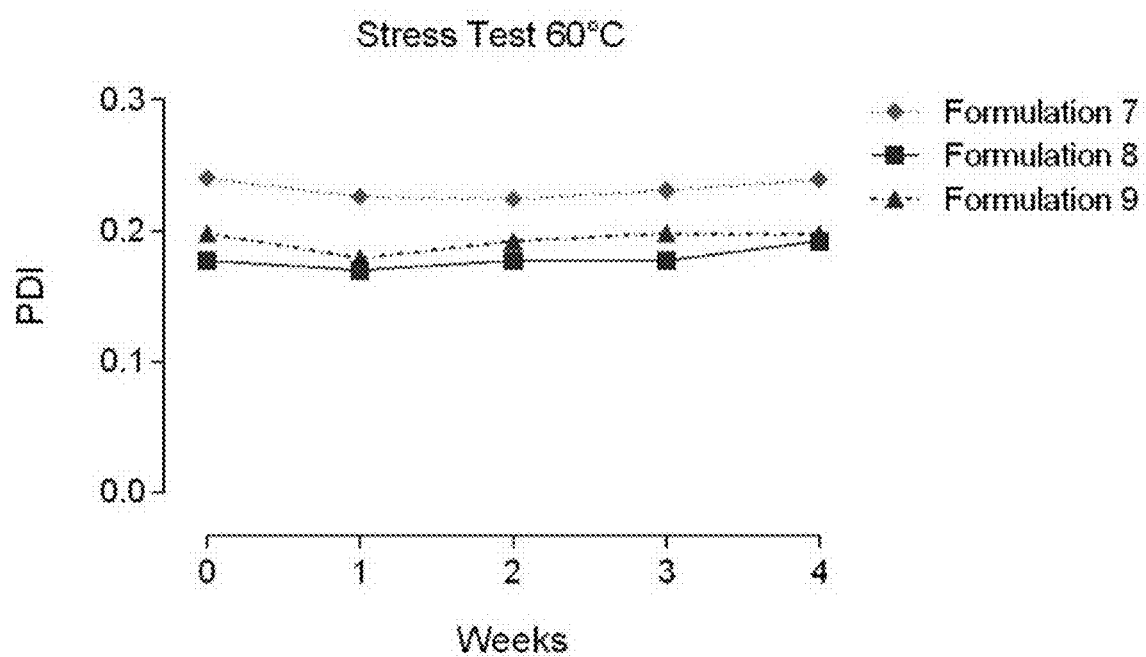
Figure 7D:
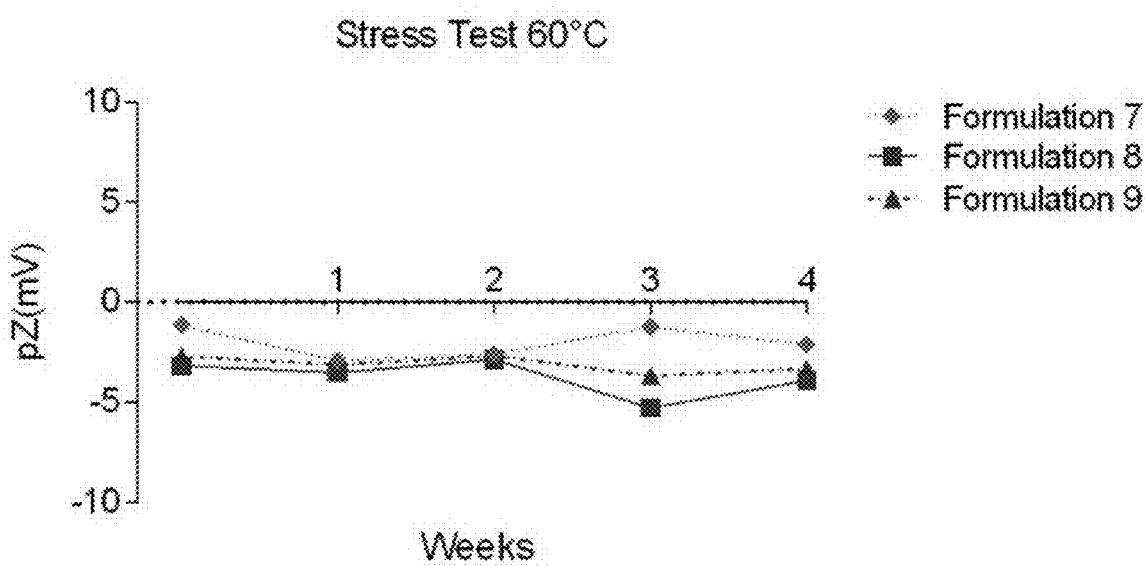
Figure 8A:
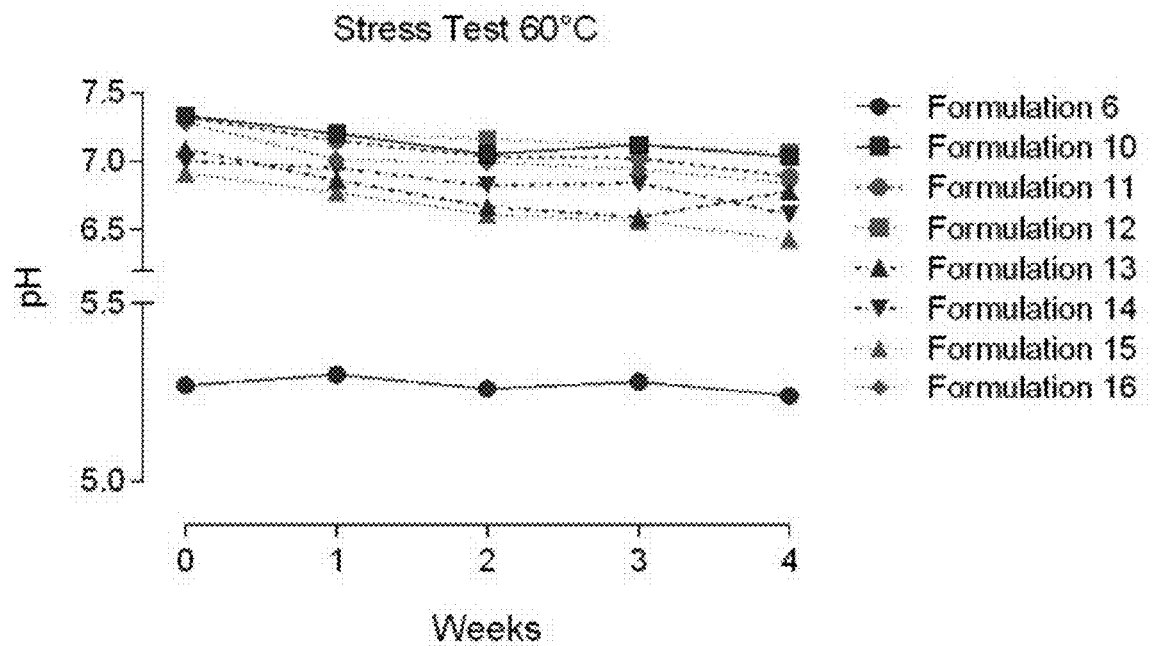
FIGS. 8A-8E depict the stability data after stress tests carried out on illustrative formulations of the microemulsions provided herein. For example.
Figure 8B:
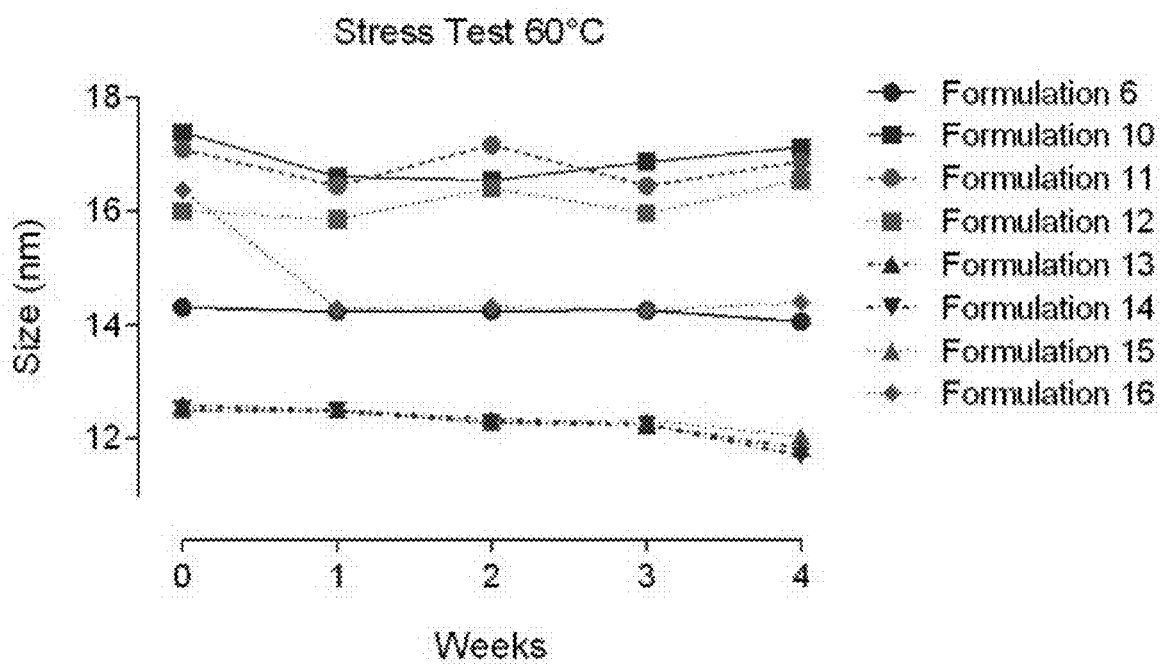
Figure 8C:
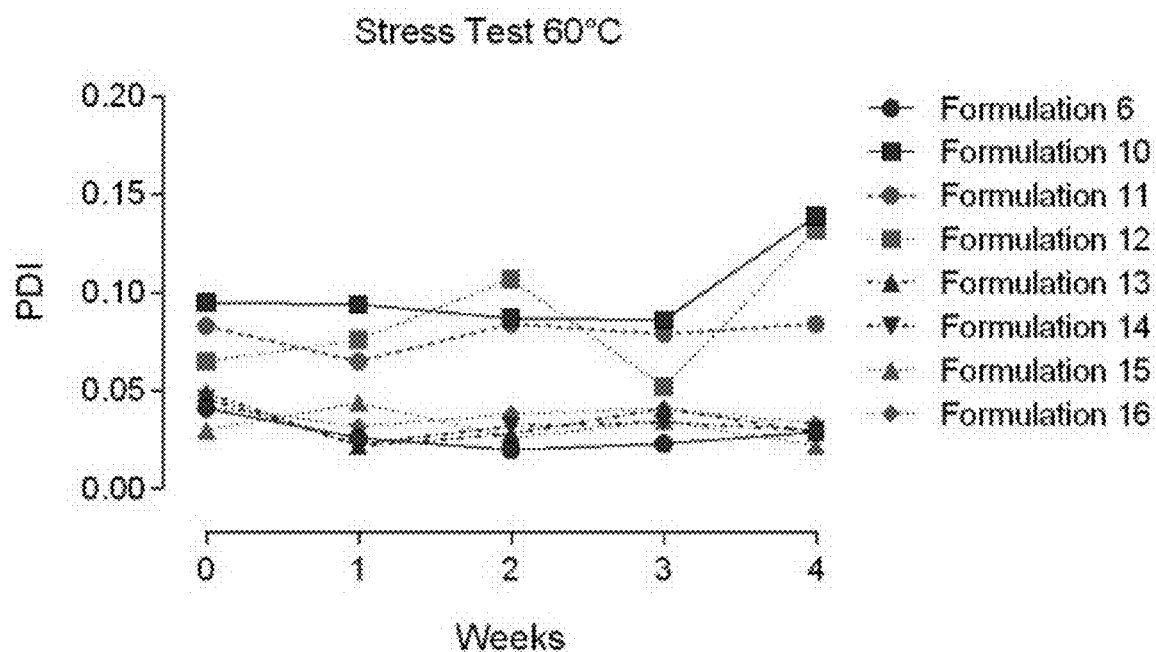
Figure 8D:
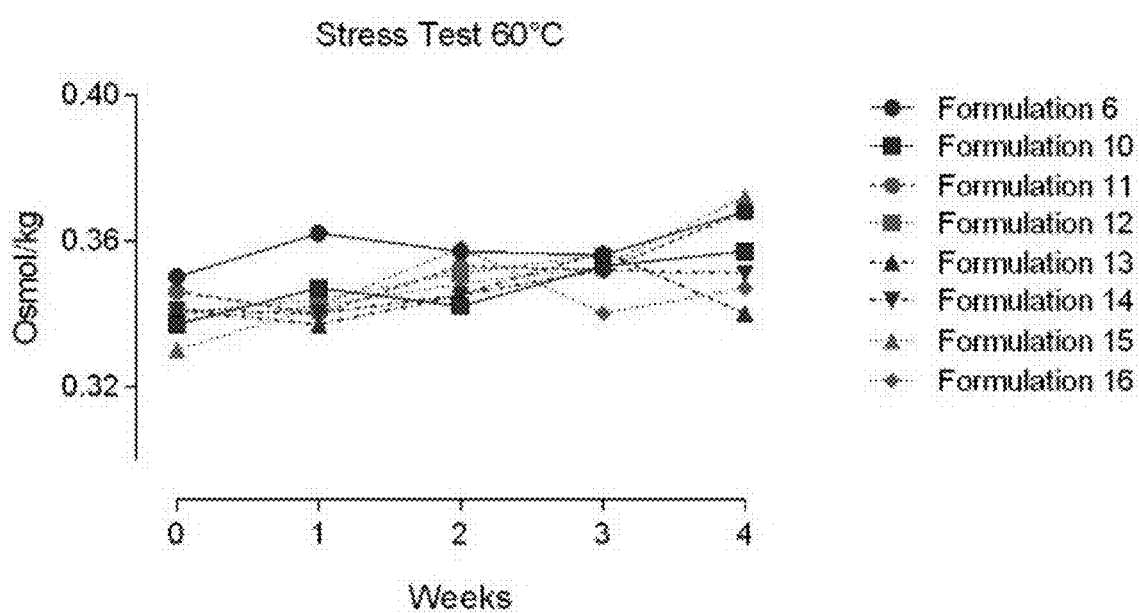
Figure 8E:
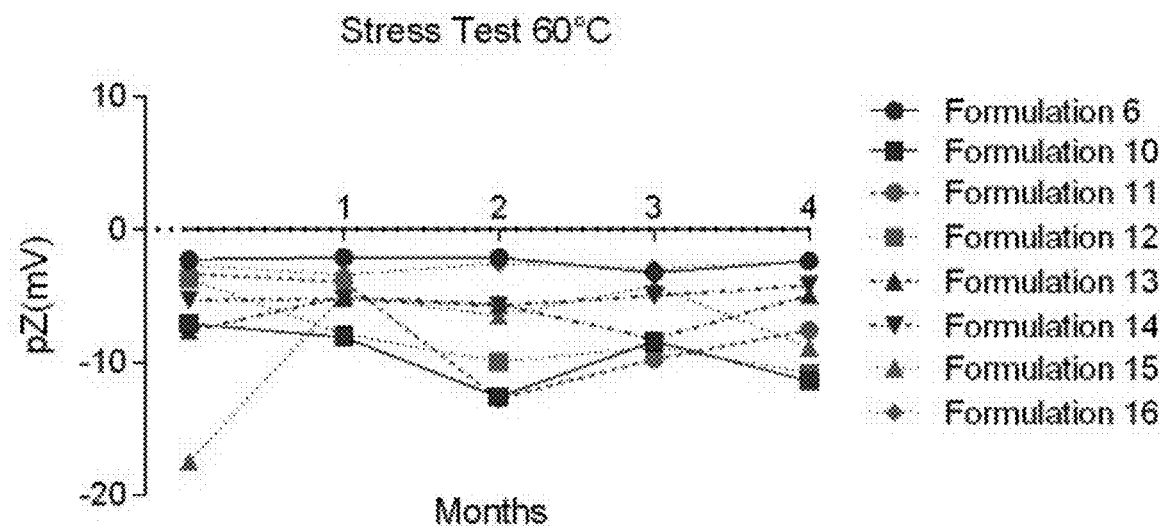

FIGS. 6A-6C show the stability data in time (months) relating to size and the PDI at different temperatures [25° C. (FIG. 6A), 40° C. (Fig. B) and 60° C. (FIG. 6C)] of an illustrative microemulsion formulation provided herein. In each of the conditions analyzed, formulation 4 always presents a size and a PDI within 15±10 nm and 0.070±0.050, respectively. Such values are within the ranges provided herein, and remained constant for the whole study period.

Example 4

Stability of Formulations 7, 8, and 9

Formulations 7, 8, and 9 are characterized by: size s 25 nm; polydispersity index (PDI) s 0.24 and pH value within the range 6.0-7.4.

FIGS. 7A-7D show the stability data of formulations 7, 8 and 9 in time (weeks) relating to pH (FIG. 7A), average particle size (nm, FIG. 7B), polydispersity index (PDI, FIG. 7C) and Zeta potential (mV, FIG. 7D) in conditions of thermal shock at 60° C., for 30 days.

In the condition analyzed, all formulations always show a size and a PDI within the ranges 15±10 nm and 0.190±0.050, respectively. Such values are within the ranges provided herein, and remain constant for the whole study period.

Example 5

Stability of Formulations 6, 10, 11, 12, 13, 14, 15 and 16

Formulation 6 is characterized by: size <20 nm; polydispersity index (PDI)<0.10 and pH value within the indicated ranges of 5-6.

Formulations 10, 11, 12, 13, 14, 15 and 16 are characterized by: size <20 nm; polydispersity index (PDI)<0.10 and pH value within the indicated ranges of 6.5-7.5.

FIGS. 8A-8E show the stability data in time (weeks) relating to pH (FIG. 8A), average particle size (nm, FIG. 8B), polydispersity index (FIG. 8C), osmolality (FIG. 8D) and Zeta potential (mV, FIG. 8E) in conditions of thermal shock at 60° C., for 30 days.

In the condition analyzed, all formulations always show a size and a PDI within the ranges 15±10 nm and 0.190±0.050, respectively.

Such values are within the range provided herein and remain constant for the whole study period.

Example 6

Exemplary Microemulsions Containing Latanoprost, Masoprocol or Sorafenib Tosylate Formulations that contain a pharmaceutically active compound are designated with a "0" in front of the number. Five formulations, designated 01, 02, 03, 04 and 05, prepared as described herein, contain isopropyl myristate as an oily component, water as a dispersant, Tween 80 and Kolliphor RH40 as emulsifying agents, propylene glycol as a wetting agent, and sodium citrate dihydrate and/or histidine hydrochloride as a buffer.

Four formulations, designated 06, 07, 08 and 09, contain krill oil or coconut oil or 3 parts of krill oil and 1 part of borage oil, as an oily phase, water as a dispersant, Tween 80 and Kolliphor RH40 as emulsifying agents, propylene glycol as a wetting agent, sodium citrate dihydrate and/or histidine hydrochloride as a buffer.

The following tables provide exemplary microemulsions that include an active agent for ophthalmic use.

Microemulsion for Ophthalmic Use, Formulation 01:

| Components | % w/v |
|---|---|
| Latanoprost | 0.005 |
| Isopropyl myristate | 0.400 |
| Tween 80 | 2.700 |
| Kolliphor RH40 | 1.245 |
| Propylene glycol | 1.765 |
| Sodium citrate dihydrate | 0.500 |
| Histidine HCl | 0.015 |
| Purified water | q.s. 100 ml |

Summary Table of Some of the Exemplary Microemulsion Formulations

| Component Amounts w/v % | Target ratios | 3 | 05[c] | 7 | 8 | 5[d] | 1 | 4 |
|---|---|---|---|---|---|---|---|---|
| Oil[a] | | 4 | 1.41 | 1.41 (coconut oil) | 1.41 (krill oil) | 0.5 | 0.4 | 0.4 |
| Tween ® 80 | | 8 | 4.15 | 4.15 | 4.15 | 3.39 | 2.7 | 0.9 |
| Kolliphor ® RH40 | | 19.11 | 11.41 | 11.41 | 11.41 | 1.97 | 1.25 | 3.05 |
| Propylene glycol | | 13.04 | 7.26 | 7.26 | 7.26 | 2.35 | 1.77 | 1.77 |
| Total surfactant(s) and co-surfactant(s) | | 40.15 | 22.82 | 22.82 | 22.82 | 7.71 | 5.71 | 5.71 |
| ratio between surfactant(s) and co-surfactant(s) in the lipid phase and in the aqueous phase[d] | 2-10 | 8.67 | 4.51 | 4.51 | 4.51 | 1.94 | 2.44 | 2.43 |
| weight/volume ratio between oil and the surfactant(s) and co-surfactant(s) in the aqueous phase[d] | 0.2 to 1.0 | 0.96 | 0.34 | 0.34 | 0.34 | 0.19 | 0.24 | 0.24 |
| Stability[b] | | n.d. | n.d. | S | S | NS | S | S |

[a]Oil is Isopropyl myristate unless otherwise indicated
[b]n.d. = not described, S = stable, NS = not stable
[c]Formulation 05 contains a drug -see Example 6
[d]outside the ratios Microemulsion for Ophthalmic Use, Formulation 02:

| Components | % w/v |
|---|---|
| Latanoprost | 0.005 |
| Isopropyl myristate | 0.400 |
| Tween 80 | 2.700 |
| Kolliphor RH40 | 1.245 |
| Propylene glycol | 1.765 |
| Sodium citrate dihydrate | 0.700 |
| Histidine HCl | 0.030 |
| Purified water | q.s. 100 ml |

Microemulsion for Ophthalmic Use, Formulation 03:

| Components | % w/v |
|---|---|
| Latanoprost | 0.005 |
| Isopropyl myristate | 0.400 |
| Tween 80 | 2.700 |
| Kolliphor RH40 | 1.245 |
| Propylene glycol | 1.765 |
| Sodium citrate dihydrate | 0.500 |
| Citric acid 0.1N | q.s. pH 7.40 |
| Purified water | q.s. 100 ml |

Microemulsion for Ophthalmic Use, Formulation 04:

| Components | % w/v |
|---|---|
| Masoprocol | 0.302 |
| Isopropyl myristate | 0.400 |
| Tween 80 | 2.700 |
| Kolliphor RH40 | 1.245 |
| Propylene glycol | 1.765 |
| α-Tocopherol | 0.100 |
| Sodium citrate dihydrate | 0.500 |
| Citric acid 0.1N | q.s. pH 5.50 |
| Purified water | q.s. 100 ml |

In formulations 01, 02, 03 and 04, Tween 80 and propylene glycol are the surfactants/co surfactants of the lipid phase, where, in the lipid phase, the Tween 80 and the propylene glycol are in a ratio of 2:1; Kolliphor RH40 and propylene glycol are the surfactants/co-surfactants of the aqueous phase, where, in the aqueous phase, the Kolliphor RH40 and the propylene glycol are in a ratio of 3:1. In formulation 1, the surfactants/co-surfactants of the lipid phase are 4.05% (w/v) of the microemulsion and the surfactants/co-surfactants of the aqueous phase are 1.66% (w/v) of the microemulsion.

Microemulsion for Ophthalmic Use, Formulation 05:

| Components | % w/v |
|---|---|
| Sorafenib tosylate | 0.300 |
| Isopropyl myristate | 1.410 |
| Tween 80 | 4.150 |
| Kolliphor RH40 | 11.410 |
| Propylene glycol | 7.260 |
| Sodium citrate dihydrate | 0.500 |
| Purified water | q.s. 100 ml |

Microemulsion for Ophthalmic Use, Formulation 05:

| Components | % w/v |
|---|---|
| Masoprocol | 0.302 |
| Krill oil | 0.400 |
| Tween 80 | 0.900 |
| Kolliphor RH40 | 3.045 |
| Propylene glycol | 1.765 |
| α-Tocopherol | 0.100 |
| Resveratrol | 0.050 |
| Sodium citrate dihydrate | 0.500 |
| Citric acid 0.1N | q.s. pH 5.20 |
| Purified water | q.s. 100 ml |

In formulation 06, Tween 80, propylene glycol and Kolliphor RH40 are the surfactants/co-surfactants of the lipid phase, where, in the lipid phase, the Tween 80, the propylene glycol and the Kolliphor RH40 are in a ratio of 1:2:1.5; Kolliphor RH40 and propylene glycol are the surfactants/co-surfactants of the aqueous phase, where, in the aqueous phase, the Kolliphor RH40 and the propylene glycol are in a ratio of 3:1. In the formulations, the surfactants/co-surfactants of the lipid phase are 4.05% (w/v) of the microemulsion and the surfactants/co-surfactants of the aqueous phase are 1.66% (w/v) of the microemulsion.

Microemulsion for Ophthalmic Use, Formulation 07:

| Components | % w/v |
|---|---|
| Sorafenib tosylate | 0.300 |
| Coconut oil | 1.410 |
| Tween 80 | 4.150 |
| Kolliphor RH40 | 11.410 |
| Propylene glycol | 7.260 |
| Sodium citrate dihydrate | 0.500 |
| Purified water | q.s. 100 ml |

Microemulsion for Ophthalmic Use, Formulation 08:

| Components | % w/v |
|---|---|
| Sorafenib tosylate | 0.300 |
| Krill oil | 1.410 |
| Tween 80 | 4.150 |
| Kolliphor RH40 | 11.410 |
| Propylene glycol | 7.260 |
| Sodium citrate dihydrate | 0.500 |
| Purified water | q.s. 100 ml |

Microemulsion for Ophthalmic Use, Formulation 09:

| Components | % w/v |
|---|---|
| Sorafenib tosylate | 0.300 |
| Krill oil | 1.060 |
| Borage oil | 0.350 |
| Tween 80 | 4.150 |
| Kolliphor RH40 | 11.410 |
| Propylene glycol | 7.260 |
| Sodium citrate dihydrate | 0.500 |
| Purified water | q.s. 100 ml |

In formulations 05, 07, 08 and 09, Tween 80, propylene glycol and Kolliphor RH40 are the surfactants/co-surfactants of the lipid phase; in the lipid phase, the Tween 80, the propylene glycol and the Kolliphor RH40 are in a ratio of 1:2:1.5; Kolliphor RH40 and propylene glycol are the surfactants/co-surfactants of the aqueous phase, where, in the aqueous phase, the Kolliphor RH40 and the propylene glycol are in a ratio of 3:1. In these formulations, the surfactants/co-surfactants of the lipid phase are 18.67% (w/v) of the microemulsion and the surfactants/co-surfactants of the aqueous phase are 4.15% (w/v) of the microemulsion (total surfactants/co-surfactants in the resulting microemulsion are 23.83%).

Example 7

Stability of Formulations 01, 02 and 03 of Example 6 Containing Latanoprost

Figure 9A:
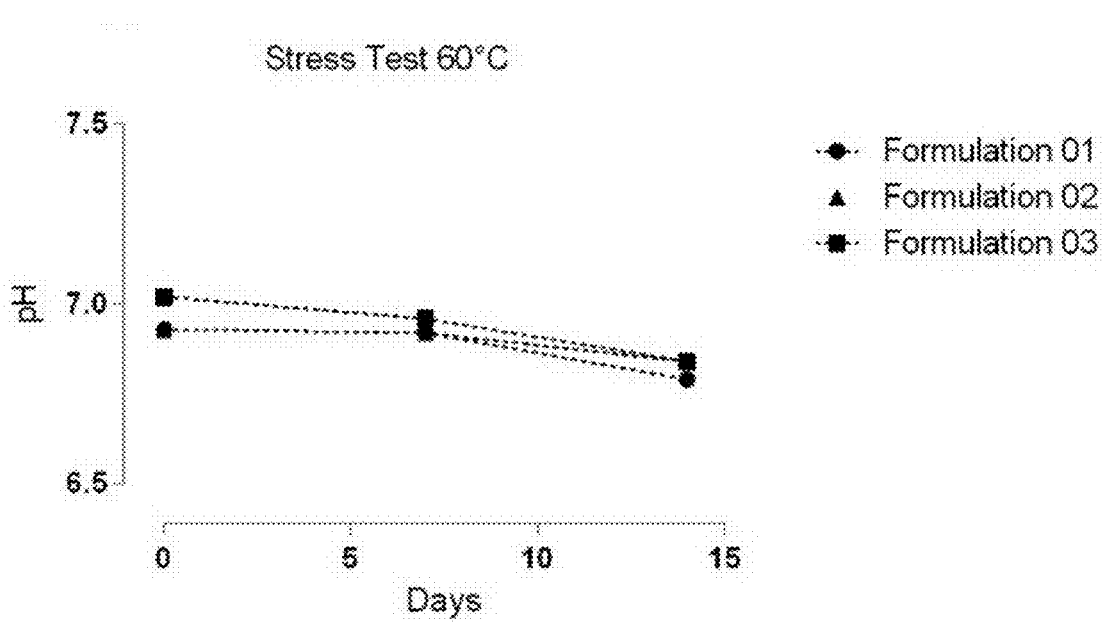
FIGS. 9A-9E depict the stability data after stress tests carried out on illustrative formulations of the microemulsions that contain an active ingredient, such as latanoprost. For example.
Figure 9B:
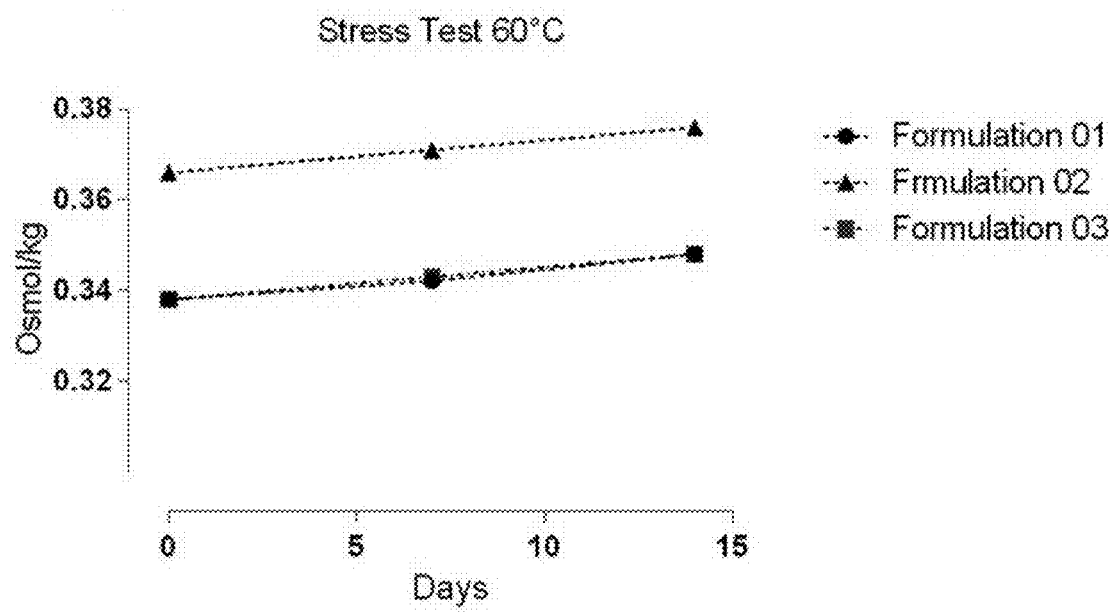
Figure 9C:
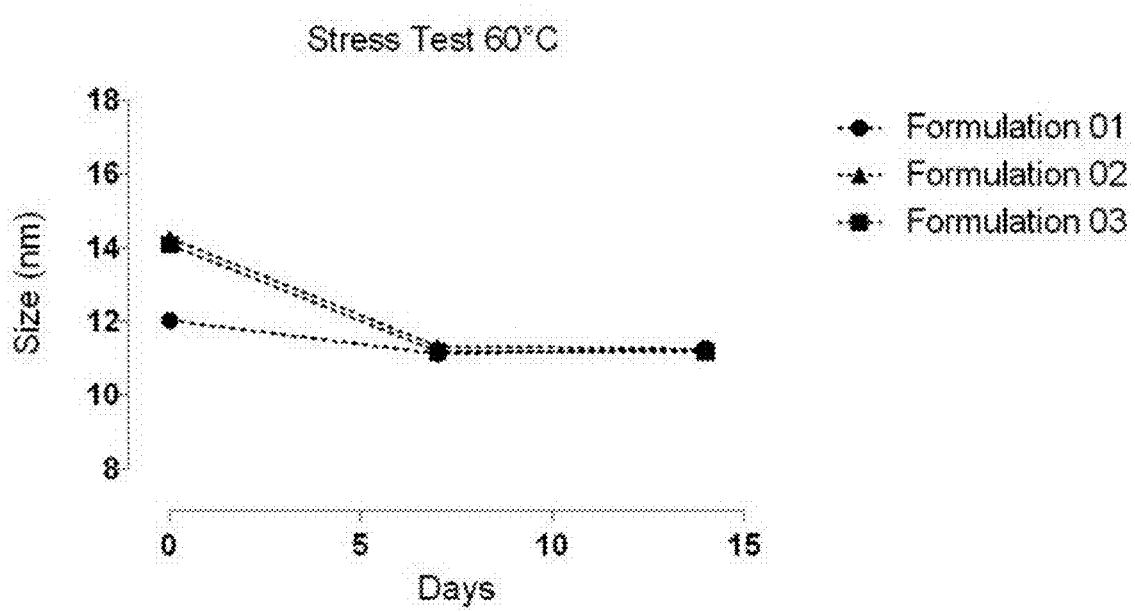
Figure 9D:
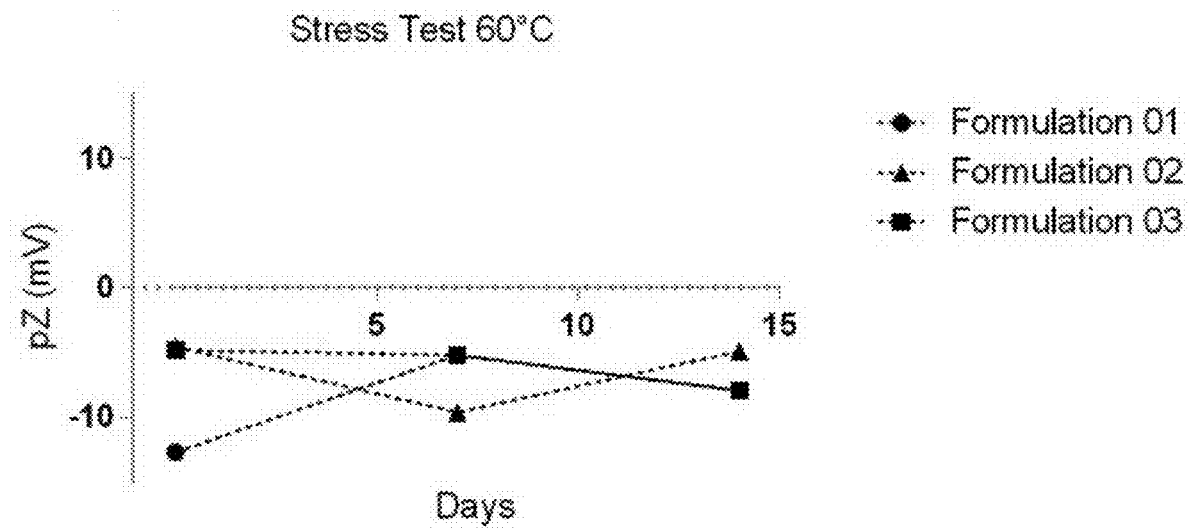
Figure 9E:
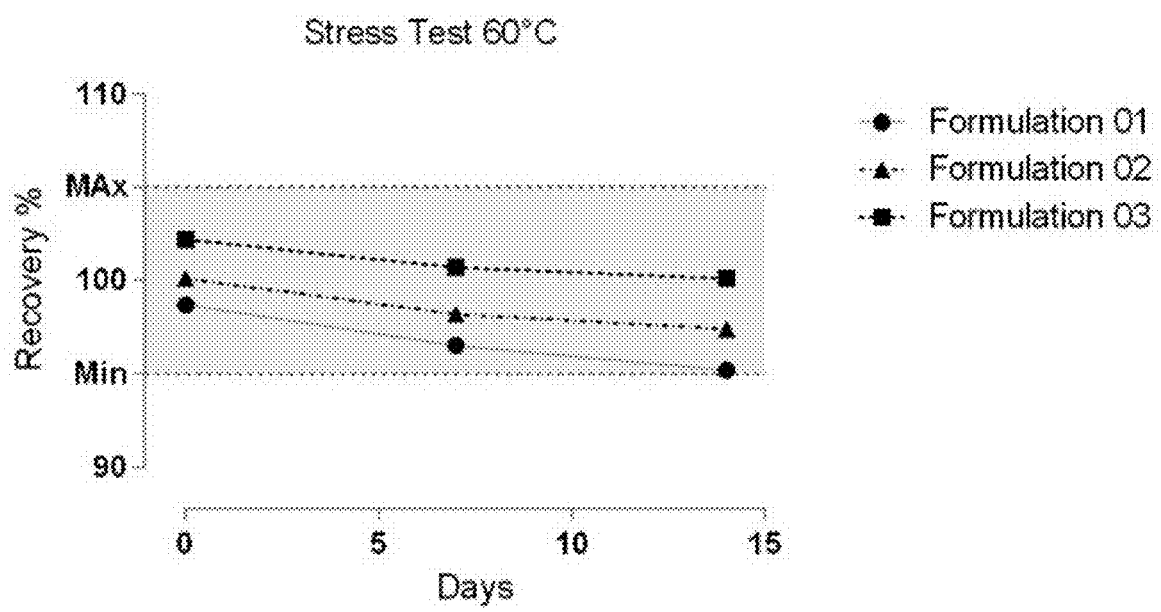

Formulations 01, 02 and 03 as described in Example 6 were subjected to stress tests to evaluate their chemical and physical stability. The stability data obtained in thermal shock conditions at 60° C. for 15 days is shown in FIGS. 9A-9E, which shows: pH (FIG. 9A), osmolality (FIG. 9B), size (FIG. 9C), pZ (FIG. 9D) and percentage of latanoprost recovery (FIG. 9E).

All of the tested formulations were shown to maintain chemical-physical parameters within the specifications during the whole of the study period. Formulation 03 highlighted a low variability in the percentage of latanoprost and an osmolality value more suitable for ophthalmic use.

Figure 10A:
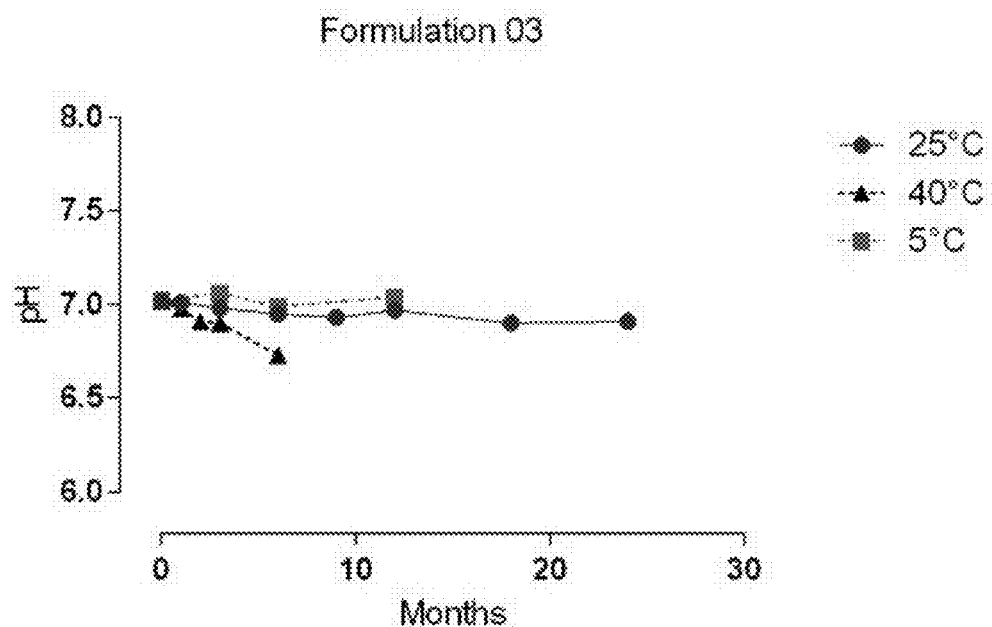
FIGS. 10A-10E depict the stability data at 24 months of an illustrative formulation of the microemulsions that contain an active ingredient, such as latanoprost. For example.
Figure 10B:
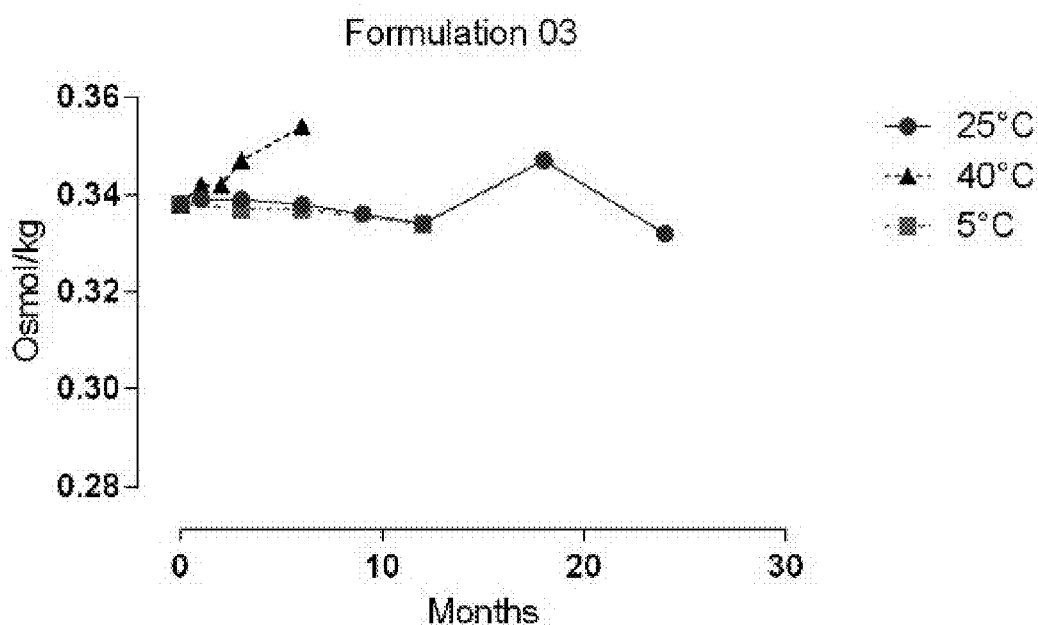
Figure 10C:
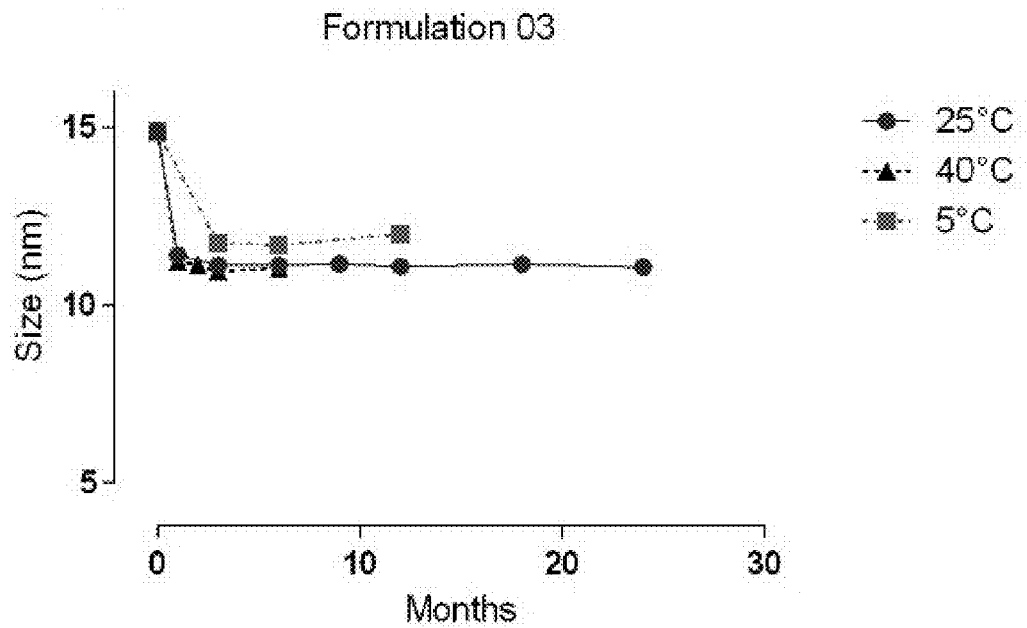
Figure 10D:
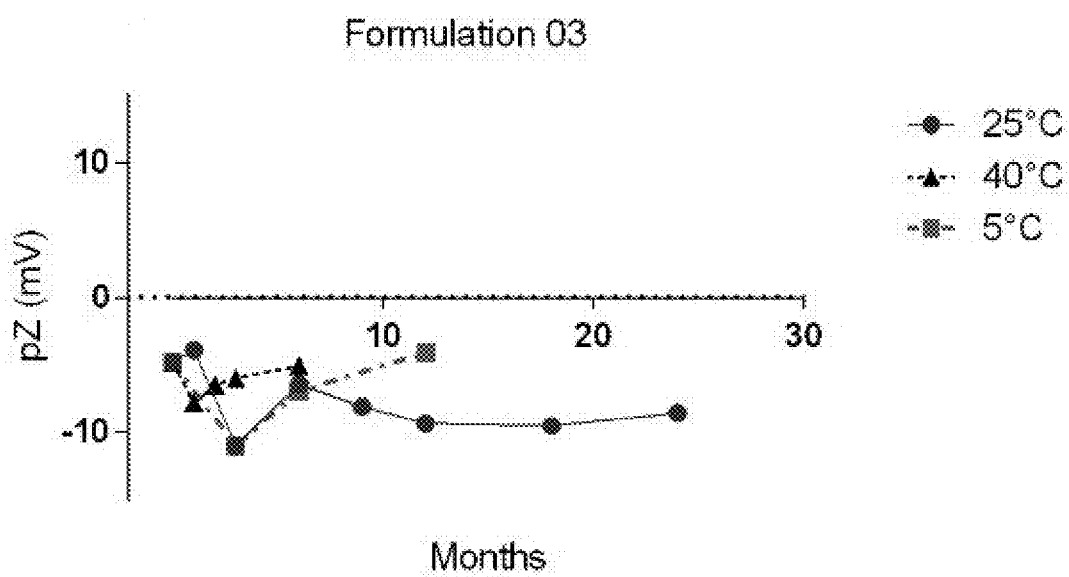
Figure 10E:
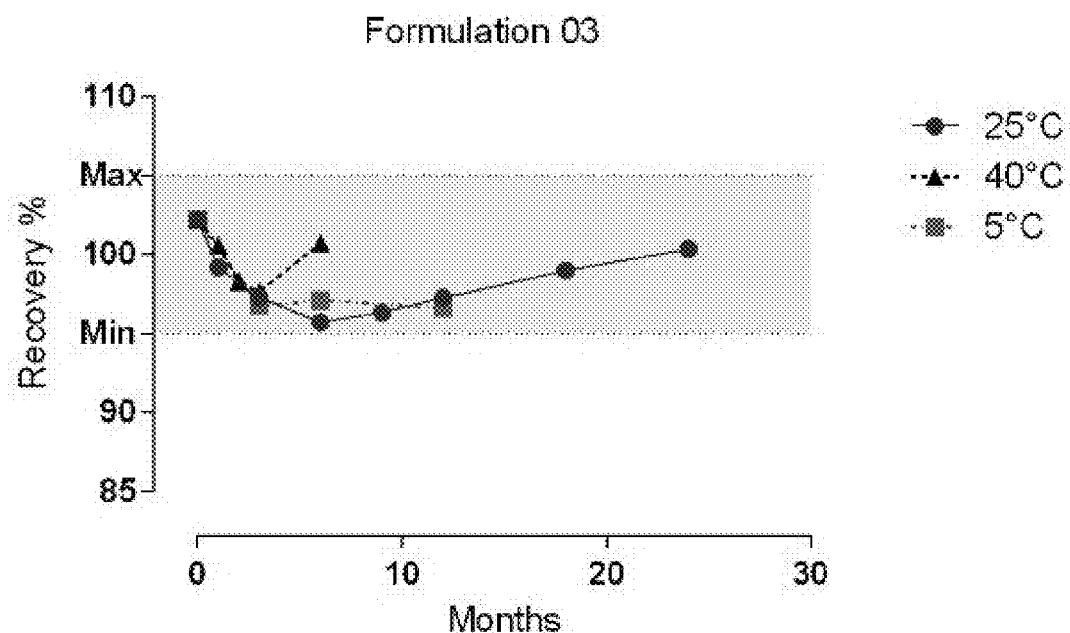
Figure 11A:
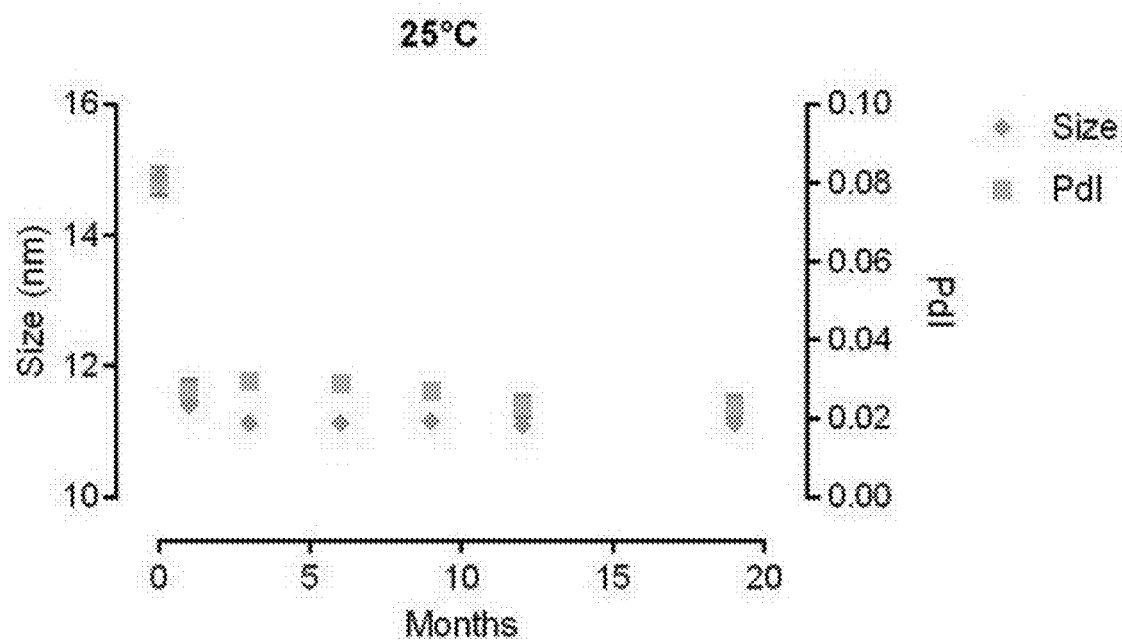
FIGS. 11A-11D depict the stability data of the average particle distribution (size) and the polydispersity index (PDI) at different temperatures, and at different times, of an illustrative formulation of the microemulsions that contain an active ingredient, such as latanoprost.
Figure 11B:
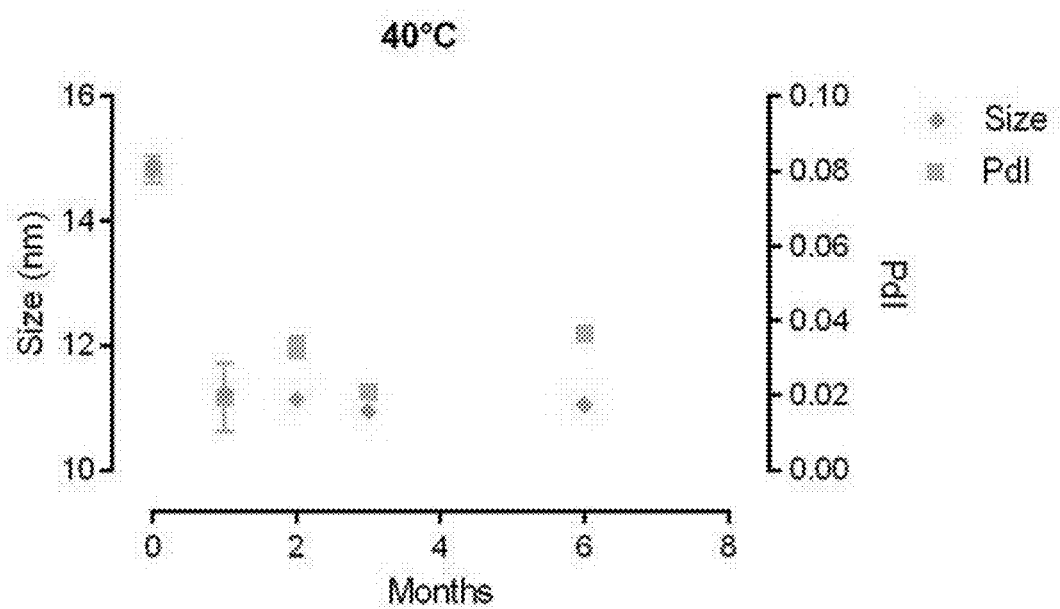
Figure 11C:
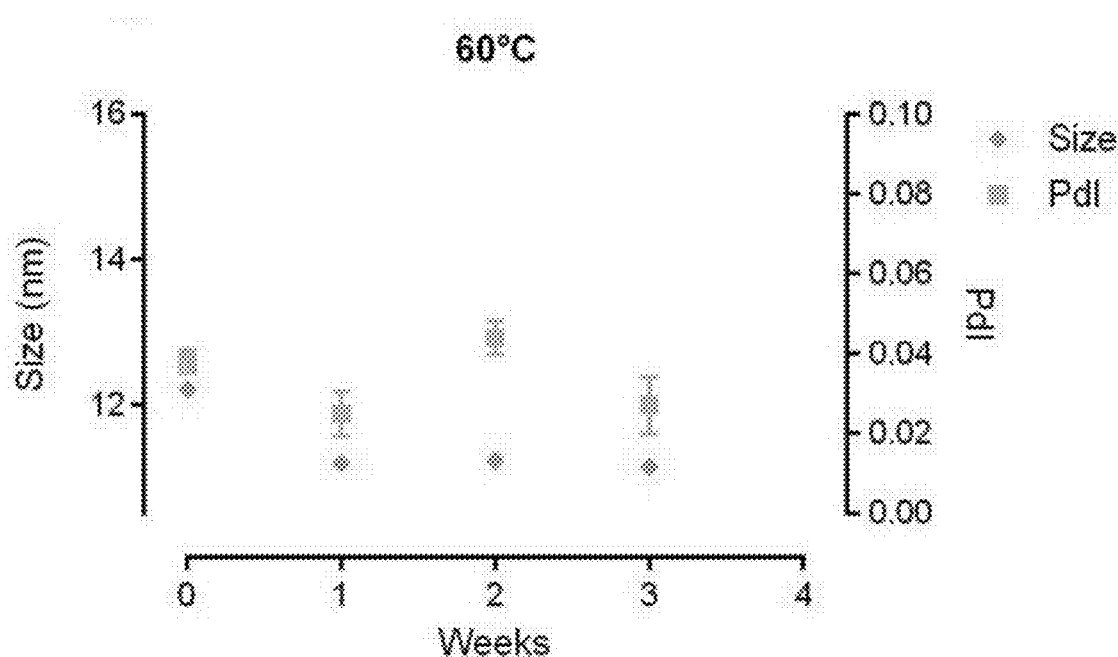
Figure 11D:
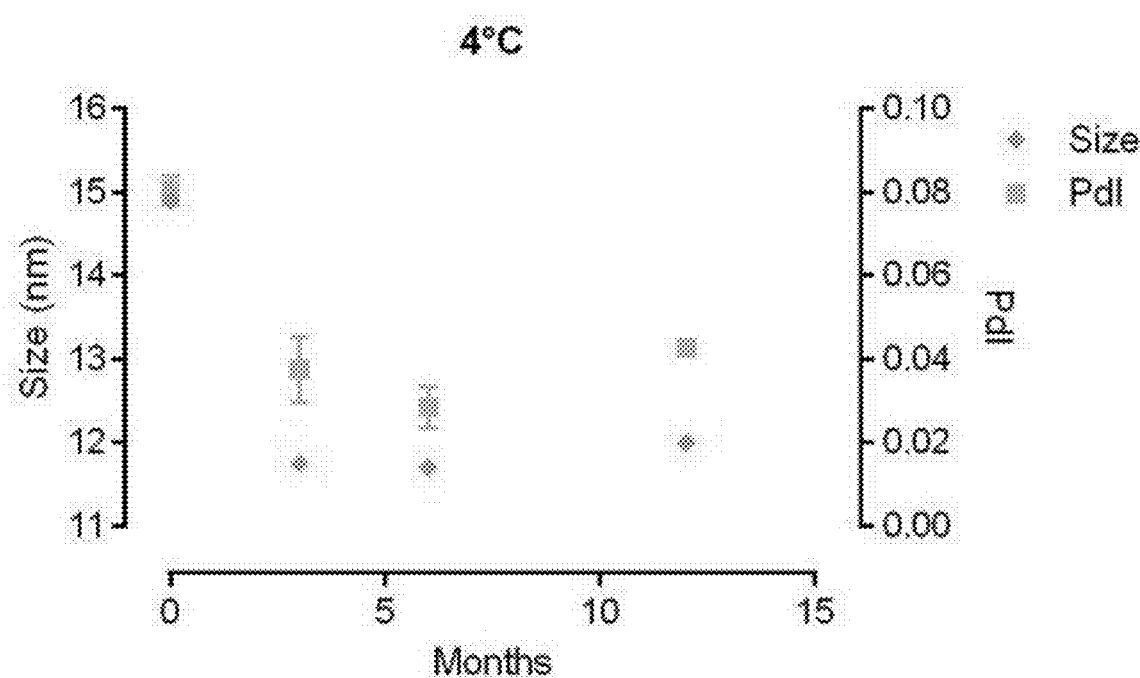
Figure 12A:
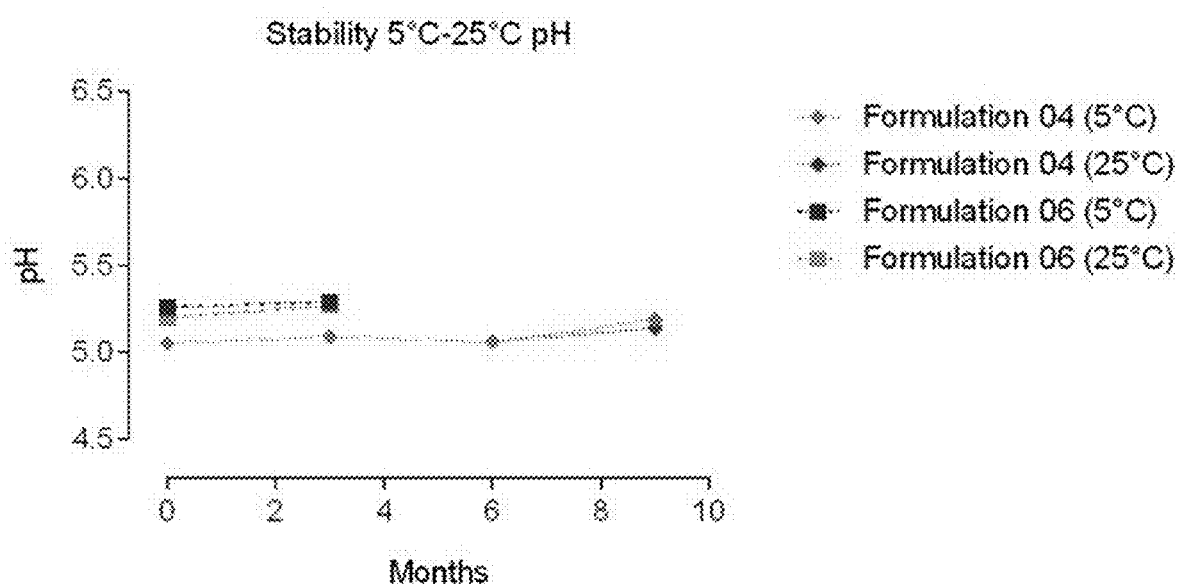
FIGS. 12A-12E depict the stability data at 3 and 9 months of illustrative formulations of the microemulsion that contain an active ingredient, such as masoprocol. For example.
Figure 12B:
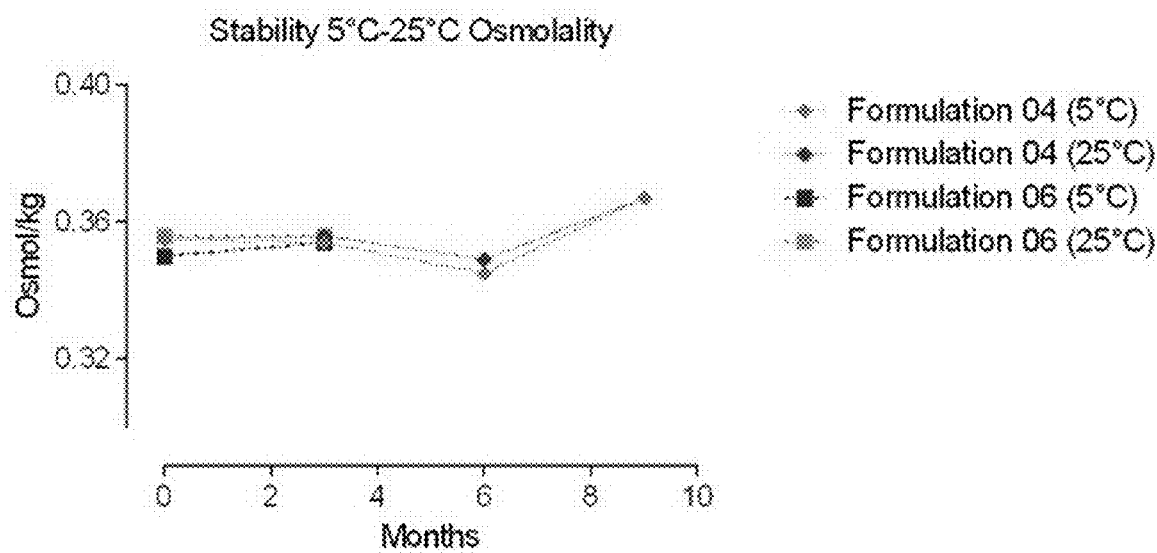
Figure 12C:
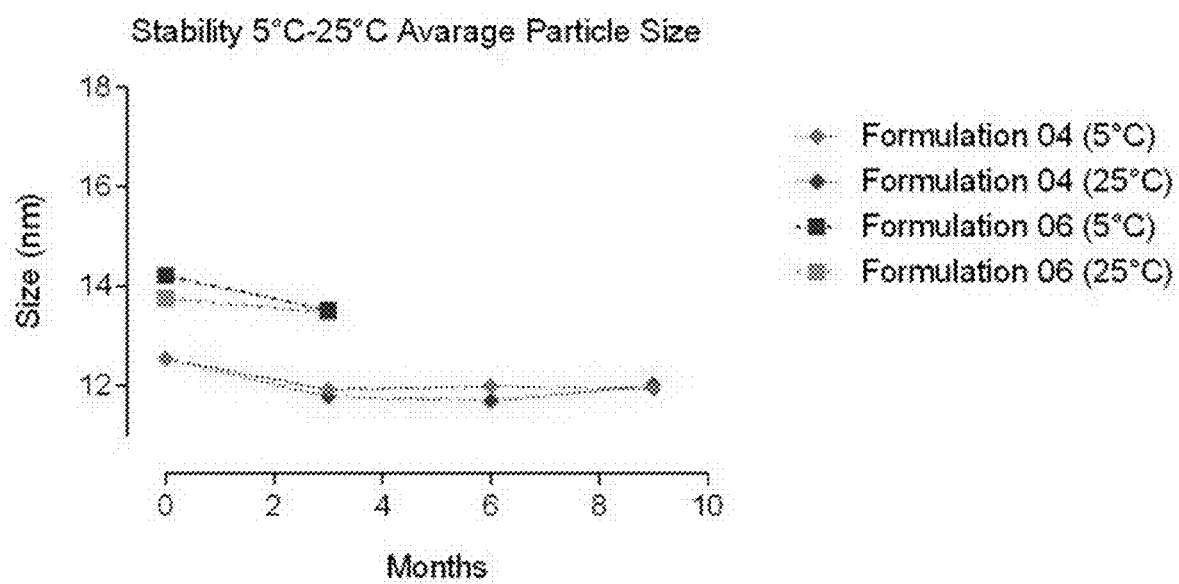
Figure 12D:
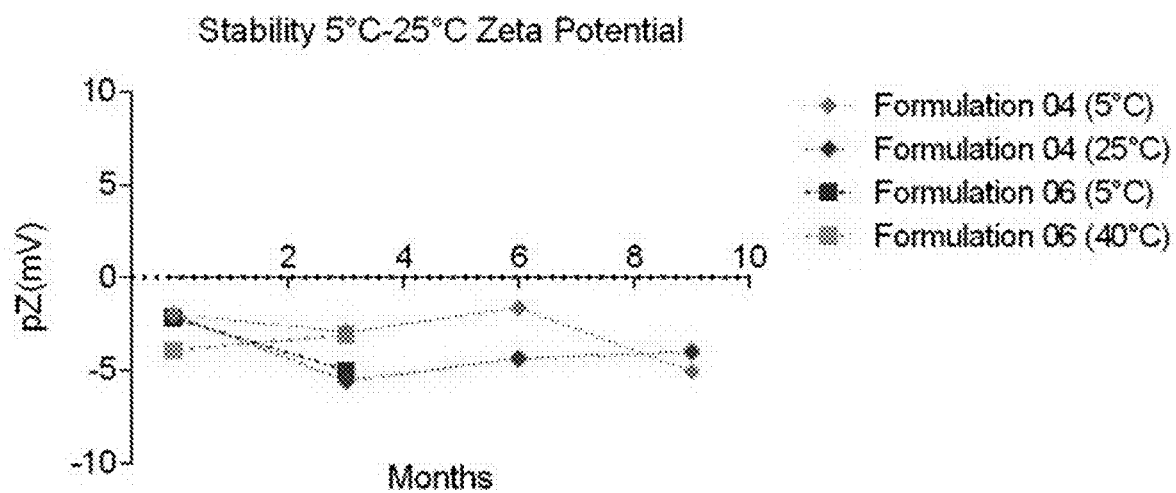
Figure 12E:
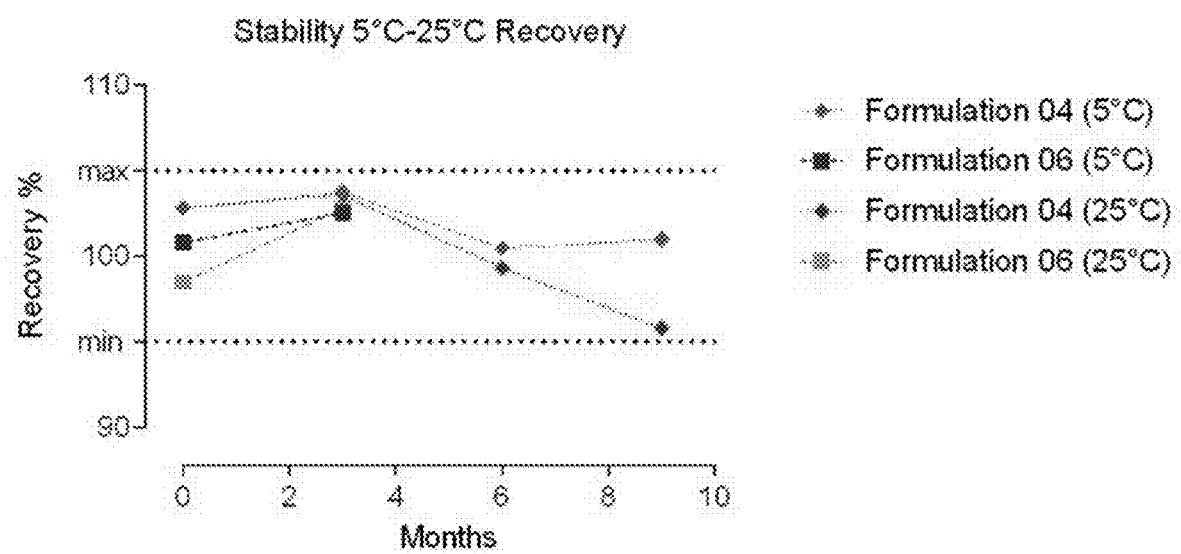
Figure 13A:
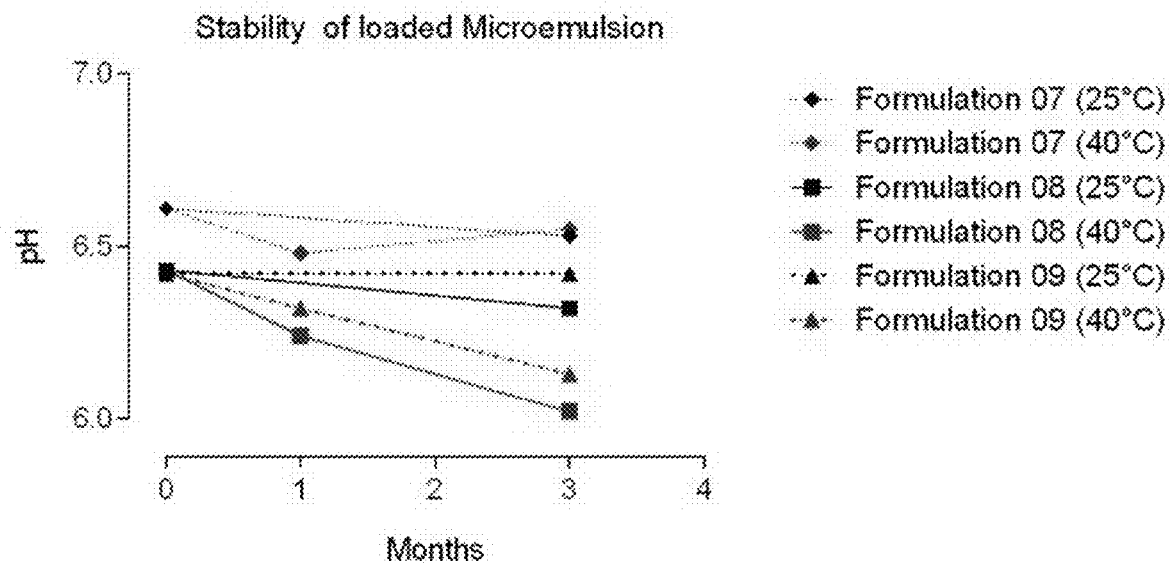
FIGS. 13A-13E depict the stability data at 3 months and at different conditions, 25±2° C./60±5% RH and 40±2° C./75±5 RH, of illustrative formulations of the microemulsions provided herein that contain an active ingredient, such as sorafenib tosylate. For example.
Figure 13B:
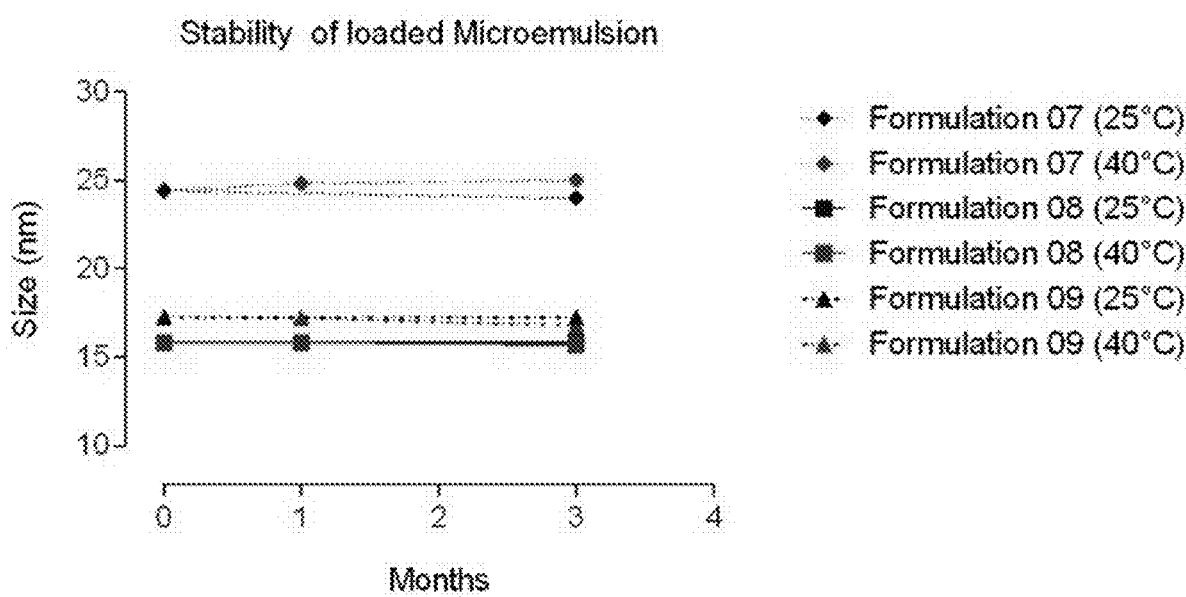
Figure 13C:
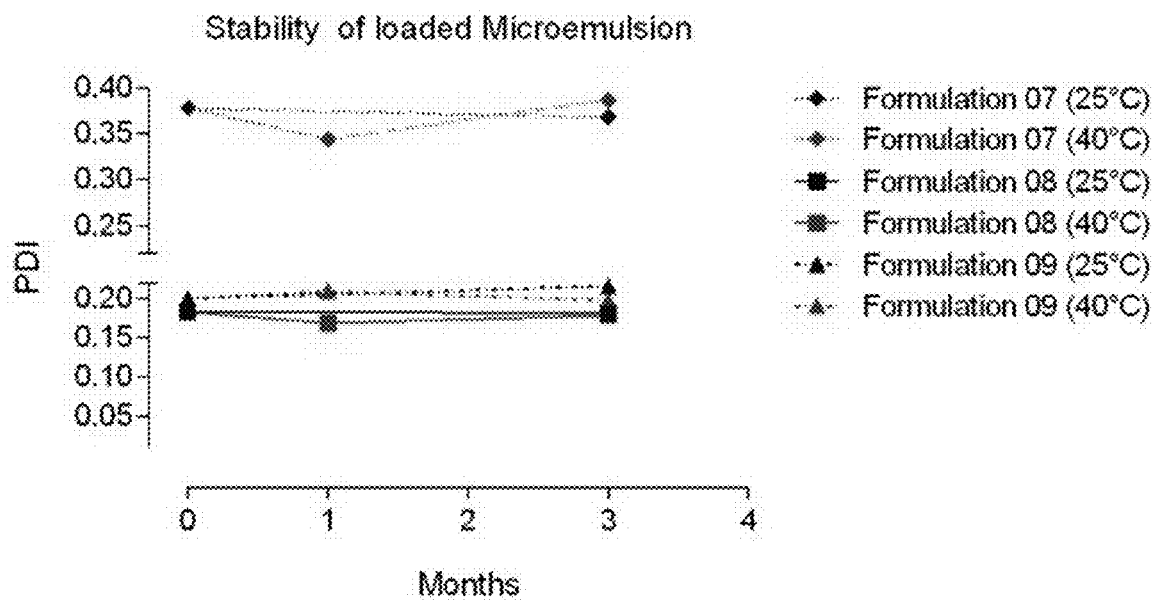
Figure 13D:
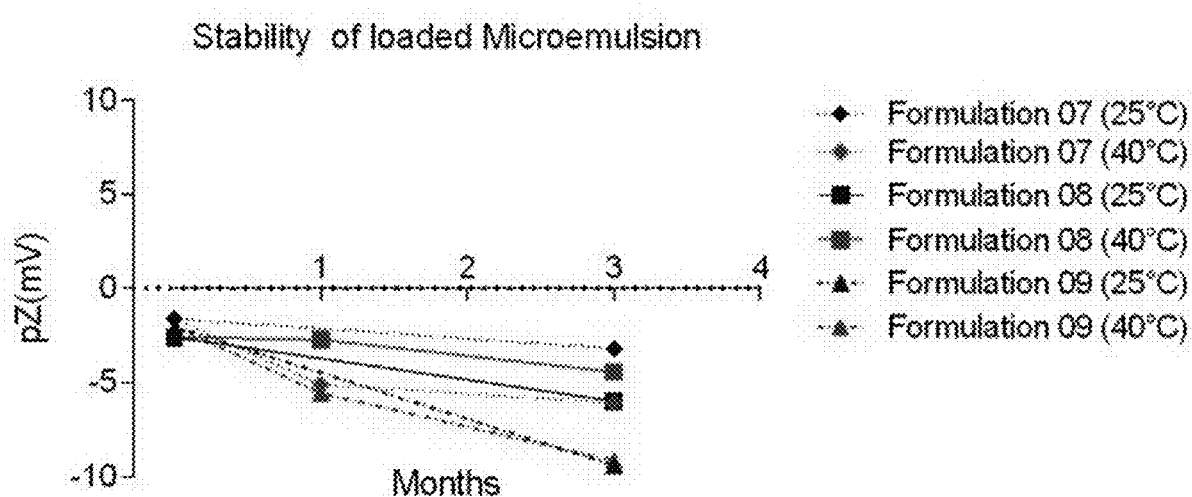
Figure 13E:
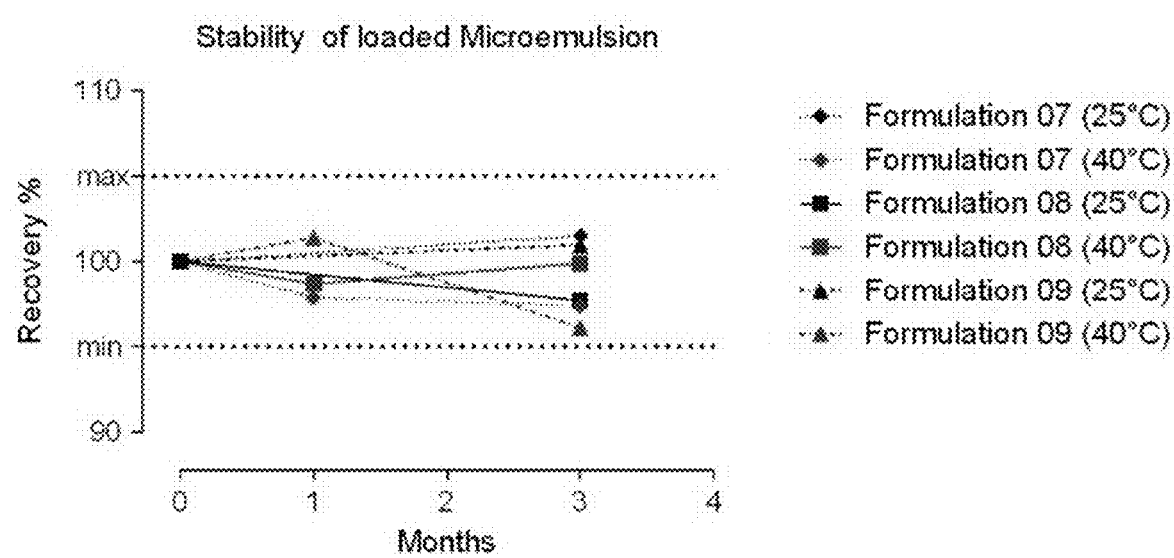

A stability study was performed on formulation 03 for up to 24 months. The results are shown in FIGS. 10A-10E and FIGS. 11A-11D. The stability data obtained at 25° C., 40° C. and 5° C. is shown in FIGS. 10A-E, which shows: pH (FIG. 10A), osmolality (FIG. 10B), size (FIG. 10C), and pZ (FIG. 10D). In FIG. 10E, the graph shows the concentration of latanoprost in the long-term stability study (25° C.±2° C., RH=60%±5%), expressed as recovery % according to the different study times. The concentration of latanoprost stayed within the specification limits for the whole duration of the analysis. FIG. 11A shows the PDI and the average particle size distribution determined during the course of the long-term stability study (25° C.±2° C., RH=60%±5%). FIGS. 11B-11D show the PDI and the average particle size determined at 40° C. for 6 months, 60° C. for 3 weeks, and 4° C. for just over 10 months, respectively. The measured parameters were within the expected ranges for the duration of the study.

Example 8

Stability of Formulations 04 and 06 of Example 6, Containing Masoprocol

Formulations 04 and 06 as described in Example 6 were subjected to long term stability studies to evaluate their stability profiles (25° C.±2° C., RH=60%±5%, 5° C.±3° C.). FIGS. 12A-12E show the pH (FIG. 12A), osmolality (FIG. 12B), size (FIG. 12C), pZ (FIG. 12D) and percentage of masoprocol recovery (FIG. 12E) determined during the course of the long-term stability study. The measured parameters remained within the expected ranges for the duration of the study.

Example 9

Stability of Formulations 07, 08, and 09

Formulations 07, 08 and 09, which contain sorafenib tosylate, as described in Example 6 were subjected to stress tests and long-term stability tests to evaluate their stability.

FIGS. 13A-13E show the pH (FIG. 13A), size (FIG. 13B), polydispersity index (FIG. 13C), pZ (FIG. 13D) and percentage of sorafenib recovery (FIG. 13E) determined during the course of the long-term stability study (25° C.±2° C., RH=60%±5%) and accelerated stability study (40° C.±2° C., RH=75%±5%). All formulations in both conditions showed parameters within the expected ranges for the whole duration of the study. In particular, formulation 07 exhibited very low variability in the pH value in the accelerated condition study.

Example 10

Cell Viability in Statens Seruminstitut Rabbit Cornea (SIRC) Cells

SIRC cells were allowed to grow at 37° C., 5% C02 in complete Basal Medium Eagle (BME) until subconfluence (70-90%) and then repeatedly exposed (6×5 min) to control formulations or microemulsions at different concentrations (%) (see Table 4). Cells were also exposed to negative control (sterile culture medium containing fetal bovine serum-free BME, CTRL−) and positive control (benzalkonium chloride 0.01%, CTRL+) for cytotoxicity. Analysis of cell viability was conducted by 3-(4,5-Dimethylthiazol-2-yl)-2,5-diphenyl tetrazolium bromide (MTT) assay using the ECVAM Protocol n° 17. The optical density (O.D.) was read at 570 nm in a microplate spectrophotometer. Cell viability was calculated as a percentage of negative control and statistical analysis was performed with one sample t-test vs. cut-off 50%.

TABLE 4

Microemulsions and relative active ingredient.

| Microemulsion | Active ingredient | Microemulsion % concentration |
|---|---|---|
| Formulation 1 | None | 100, 20, 10, 5, 2.5 |
| Formulation 04 | masoprocol 0.302% | |
| Formulation 2 | None | |
| Formulation 05 | sorafenib tosylate 0.300% | |
| Formulation 6 | None | |
| Formulation 06 | masoprocol 0.302% | |
| Formulation 7 | None | |
| Formulation 07 | sorafenib tosylate 0.300% | |
| Formulation 8 | None | |
| Formulation 08 | sorafenib tosylate 0.300% | |
| Formulation 9 | None | |
| Formulation 09 | sorafenib tosylate 0.300% | |
| Formulation 10 | None | |
| Formulation 11 | None | |
| Formulation 12 | None | |

Viability assessed by means of MTT demonstrated that no cellular mortality was associated with the microemulsions with or without active ingredient in any of the conditions tested (data not shown). Microemulsions containing vegetable and/or animal oils showed better cytocompatibility than the microemulsions containing mineral oils of synthetic origin.

Example 11

Efficacy In Vivo in a Chronic Ocular Hypertension Model

An in vivo pharmacological study was carried out on a chronic ocular hypertension model induced by means of cauterization of the episcleral veins (EVC) in rat. The hypotensive effect of the microemulsion containing latanoprost 0.005% (formulation 03) described in Example 6 was evaluated by administering one drop per day during the course of a treatment cycle lasting six days.

Figure 14:
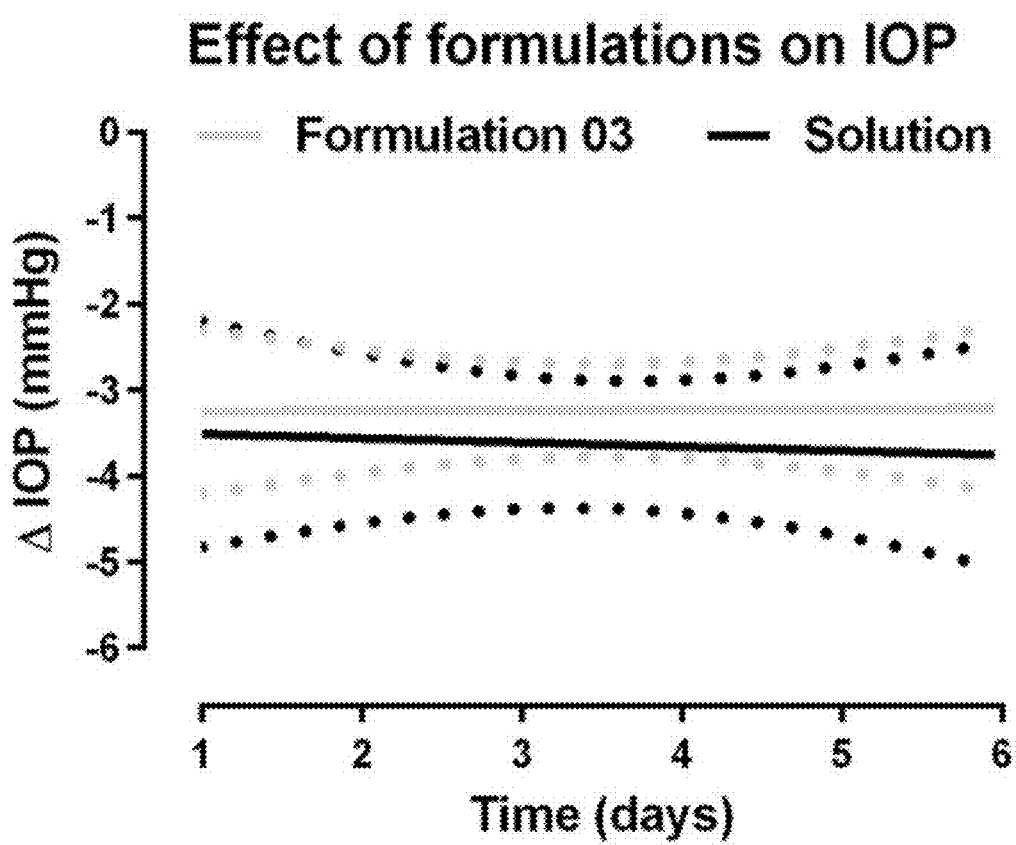
FIG. 14 depicts the efficacy of microemulsion containing latanoprost 0.005% (formulation 03), compared to a standard solution of latanoprost 0.005% (Solution), in EVC rats treated topically (6 days, once a day, 12 µl). Statistical analyses were performed using the Student t-test.

The latanoprost formulated in the microemulsion (formulation 03) produced an average reduction in intraocular pressure of 3.3 mmHg [n=15, 95% CI (2.9, 3.7)]. As is shown in FIG. 14, this effect was comparable (p>0.05, Student t-test) to the effect in the eye treated with a standard solution of latanoprost 0.005% (solution) [n=11, 3.6 mmHg, 95% Cl (3.2, 4.1)].

Example 12

Efficacy in the Retinal Ischemia-Reperfusion Model

A retinal ischemia-reperfusion (IR) model in rat was used to demonstrate the in vivo efficacy of the microemulsions containing masoprocol 0.302% (microemulsions formulations 04 and 06) and the microemulsions containing sorafenib tosylate 0.300% (microemulsions formulations 05 and 07), shown in Example 6. Before inducing the IR, Brown-Norway adult male rats weighing 200-250 g were treated topically for 2 days (12 µl b.i.d., right eye) and 1h before the insult (12 µl, right eye) with one of the following formulations: a) formulation 1; b) formulation 04; c) formulation 6; d) formulation 06; e) formulation 2; f) formulation 05; g) formulation 7 or h) formulation 07. Animals were anaesthetized, and, following mydriasis induced by tropicamide 0.5%, the IR was induced by inserting a 30 gauge needle into the front chamber of the right eye, connected to a container of physiological saline solution. The saline solution reservoir was positioned at a height from the operating table that guaranteed hydrostatic pressure at the eye level of approximately 130 mmHg. Raising intraocular pressure to such levels to induce the ischemia was confirmed by the "whitening" of the back of the eye. After 45 min, the needle was removed to restore the retinal blood flow.

Six hours after the ischemic episode, the animals were sacrificed and the retinas taken and preserved in 50 µl of storage stabilization solution (RNAlater®, available from ThermoFisher Scientific) to evaluate any potential effects of the microemulsions containing masoprocol 0.302% (formulations 04 and 06) or the microemulsions containing sorafenib tosylate 0.300% (formulations 05 and 07) on the pro-inflammatory gene expression by means of Real Time RT-PCR.

Figure 15A:
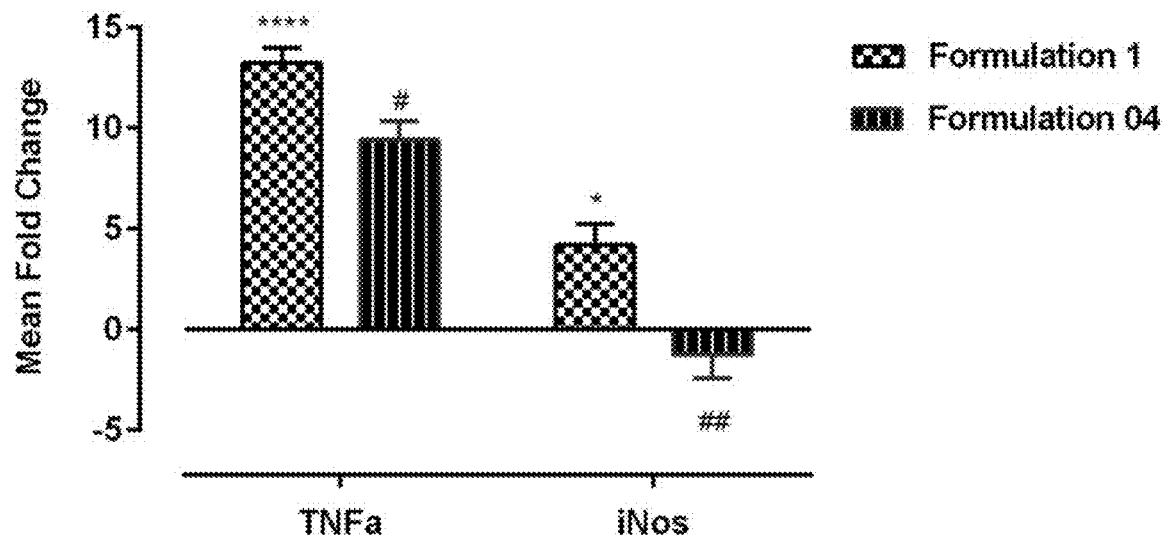
FIGS. 15A and 15B depict the gene expression of TNFa (tumor necrosis factor-a) and iNos in IR rat retinas pretreated topically 2 days and 1 h before inducing IR with microemulsions alone or containing masoprocol 0.302% (formulation 1, formulation 04; and formulation 6 or formulation 06) and sacrificed 6h after the ischemic episode.
Figure 15B:
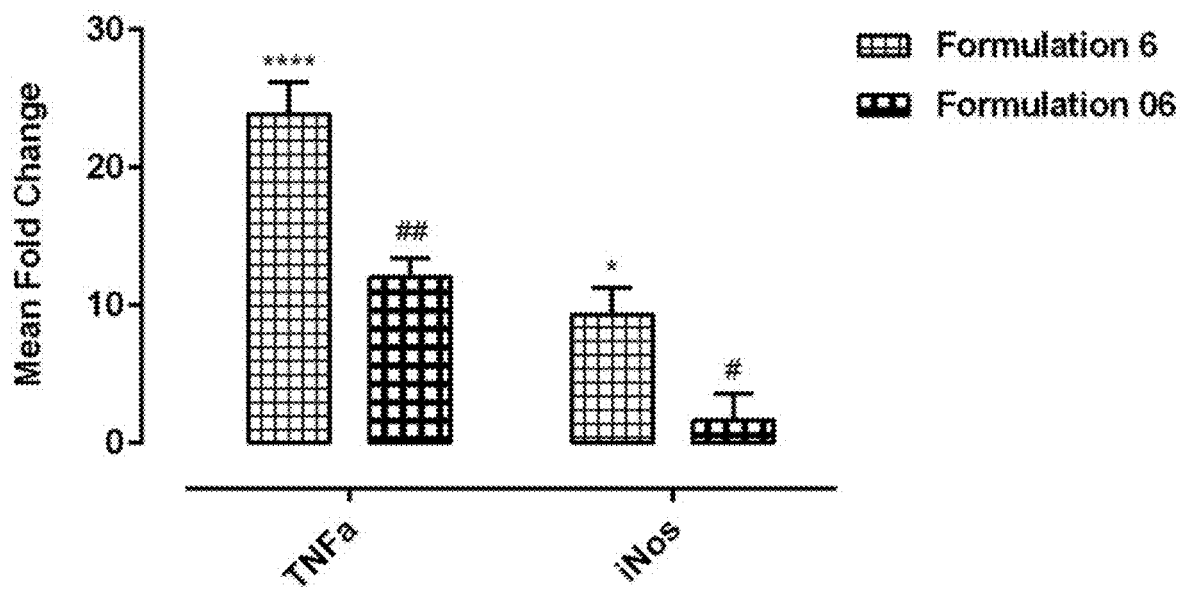

Analysis of the gene expression levels in the retinas of rats treated with microemulsions containing masoprocol 0.302% showed that: a) treatment with formulation 04 significantly reduced the TNF-alpha (28.7%) and iNos (130%) expression levels (#$p \leq 0.05$, ##$p \leq 0.01$) compared to that observed in the retinas of animals treated with the carrier alone (formulation 1; see FIG. 15A); b) treatment with formulation 06 significantly reduced the expression levels of TNF-alpha (49.5%) and iNos (82.4%) (#$p \leq 0.05$, ##$p \leq 0.01$) compared to that observed in the retinas of animals treated with the carrier alone (formulation 6; see FIG. 15B).

Figure 16A:
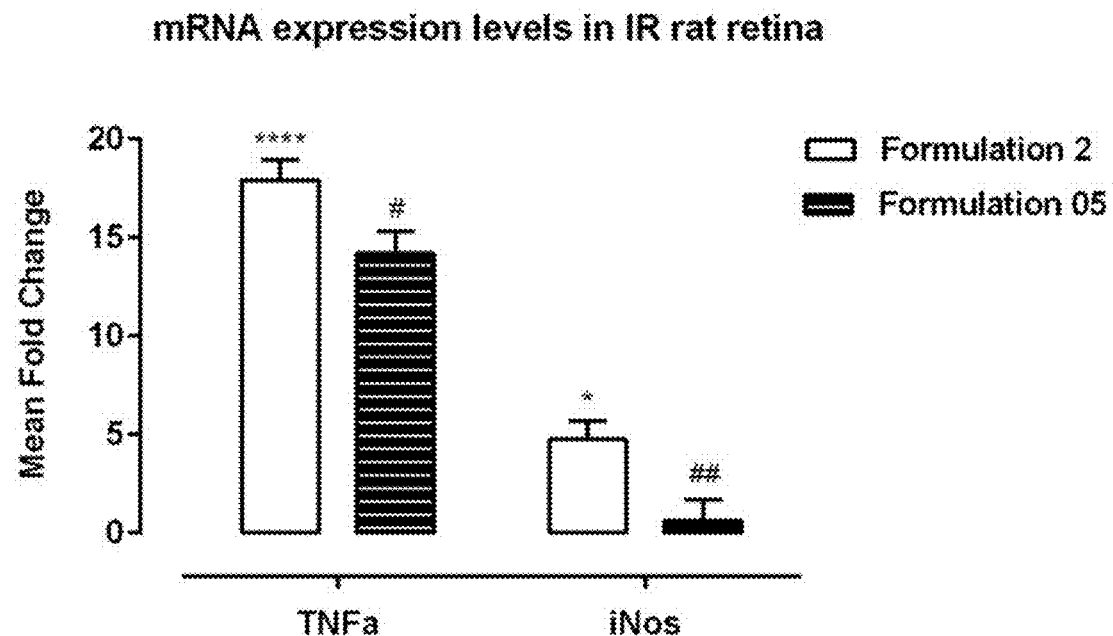
FIGS. 16A and 16B depict the gene expression of TNFa and iNos in IR rat retinas pretreated topically 2 days and 1h before inducing IR with microemulsions alone or containing sorafenib tosylate 0.300% (formulation 2, formulation 05; formulation 7 or formulation 07) and sacrificed 6h after the ischemic episode.
Figure 16B:
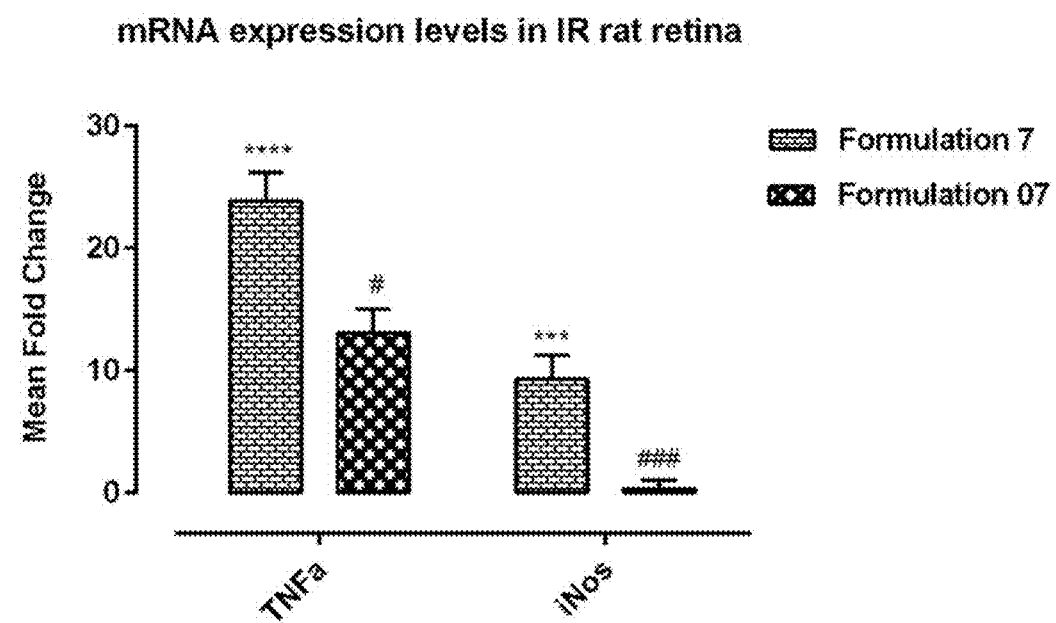

Treatment of ischemic rats with microemulsions containing sorafenib tosylate 0.300% showed that: a) formulation 05 significantly reduced the expression levels of the mRNA of TNF-alpha (20.7%) and iNos (87.3%) (#$p \leq 0.0^5$, ##$p \leq 0.01$) compared to that observed in retinas of animals treated with the carrier alone (formulation 2; see, FIG. 16A); b) treatment with formulation 07 significantly reduced the expression levels of TNF-alpha (45.3%) and iNos (96.5%) (#$p \leq 0.05$, ##$p \leq 0.01$) compared to what was observed in retina of animals treated with the carrier alone (formulation 7; see FIG. 16B).

Microemulsions comprising vegetable (formulation 07) and/or animal (formulation 06) oils showed an efficacy profile superior to that shown by microemulsions comprising mineral oils of synthetic origin (formulations 04 and 05).

Example 13

Efficacy in a Murine Model of Choroidal Neovascularization

In order to evaluate the potential anti-angiogenic action of the microemulsion containing masoprocol 0.302% (formulation 04) and the microemulsions containing sorafenib tosylate 0.300% (formulations 05 and 07) in age-related macular degeneration (AMD), a murine model of choroidal neovascularization (CNV) was used. For this purpose, 6-8 week-old male mice C57B16/J were pre-treated topically (5 µl b.i.d., both eyes) for three days preceding the induction of CNV and for the following 7 days with one of the following formulations: a) formulation 1; b) formulation 04; c) formulation 2; d) formulation 05; e) formulation 7 or f) formulation 07.

Before laser induction, the animals were anaesthetized by intraperitoneal injection with a solution of ketamine and xylazine (80 mg/Kg and 10 mg/Kg, respectively) and the pupil dilated with a topical application of 0.5% tropicamide. Subsequently, an aqueous solution of 2.5% hydroxy-propyl-methylcellulose was introduced into both eyes. The eyeground was observed with a camera and photocoagulation was induced using an image-guided laser system (Micron IV, Phoenix Research Laboratories, Pleasanton Calif.). Four radial spots were performed in both eyes at an equal distance from the optic nerve by laser impulse (532 nm; duration 100 msec; power 200 mW). The neovascularization area was determined by means of an immunofluorescence test. The animals were sacrificed by cervical dislocation and the enucleated eyes were put in 4% paraformaldehyde, then, the front segment of the eye was removed and the remaining part, called the 'eye-cup' (sclera, choroid, retinal pigment epithelium [RPE] and retina), was incubated in the presence of 0.7% FITC-Griffonia simplicifolia Isolectin for 16h. The volume of each spot was obtained by fluorescence acquisition of a stack of images (20-25 frames, each with a thickness of 1-µm) along the z axis, from the upper surface to the deepest focal plane, in relation to the RPE cells. The fluorescent areas of each frame composing a single stack were measured with the program ImageJ (NIH, Bethesda, Md.) and added together, thus obtaining a neovascularization volume measurement.

Figure 17:
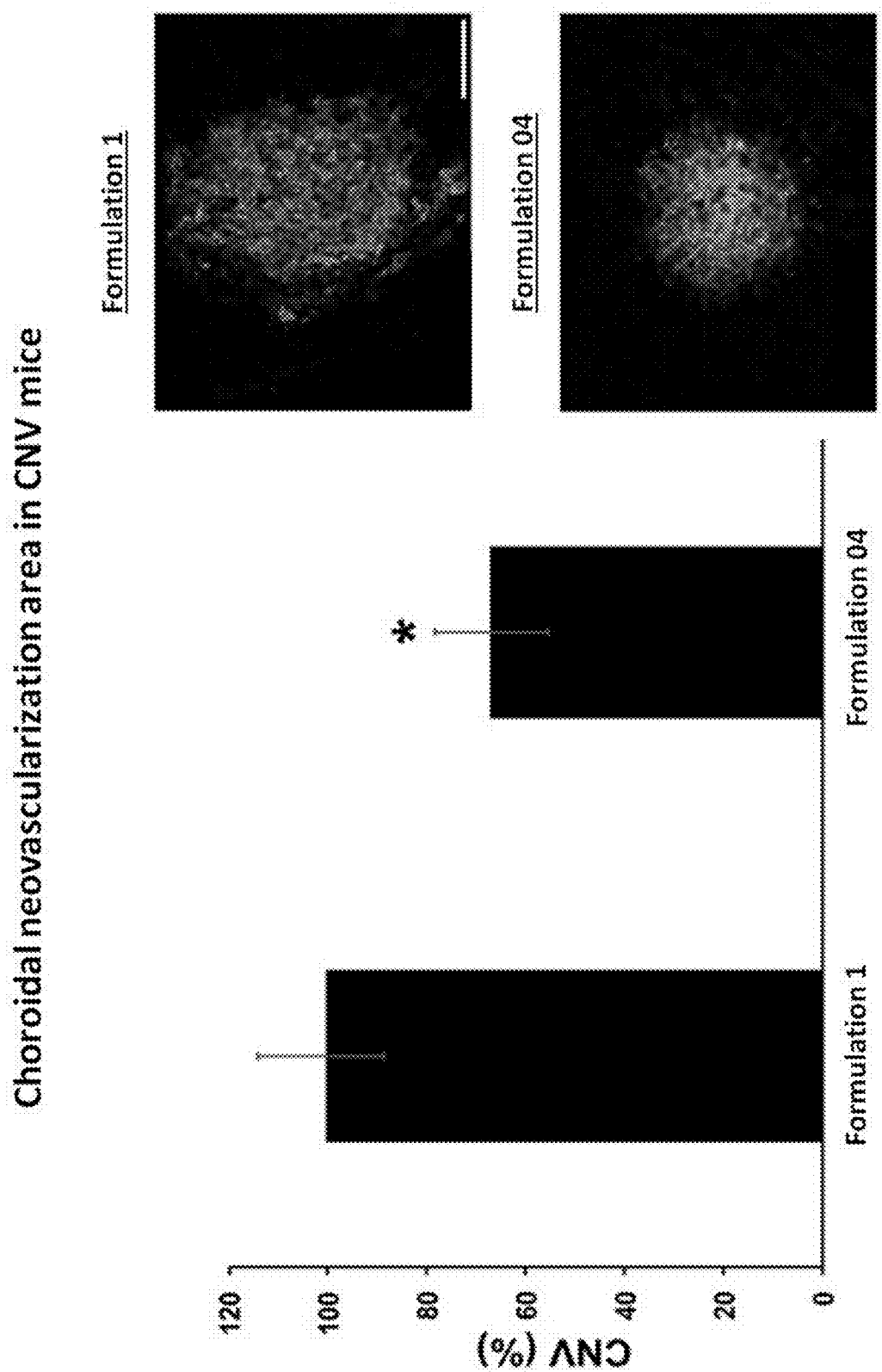
FIG. 17 depicts an analysis of the neovascularization areas in CNV mice pretreated topically for three days before inducing CNV and for the following 7 days with formulation 1 or formulation 04 containing masoprocol 0.302% (formulation 04). The data is represented as the average±SEM in relation to formulation 1. *p=0.0395 vs. formulation 1. Images representative of choroidal neovascularization (CNV) in animals treated with formulation 1 or formulation 04 are shown at a side. The scale bar represents 100 μm.
Figure 18A:
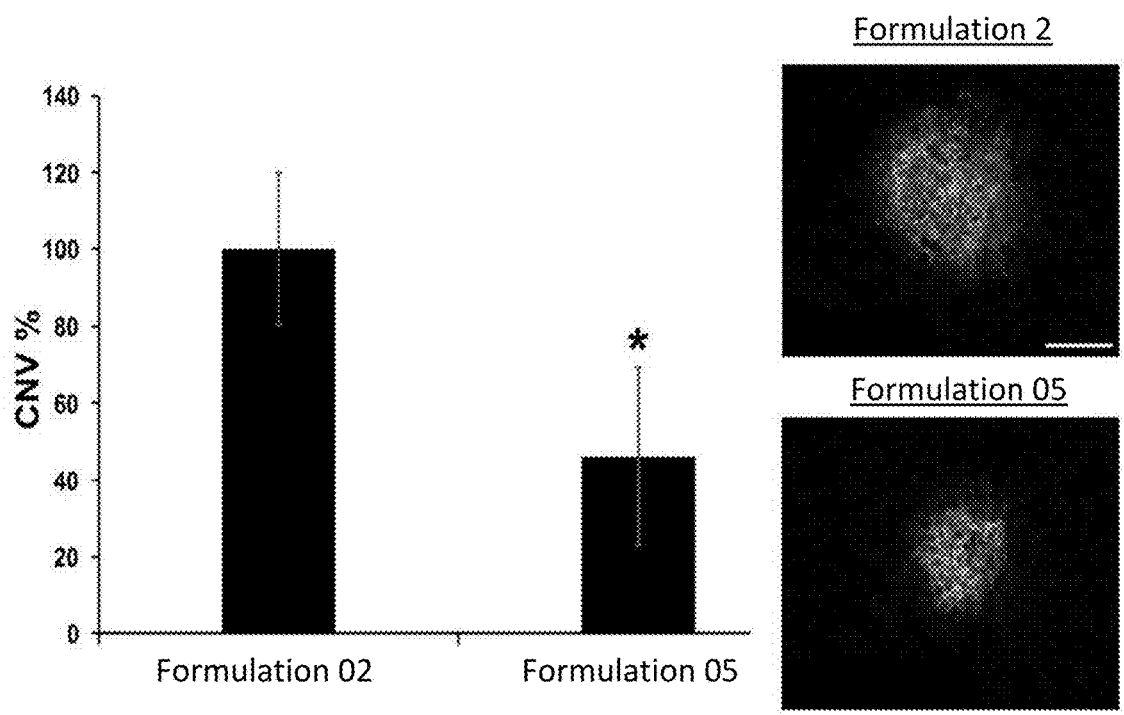
FIGS. 18A and 18B depict an analysis of the neovascularization areas in CNV mice pretreated topically for three days before inducing CNV and for the following 7 days with microemulsions alone or containing sorafenib tosylate 0.300% (formulation 2, formulation 05; formulation 7, formulation 07).
Figure 18B:
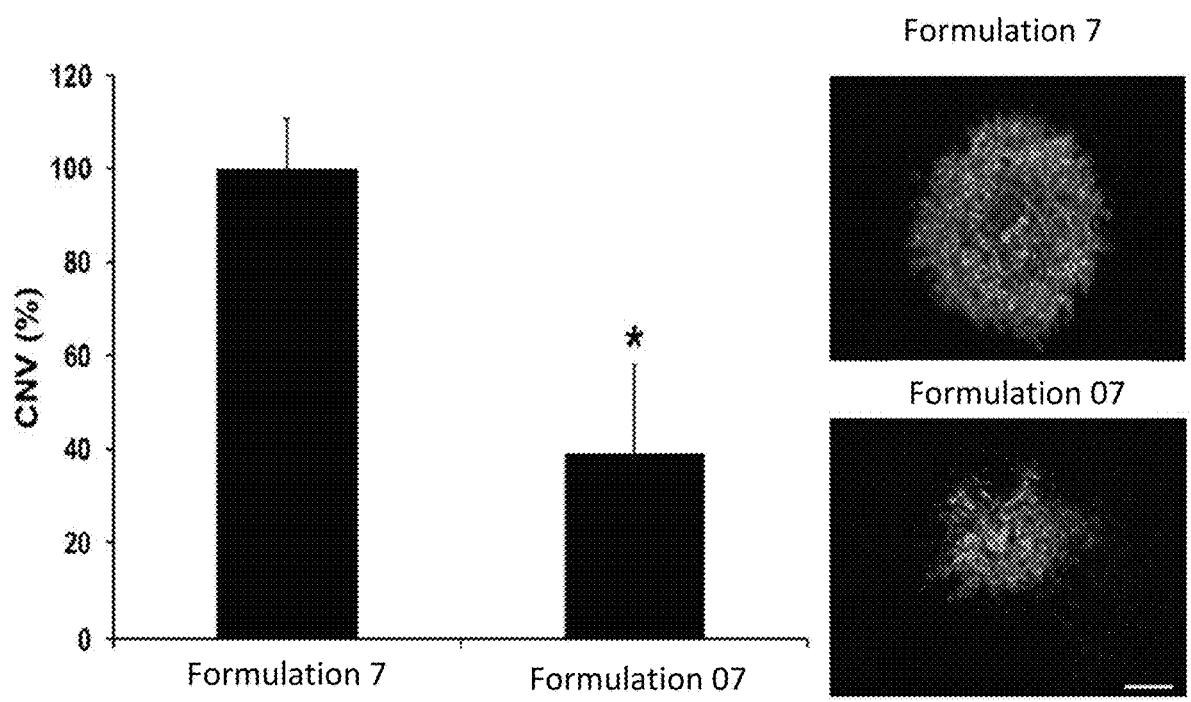
Figure 19A:
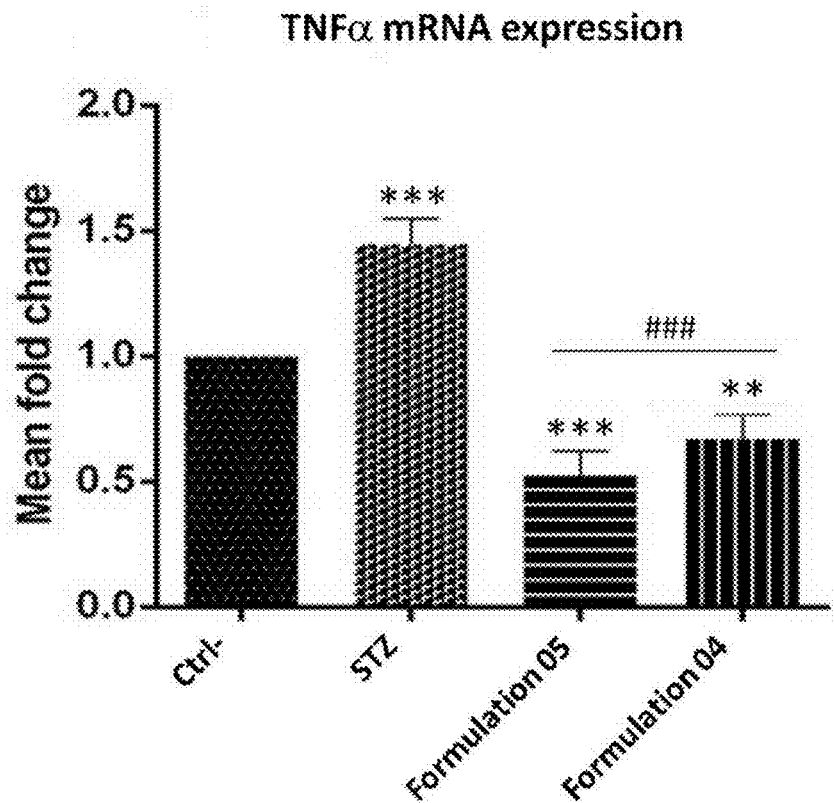
FIGS. 19A-19F depict the gene expression of TNFa, NFκB, IGF1, IGFR1, VEGFR1 and VEGFR2 in Ctrl− rat retinas, diabetic (STZ) and diabetic treated b.i.d. topically for 21 days with microemulsion containing masoprocol 0.302% (formulation 04) or microemulsion containing sorafenib tosylate 0.300% (formulation 05).
Figure 19B:
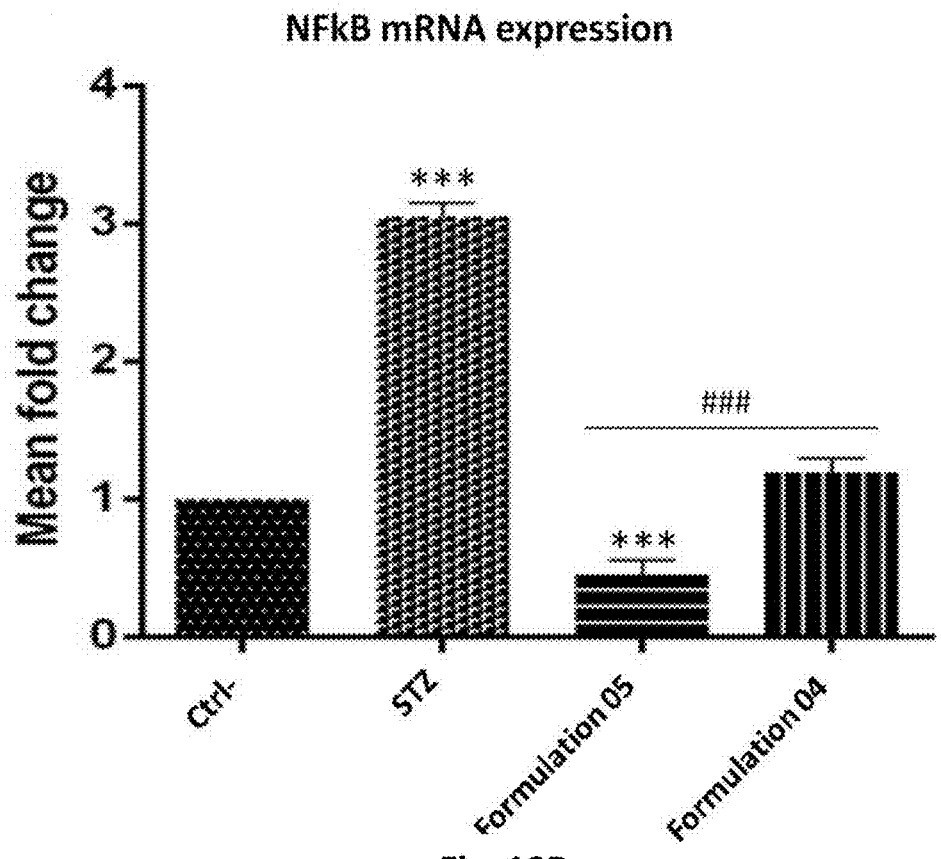
Figure 19C:
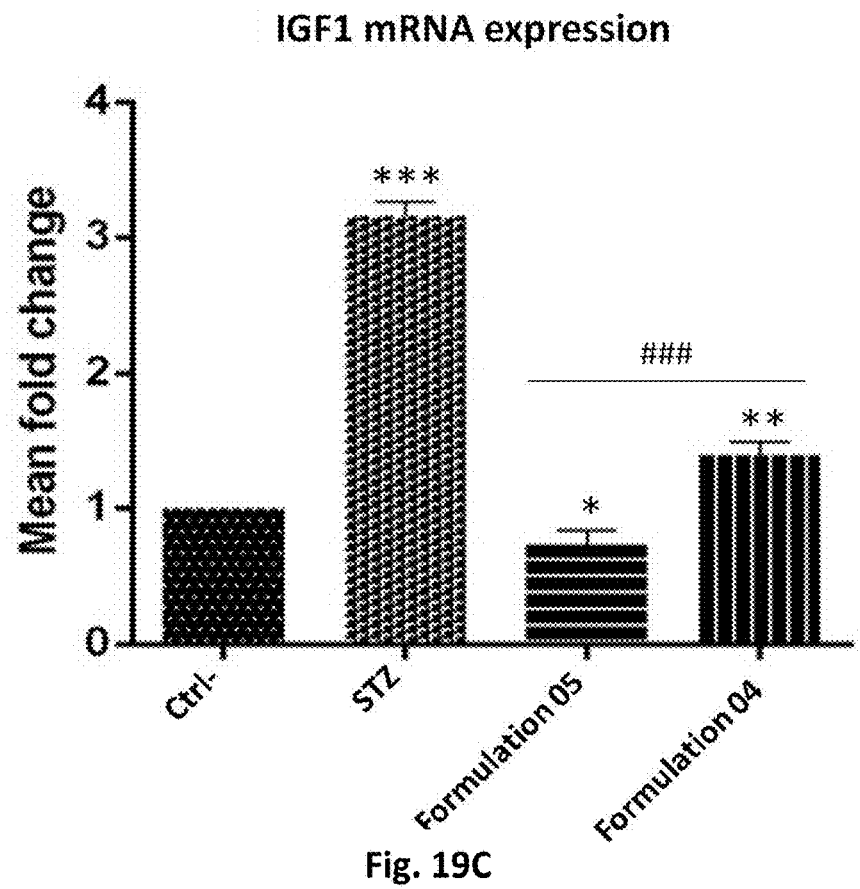
Figure 19D:
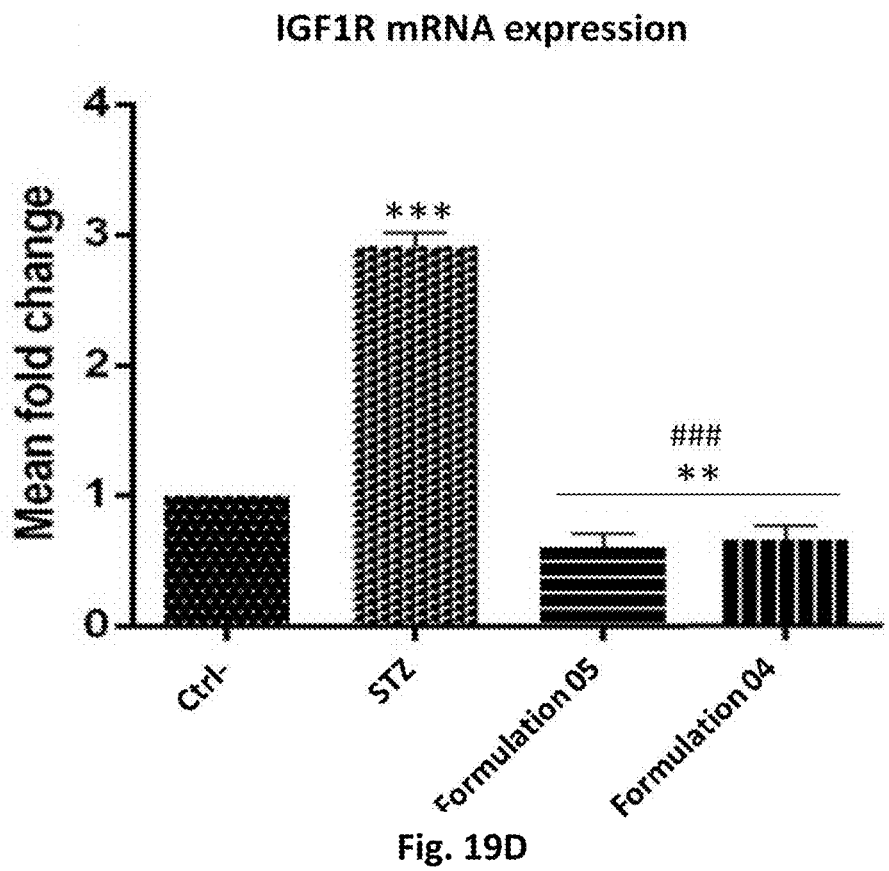
Figure 19E:
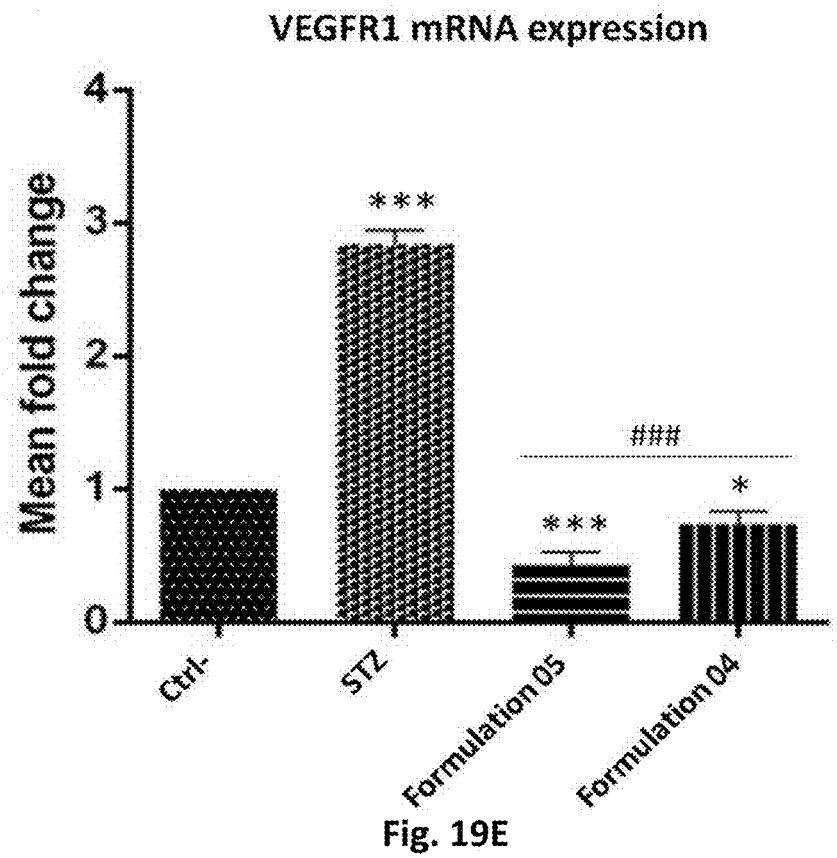
Figure 19F:
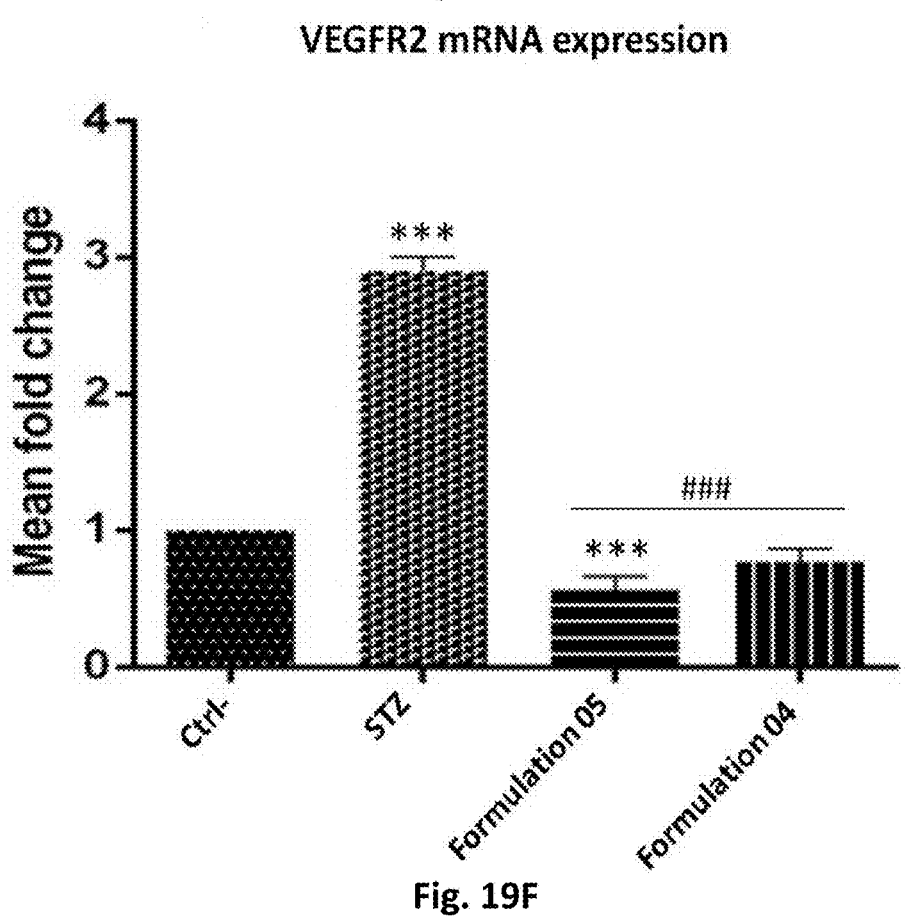
Figure 20A:
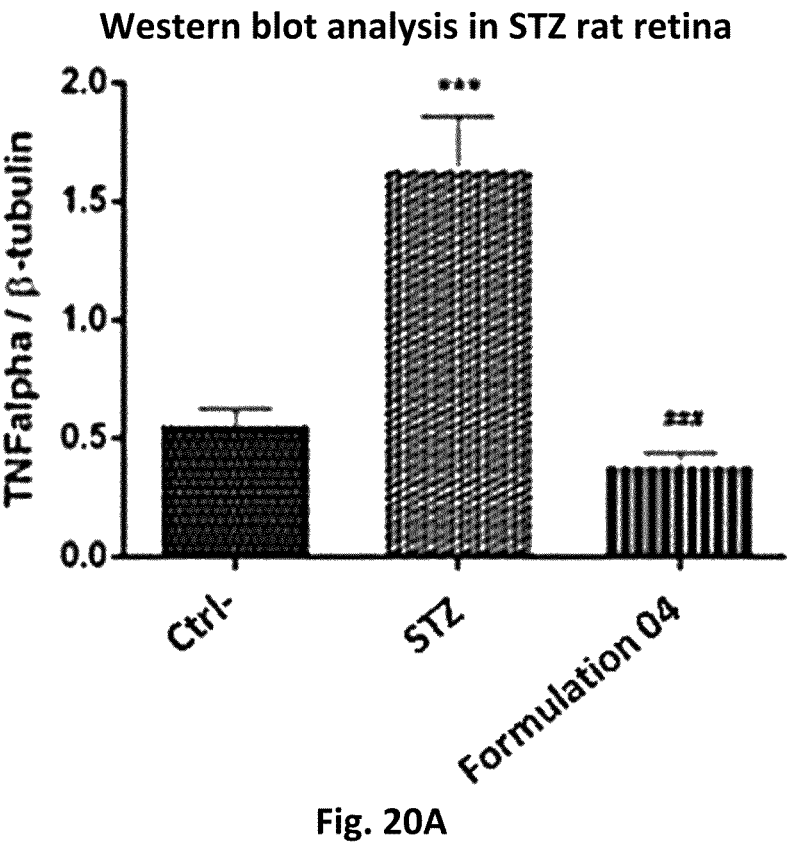
FIGS. 20A-20H depict the protein expression of TNFa (also referred to as TNF-alpha), VEGFR1 and VEGFR2 in Ctrl− rat retinas, diabetic (STZ) and diabetic treated b.i.d. topically for 21 days with microemulsion containing masoprocol 0.302% (formulation 04) or microemulsion containing sorafenib tosylate 0.300% (formulation 05).
Figure 20B:
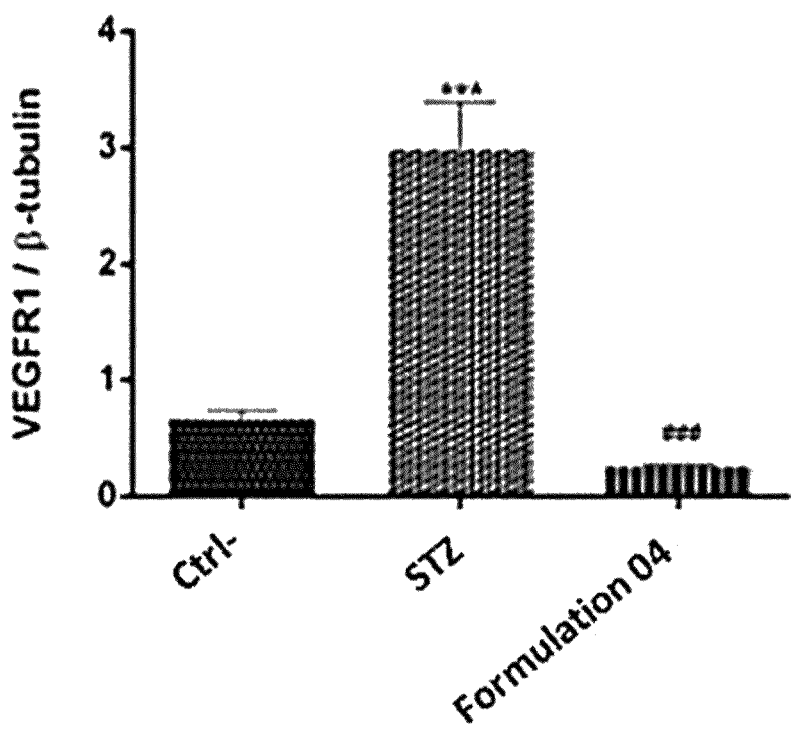
Figure 20C:
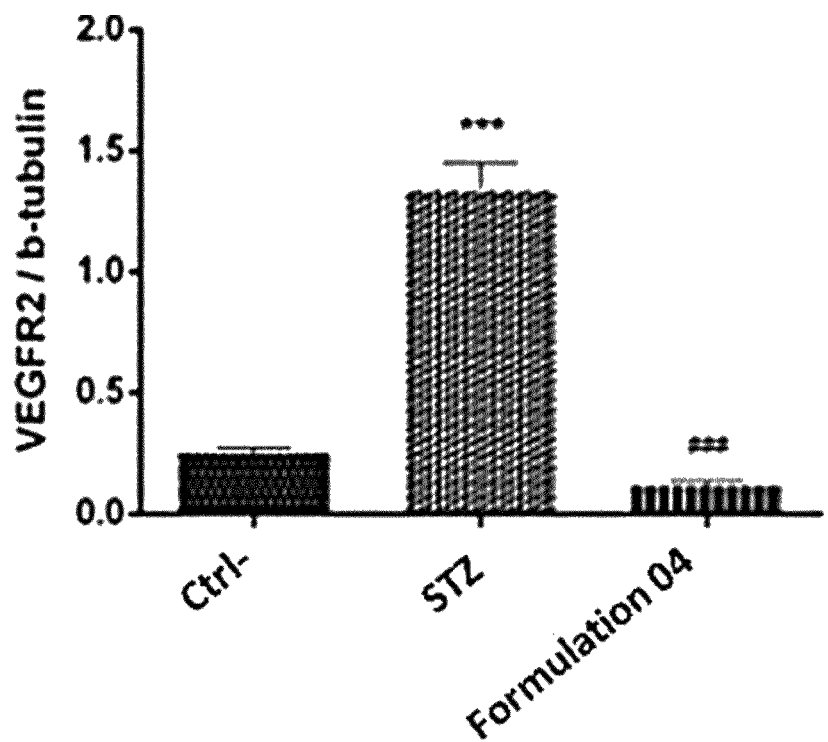
Figure 20D:
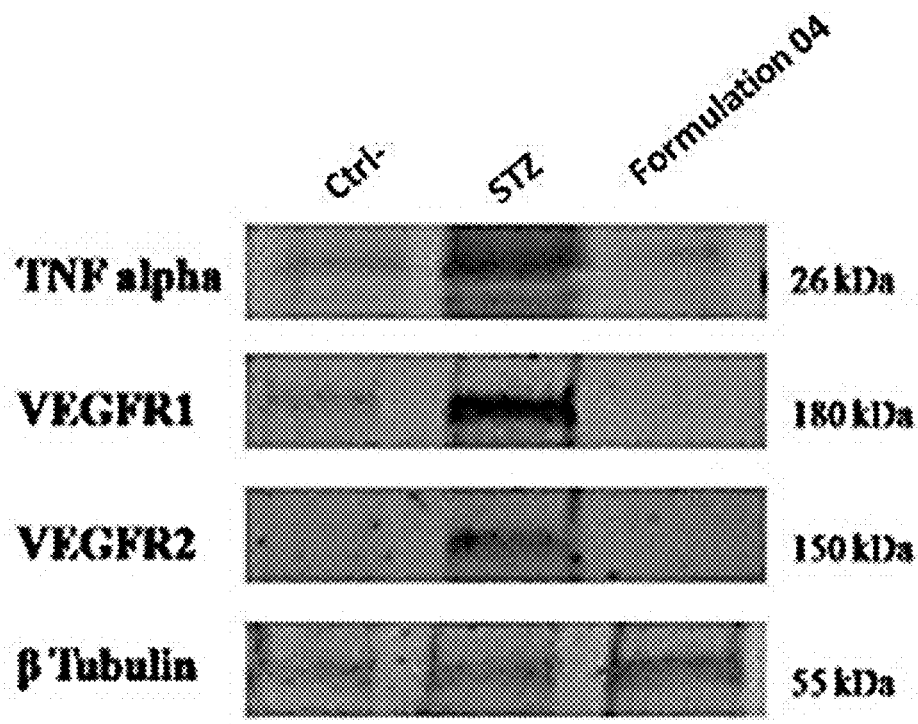
Figure 20E:
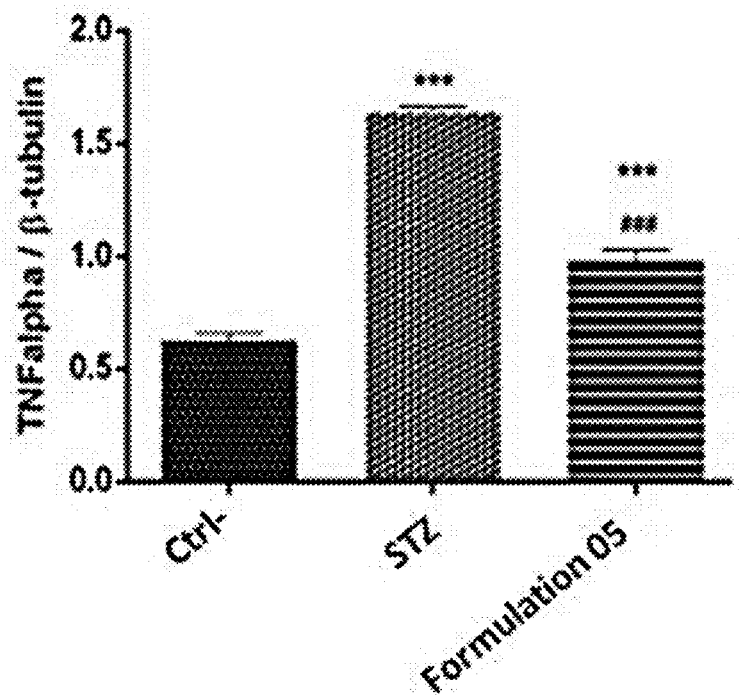
Figure 20F:
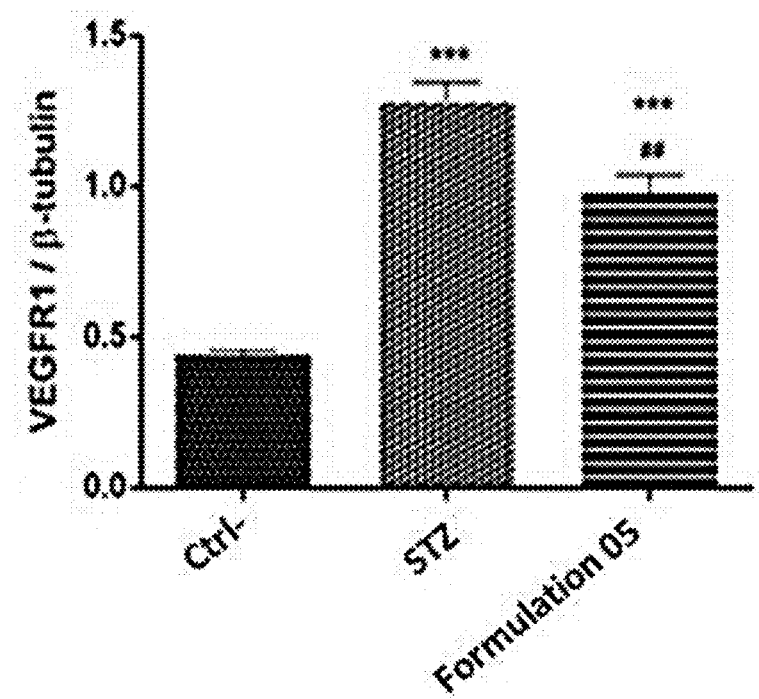
Figure 20G:
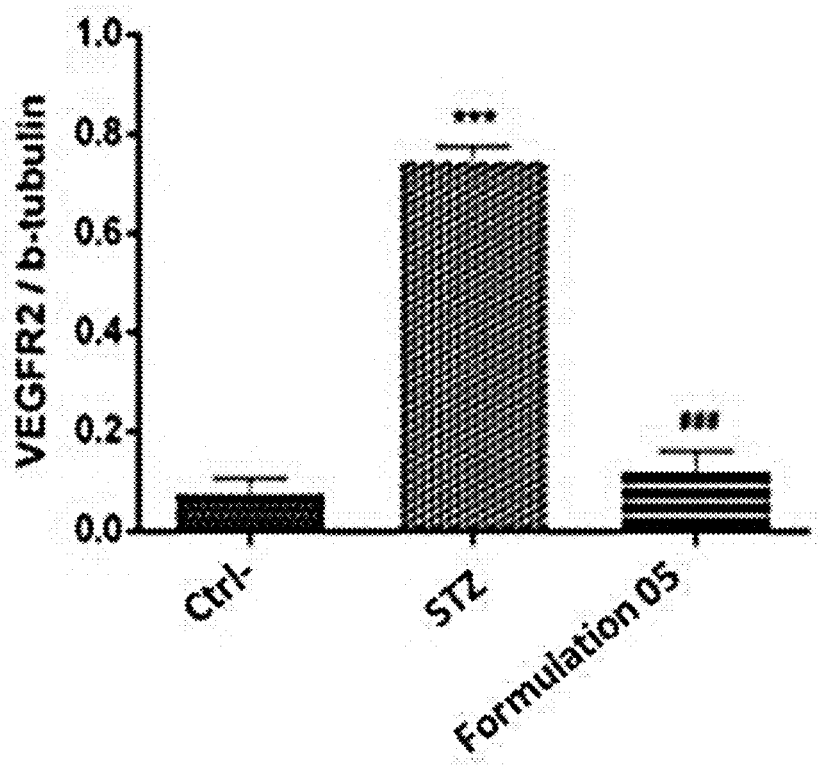
Figure 20H:
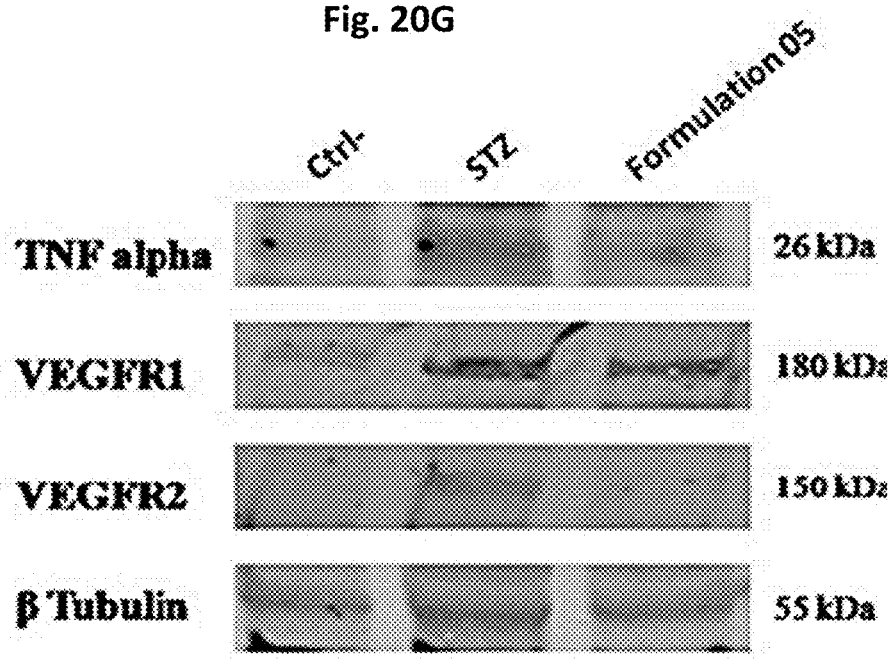

The results demonstrate that animals treated topically with the microemulsion containing masoprocol 0.302% (formulation 04) showed a statistically significant reduction in choroidal neovascularization of ~33% (p=0.0395) compared to carrier alone (formulation 1) (FIG. 17). The results also demonstrate that animals treated topically with the microemulsion containing sorafenib tosylate 0.300% (formulation 05) showed a 54% reduction of choroidal neovascularization; this result was highly significant when compared to animals treated with carrier alone (formulation 2) (FIG. 18A). Similar results have been obtained in animals treated topically with formulation 07, which significantly reduced choroidal neovascularization by ~61% (p=0.0001) when compared to carrier alone (formulation 7) (FIG. 18B).

The microemulsion containing vegetable oils and containing sorafenib tosylate 0.300% (formulation 07) showed an efficacy profile superior to that observed for the microemulsion comprising mineral oils of synthetic origin (formulation 05).

Example 14

Efficacy in the Streptozotocin-Induced Diabetic Retinopathy Model

Experiments were designed and conducted to assess the efficacy of the microemulsion containing masoprocol 0.302% (formulation 04) and of the microemulsion containing sorafenib tosylate 0.300% (formulation 05) in a model of the streptozotocin (STZ)-induced diabetic retinopathy in rat. To this end, Sprague-Dawley male rats (200-250 g) were injected with a single dose of STZ (60 mg/kg i.p.) and 24h later, the blood glucose was measured to include in the rest of the procedure only animals with glycaemia levels higher than 250 mg/dl. Starting from the day when the glycaemia was measured, the animals were treated for 21 days in both eyes b.i.d. and divided into the following treatment groups:
  negative control rats (ctrl-) and diabetic rats (STZ) treated with 12 µl of formulation 1 or formulation 2; and
  diabetic rats treated with 12 µl of formulation 04 or formulation 05.

At the end of the treatment course, animals were sacrificed, the bulbs enucleated and the retinas processed for performing gene and protein expression tests by Real Time RT-PCR and Western Blot, respectively.

Gene expression analysis by Real Time RT-PCR demonstrated that, when compared to STZ-treated animals, treatment with the microemulsion containing masoprocol 0.302% (formulation 04) (FIGS. 19A-19F) or containing sorafenib tosylate 0.300% (formulation 05) (FIGS. 19A-19F) significantly reduced the expression levels of the proinflammatory and pro-angiogenic genes analyzed (i.e. TNFa, NFκB, IGF1, IGF1R, VEGFR1 and VEGFR2).

Protein expression analysis by Western Blot showed that treatment with formulation 04 (FIGS. 20A-D) or formulation 05 (FIGS. 20E-H) significantly reduced the expression levels of TNFα, VEGFR1 and VEGFR2 compared to the retinas of the STZ-induced animals, thus confirming the anti-inflammatory and anti-angiogenic effect of both microemulsions formulated as described herein (FIGS. 20A-H).

Example 15

Ocular Tolerability In Vivo

A long-term tolerability study was carried out on New Zealand White rabbits (NZW) to assess ocular tolerability over a 28-day topical repeated-treatment course of the following microemulsions: a) formulation 1, b) formulation 04, c) formulation 6, d) formulation 06, e) formulation 2, f) formulation 05, g) formulation 7, or h) formulation 07.

Forty-eight rabbits were used, 24 males and 24 females, weighing approximately 2 Kg, and randomized into 8 experimental groups, each of which was composed of 6 animals (3 males and 3 females). In order to mimic the human dosing regimen, 50 µl of the formulations or of the vehicle (Tris pH 7.4) were administered b.i.d. by instillation into the conjunctival sac of the right (treated) or left (vehicle) eye, respectively.

The tolerability of the microemulsions studied was determined by means of the Draize test modified by McDonald et al., 1987 (Eye irritation, in Dermatotoxicology, Ed. Marzulli and Maibach, Hemisphere Publishing Corporation, 3rd Edition). Statistically significant differences were sought by means of General Linear Model analyses and unpaired t-test. Scores assigned using the modified Draize test did not evidence any difference among the sexes for any of the treatment groups.

Statistics show that there were no significant differences between the treated eye (right) and the control eye (left) in any of the treatment groups. There were no differences among microemulsion formulations containing the drugs (i.e., loaded microemulsions) and the relative vehicle (i.e. unloaded microemulsions).

The microemulsions based on vegetable and/or animal oils showed a better ocular tolerability profile than microemulsions comprising mineral oils of synthetic origin.

Example 16

Efficacy in a Murine Model of Dry Eye

A murine model of dry eye was used to establish the efficacy of the microemulsion containing masoprocol 0.302% (formulation 04), described in Example 6. To this end, C57BL/6 female mice (8-12 weeks old), were exposed for 3 days to a controlled environmental chamber (CEC) under low humidity (<20% RH; 21-22° C.) and constant airflow (20 L/min). In addition to the environmental conditions, 5 mg/ml of scopolamine was injected subcutaneously three times a day for 3 days. At the same time, a group of negative control animals (CTRL-) were kept in standard environmental conditions (21-23° C.; 50-60% RH).

Mice inside the CEC were divided into three groups: i) treated with formulation 1; ii) treated with formulation 04; and iii) un-treated positive control group (CTRL+). Seven microliters of the test items were instilled in both eyes twice daily for 3 days; animals outside the CEC, i.e. CTRL-, were left untreated for the entire duration of the study.

Fluorescein staining of the cornea was evaluated by slit lamp with a standardized grading system at baseline (t=0) and after 3 days of treatment (T3), to evaluate the corneal damage. The animals were sacrificed at T3 and the cornea excised and preserved for further processing aimed at evaluating potential effects of the treatments on pro-inflammatory gene expression by Real Time RT-PCR.

Figure 21:
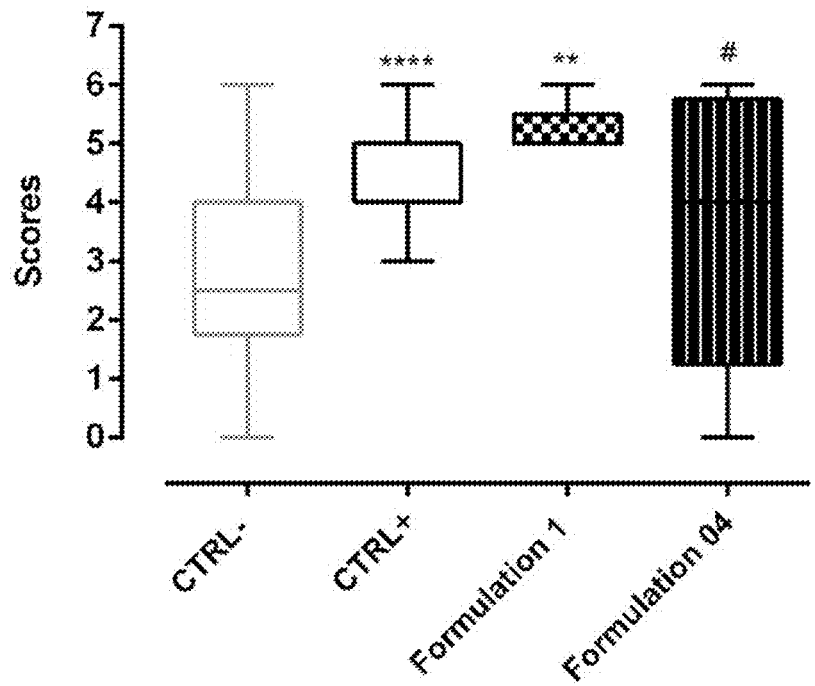
FIG. 21 depicts corneal damage measured by fluorescein staining at T3 in dry eye mice remained untreated (CTRL+) or treated topically for 3 days with formulation 1 or formulation 04 containing masoprocol 0.302% (formulation 04). The scores assigned to each group are graphed as box and whiskers bars spanning from minimum to maximum. One-way ANOVA followed by Dunnett's post-hoc test. $p \leq 0.01$, $**p \leq 0.0001$ vs. CTRL−. $\#p \leq 0.05$ vs. CTRL+.

Observations at T3 showed that corneal staining of CTRL+ mice was significantly worsened (p≤0.0001) with respect to CTRL-. Treatment with formulation 1 did not produce any remarkable amelioration over CTRL+, while formulation 04 significantly reduced corneal score (p<0.05, vs CTRL+) (FIG. 21).

Figure 22:
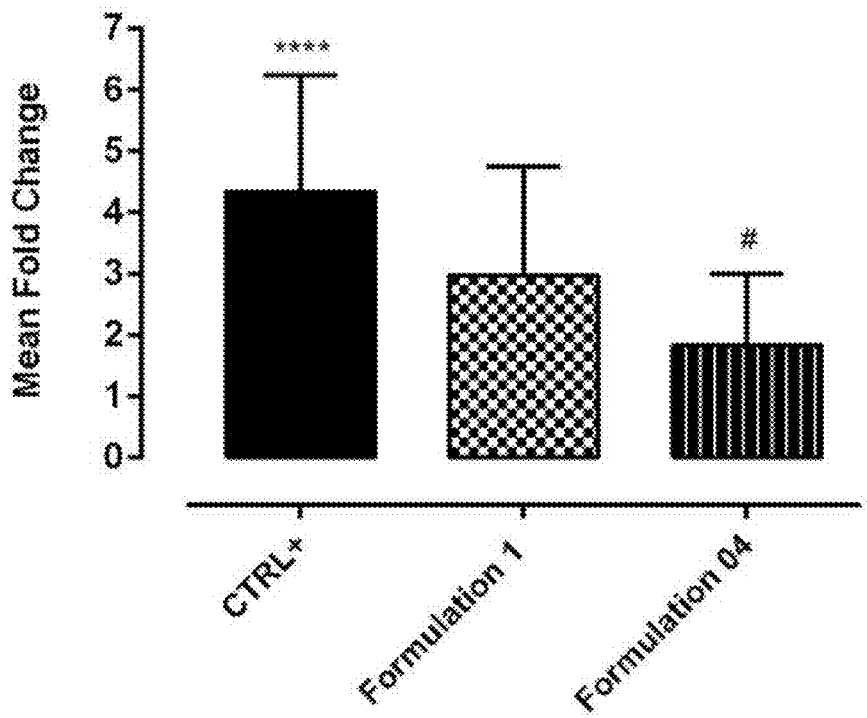
FIG. 22 depicts the gene expression of TNFa in the cornea of dry eye mice remained untreated (CTRL+) or treated topically for 3 days with formulation 1 or formulation 04 containing masoprocol 0.302% (formulation 04). The data represents the average±SEM of the Fold Change in relation to the calibrator (CTRL−). $\#p \leq 0.05$ vs. CTRL+; $****p \leq 0.0001$ vs. CTRL−. One-way ANOVA followed by Sidak's post-hoc test.

Analysis of gene expression showed that treatment with formulation 04 significantly reduced TNFa expression levels by 58% compared to CTRL+ animals (#p<0.05, vs CTRL+) (FIG. 22). The microemulsion containing masoprocol 0.302% (formulation 04) was effective in reducing ocular signs in a murine model of dry eye, a pathology of the ocular surface.

Since modifications will be apparent to those of skill in this art, it is intended that this invention be limited only by the scope of the appended claims.

The invention claimed is:
1. A pharmaceutical composition that is an oil-in-water microemulsion, comprising:
  a) a lipid phase comprising an oily component and one or more surfactant(s) and one or more co-surfactant(s);

b) an aqueous phase comprising one or more surfactant(s), and one or more co-surfactants; and c) a pharmaceutically active compound, wherein:

the weight/volume ratio between the total amount of surfactant and co-surfactant in the lipid phase to the total amount of surfactant and co-surfactant in the aqueous phase is from 2 to 10;

the weight/volume ratio between the amount of oily component in the lipid phase to the total amount of surfactant and co-surfactant in the aqueous phase is from 0.2 to 1.0; and in the resulting oil-in-water microemulsion, the average particle size is less than 30 nm.

2. The composition of claim 1, wherein:

the size distribution of particles in the resulting microemulsion is 15 nm 10 nm; and the polydispersity index (PDI) is within the range 0.02-0.380, inclusive, or 0.02 to 0.2, inclusive, or 0.02 to 0.15, inclusive, or is less than 0.2 or less than 0.12 or less than 0.1.

3. The composition of claim 1, wherein:

the weight/volume ratio between the total amount of surfactant and co-surfactant in the lipid phase to the amount of surfactant and co-surfactant in the aqueous phase is 2.2 to 9.8, inclusive, or 2.4 to 8.6, inclusive;

the weight/volume ratio between the amount of oily component in the lipid phase to the amount of surfactant(s) and co-surfactant(s) in the aqueous phase is from 0.22 to 0.98, inclusive, or from 0.24 to 0.96, inclusive; and in the lipid phase, the weight/volume ratio between the oily component and the surfactant(s) and co-surfactant(s) is from 0.05 to 1.4, inclusive.

4. The composition of claim 3, wherein, in the lipid phase, the weight/volume ratio between the oily component and the surfactant(s) and co-surfactant(s) is from 0.07 to 1.2, inclusive, or from 0.1 to 1, inclusive.

5. The pharmaceutical composition of claim 1, wherein:

the pharmaceutically active compound is an ophthalmic drug; and the composition is formulated for treatment of ophthalmic conditions or disorders.

6. A composition of claim 1, comprising:

an oily component in an amount of 0.4%-4.0% weight/volume (w/v) of the composition;

a surfactant or a mixture of a surfactant(s) and co-surfactant(s) in an amount of 5.71%-40.15% (w/v), inclusive, of the composition;

an aqueous component that is in an amount between 55.85%-93.89% (w/v), inclusive, of the composition; and a pharmaceutically active compound in an amount between 0.001 mg/ml to 50 mg/ml, inclusive, wherein:

all components of the composition are biocompatible; and the average particle size in the microemulsion composition is less than 30 nm.

7. The composition of claim 1, wherein the surfactant(s) and co-surfactant(s) are nonionic compounds with a Hydrophobic-Lipophilic Balance (HLB) between 8-16, inclusive.

8. The composition of claim 1 that contains one surfactant and one co-surfactant, or two surfactants and one co-surfactant, or two surfactants and two co-surfactants.

9. The composition of claim 1, wherein a surfactant in the lipid phase and the aqueous phase is the same, or a surfactant in the aqueous and lipid phase is different, and a co-surfactant in the aqueous and lipid phase is the same.

10. The composition of claim 1, wherein the co-surfactant(s) is/are glycerol and/or propylene glycol.

11. The composition of claim 1, wherein the surfactants are selected from among poloxamers, PEGylated fatty acids, polyoxyethylene sorbitan fatty acid derivatives, polyoxyethylenes, hydrogenated castor oil ethoxylates, glycerol esters of fatty acids, polyoxyl castor oil surfactants, amine oxides, and alcohol ethoxylates (nonionic).

12. The composition of claim 1, wherein the surfactants are selected from among polyethylene glycol, polyethylene glycol sorbitan monolaurate (polysorbate 20), polyethylene glycol sorbitan monooleate (polysorbate 80), polyethylene glycol sorbitan monopalmitate (polysorbate 40), lecithin, polyoxyl 35 castor oil, polyoxyl 40 hydrogenated castor oil, PEG 40 castor oil, PEG-60 hydrogenated castor oil, and polyethylene glycol 15-hydroxy-stearate.

13. The composition of claim 1, comprising one or more of an isotonizing (tonicity) agent, stabilizing agent, antioxidant, anti-microbial, thickening agent, and branched and linear polymers.

14. The composition of claim 1, wherein the lipid phase contains polysorbate 80 propylene glycol or polysorbate 80/polyoxyl 40 hydrogenated castor oil/propylene glycol as the surfactant(s)/co-surfactant, and the aqueous phase contains polyoxyl 40 hydrogenated castor oil/propylene glycol as the surfactant/co-surfactant.

15. The composition of claim 1 comprising one or more vegetable, animal or synthetic mineral oils selected from among soya oil, corn oil, linseed oil, sunflower seed oil, krill oil, cod-liver oil, fish oil, avocado oil, almond oil, babassu oil, borage oil, carob oil, cashew nut oil, grapeseed oil, coconut oil, *Oryza sativa* bran oil, castor oil, hemp seed oil, jojoba oil, peanut oil, poppy seed oil, sesame oil, walnut oil, olive oil, wheat-germ oil, argan oil, cottonseed oil, blackcurrant seed oil, oils rich in PUFAs by a fraction greater than 10%, esters of medium and long-chain fatty acids, and medium and long-chain triglycerides.

16. The composition of claim 1, wherein the pharmaceutically active compound is selected from among one or more gastrointestinal agents, antispasmodics, blood sugar regulators, nutraceuticals/minerals/electrolytes, platelet modifying agents, coagulants, cardiovascular agents, alpha-adrenergic agonists/alpha-adrenergic antagonists/vasodilators/arterial vasodilators, carbonic anhydrase inhibitor diuretics/loop diuretics/potassium-sparing diuretics/thiazide diuretics, other cardiovascular agents, beta-adrenergic antagonists, calcium channel blockers, angiotensin converting enzyme (ACE) inhibitors, dyslipidemics/HMG CoA Reductase inhibitors, anti-fungals, dermatological agents, anti-histamines, anesthetics, anti-bacterials, hormone-stimulating agents/substituents/modifiers, glycemic agents, hormone-suppressing agents, anti-mycobacterials, anti-virals, anti-neoplastics, immunomodulators, anti-inflammatory agents, analgesics, anti-convulsants, anti-Parkinson agents, antipsychotics, anti-depressants/anti-dementia agents/anti-anxiety medication, anti-myasthenic agents/agents for treating substances of abuse/central nervous system agents, bronchodilators/sympathomimetics/anti-cholinergics/inhaled corticosteroids/phosphodiesterase inhibitors/airborne disorders, other agents of the respiratory tract, anti-parasites, anti-glaucoma ophthalmic agents, other ophthalmic agents/anti-allergic ophthalmic agents, ophthalmic anti-inflammatories, prostaglandin analogues and ophthalmic prostamides, drugs for acidity-related disorders, drugs for gastrointestinal function disorders, drugs used for diabetes, vitamins, mineral supplements, antithrombotic agents, anti-hemorrhagics, cardiac therapy drugs, anti-hypertensives, diuretics, peripheral vasodilators, vasoprotectives, beta-blocking agents, calcium-antagonists, drugs acting on the renin-angiotensin system, lipid-lowering drugs, anti-fungals for dermatological use, emollients and protectives, drugs for injuries and ulcers, antipruritics, including anti-histamines, anaesthetics, anti-psoriasis drugs, antibiotics and chemotherapeutic agents for dermatological use, antiseptics and disinfectants, hypophyseal, hypothalamic hormones and similar, systemic corticosteroids, thyroid therapy, pancreatic hormones, homeostatic calcium, anti-bacterials for systemic use, anti-mycotics for systemic use, anti-viral drugs for systemic use, immune serums and immunoglobulins, anti-neoplastic agents, endocrine therapy, immunostimulants, immunosuppressants, anti-inflammatories and anti-rheumatics, topical products for joint and muscle pain, anti-epileptics, anti-parkinsonians, psycholeptics, psychoanaleptics, other nervous system drugs, rhinologic preparations, preparations for the pharyngeal cavity, drugs for obstructive disorders of the respiratory tract, preparations for coughs and colds, anti-histamines for systemic use, other preparations for the respiratory system, anti-infectives, anti-inflammatory agents, anti-inflammatory agents and anti-infectives combined, anti-glaucoma agents and miotics, mydriatics and cycloplegics, decongestants and anti-allergens, local anaesthetics, diagnostic agents, surgical aids, ocular vascular agents, corticosteroids, and corticosteroids with anti-infectives combined.

17. The composition of claim 1, wherein:
the pharmaceutically active compounds are for treating ophthalmic disorders; and
the disorders are selected from among dry eye, macular degeneration, glaucoma, infection, inflammation, allergy and diabetic retinopathy.

18. The composition of claim 17, wherein the pharmaceutically active compound is selected from among a prostaglandin inhibitor, an anti-angiogenic, and an anti-oxidant.

19. The composition of claim 18, wherein the pharmaceutically active compound is a prostaglandin inhibitor selected from among latanoprost, travoprost, bimatoprost, unoprostone, and pharmaceutically acceptable derivatives, hydrates, solvates, metabolites and salts thereof, or a polymorphic crystalline form thereof.

20. The composition of claim 18, wherein the pharmaceutically active compound is an anti-angiogenic agent selected from among sorafenib, sorafenib tosylate, regorafenib, regorafenib tosylate, regorafenib isethionate, regorafenib ethylsulfonate, apremilast, radotinib, spironolactone, and pharmaceutically acceptable derivatives, hydrates, solvates, metabolites and salts thereof, or a polymorphic crystalline form thereof.

21. The composition of claim 18, wherein the pharmaceutically active compound is an anti-oxidant selected from among nordihydroguaiaretic acid, and masoprocol, and pharmaceutically acceptable derivatives, hydrates, solvates, metabolites and salts thereof, or a polymorphic crystalline form thereof.

22. The composition of claim 1, wherein the pharmaceutically active compound is at a concentration of from 0.001 mg/ml to 50 mg/ml, inclusive, or 0.01 mg/ml to 30 mg/ml, inclusive, or 0.01 mg/ml to 50 mg/ml, inclusive.

23. The composition of claim 1, wherein a surfactant in the lipid phase and the aqueous phase is the same, or a surfactant in the aqueous and lipid phase is different, and a co-surfactant in the aqueous and lipid phase is different.

24. The composition of claim 1, wherein the pharmaceutically active compound is a hormone-stimulating agent/substituent/modifier selected from among adrenals, pituitary and sex hormones.

25. The composition of claim 1, wherein the pharmaceutically active compound is selected from among parathyroids.

26. The composition of claim 2, wherein the PDI is less than 0.2.

27. The composition of claim 2, wherein the PDI is less than 0.12.

28. The composition of claim 1, wherein the size distribution of particles in the resulting microemulsion is 15 nm±10 nm.

29. A method of treatment of an ophthalmic disorder or condition, comprising administering to a subject in need thereof a composition of claim 5.

30. The method of claim 29, wherein the ophthalmic disorder or condition is dry eye, macular degeneration, glaucoma, infection, inflammation, allergy or diabetic retinopathy.

31. The method of claim 30, wherein the pharmaceutically active compound in the microemulsion composition is masoprocol, sorafenib tosylate, and/or latanoprost.

32. A method for preparing a microemulsion, comprising:
a) preparing a lipid phase comprising an oily component and one or more surfactant(s) and, one or more co-surfactant(s); and
b) preparing an aqueous phase comprising one or more surfactant(s), and one or more co-surfactant(s), wherein:
the weight/volume ratio between the total amount of surfactant and co-surfactant in the lipid phase to the total amount of surfactant and co-surfactant in the aqueous phase is from 2 to 10; and
the weight/volume ratio between the amount of oily component in the lipid phase to the total amount of surfactant and co-surfactant in the aqueous phase is from 0.2 to 1.0; and
c) combining the lipid phase with the aqueous phase to form an oil-in-water microemulsion in which the average particle size is less than 30 nm.

33. The method of claim 32, wherein:
the weight/volume ratio between the amount of surfactant and co-surfactant in the lipid phase to the amount of surfactant and co-surfactant in the aqueous phase is 2.2 to 9.8, inclusive, or 2.4 to 8.6, inclusive;
the weight/volume ratio between the amount of oily component in the lipid phase to the amount of surfactant(s) and co-surfactant(s) in the aqueous phase is from 0.22 to 0.98, inclusive, or from 0.24 to 0.96, inclusive;
in the lipid phase, the weight/volume ratio between the oily component and the surfactant(s) and co-surfactant(s) is from 0.05 to 1.4, inclusive, whereby:
the size distribution of particles in the resulting microemulsion is 15 nm 10 nm; and
the polydispersity index (PDI) is within the range 0.02-0.380, inclusive, or 0.02 to 0.2, inclusive, or 0.02 to 0.15, inclusive, or is less than 0.2 or less than 0.12 or less than 0.1.

34. The method of claim 32, wherein step c) comprises titrating the lipid phase with the aqueous phase.

35. The method of claim 34, wherein:
the titration rate is described by the following equation:

$$V_{tit}=k \times (v_{tot}/1000 \text{ ml});$$

$V_{tit}$=titration speed in ml×min⁻1, k=2 ml×min⁻1, and $V_{tot}$=total volume of the formulation in ml.

36. A microemulsion composition prepared by the method of claim 33.

* * * * *